US011272695B2

(12) United States Patent
Shen et al.

(10) Patent No.: US 11,272,695 B2
(45) Date of Patent: Mar. 15, 2022

(54) GENETICALLY MODIFIED NON-HUMAN ANIMAL WITH HUMAN OR CHIMERIC PD-1

(71) Applicant: Biocytogen Pharmaceuticals (Beijing) Co., Ltd., Beijing (CN)

(72) Inventors: Yuelei Shen, Beijing (CN); Yanan Guo, Beijing (CN); Yang Bai, Beijing (CN); Rui Huang, Beijing (CN); Xiaofei Zhou, Beijing (CN); Meiling Zhang, Beijing (CN); Jiawei Yao, Beijing (CN); Chaoshe Guo, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/436,723

(22) Filed: Jun. 10, 2019

(65) Prior Publication Data

US 2019/0373868 A1 Dec. 12, 2019

Related U.S. Application Data

(63) Continuation of application No. PCT/CN2018/110069, filed on Oct. 12, 2018.

(30) Foreign Application Priority Data

| Oct. 13, 2017 | (CN) | 201710954868.9 |
| Feb. 9, 2018 | (CN) | 201810134049.4 |
| May 22, 2018 | (CN) | 201810496216.X |
| May 22, 2018 | (CN) | 201810496766.1 |
| Oct. 12, 2018 | (CN) | 201811188443.2 |

(51) Int. Cl.
| *A01K 67/027* | (2006.01) |
| *C07H 21/04* | (2006.01) |
| *G01N 33/50* | (2006.01) |

(52) U.S. Cl.
CPC ...... *A01K 67/0278* (2013.01); *G01N 33/5011* (2013.01); *A01K 2207/15* (2013.01); *A01K 2217/15* (2013.01); *A01K 2227/105* (2013.01); *A01K 2267/0331* (2013.01); *C07H 21/04* (2013.01)

(58) Field of Classification Search
CPC ............ A01K 67/0278; A01K 2207/15; A01K 2217/15; A01K 2227/105; C07H 21/04
See application file for complete search history.

(56) References Cited

U.S. PATENT DOCUMENTS

| 4,683,195 A | 7/1987 | Mullis et al. |
| 8,728,474 B2 | 5/2014 | Honjo et al. |
| 9,834,606 B2 | 12/2017 | Li et al. |
| 10,314,297 B2 | 6/2019 | Shen |
| 10,362,771 B2 | 7/2019 | Mashimo et al. |
| 10,457,960 B2 | 10/2019 | Frendewey et al. |
| 10,912,287 B2 | 2/2021 | Shen et al. |
| 2002/0115209 A1 | 8/2002 | Liu et al. |
| 2004/0033497 A1* | 2/2004 | Alarcon-Riquelme et al. |
| 2015/0106961 A1 | 4/2015 | Rojas et al. |
| 2015/0366174 A1* | 12/2015 | Burova et al. |
| 2016/0157469 A1 | 6/2016 | Burova et al. |
| 2017/0142943 A1* | 5/2017 | Mujica et al. |
| 2017/0247454 A1 | 8/2017 | Benz et al. |
| 2019/0343094 A1 | 11/2019 | Shen |
| 2019/0387724 A1 | 12/2019 | Shen |

FOREIGN PATENT DOCUMENTS

| CN | 1113518 | 12/1995 |
| CN | 103820454 | 5/2014 |
| CN | 104561095 | 4/2015 |
| CN | 104593418 | 5/2015 |
| CN | 106604635 | 4/2017 |
| WO | WO 2002/36789 | 5/2002 |
| WO | WO 2004/074320 | 9/2004 |
| WO | WO 2015/090230 | 6/2015 |
| WO | WO 2015/161276 | 10/2015 |
| WO | WO 2015/196051 | 12/2015 |
| WO | WO 2016/094481 | 6/2016 |
| WO | WO 2017/087780 | 5/2017 |
| WO | WO2018001241 | 1/2018 |
| WO | WO2018041118 | 3/2018 |
| WO | WO2018041119 | 3/2018 |
| WO | WO2018041120 | 3/2018 |

(Continued)

OTHER PUBLICATIONS

Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Yang et al., 2016, PNAS, 113(41), E6209-E6218, p. 1-10.*
Guo et al., 2015, Cell Research, vol. 25, p. 767-768.*
Lee et al., 2016, Drug Discovery Today: Disease Models, vol. 20, p. 13-20.*
Bryan et al., 2013, http://www.elsevierblogs.com/currentcomments/?p=962, Implications of protein fold switching, p. 1-4.*

(Continued)

*Primary Examiner* — Shin Lin Chen
(74) *Attorney, Agent, or Firm* — Fish & Richardson P.C.

(57) ABSTRACT

The present disclosure relates to genetically modified non-human animals that express a human or chimeric (e.g., humanized) programmed cell death protein 1 (PD-1), and methods of use thereof. In one aspect, the animals have an insertion of a sequence encoding a human or humanized programmed cell death protein 1 (PD-1) at an endogenous PD-1 gene locus. This animal model can express a PD-1 protein containing a functional domain of the human PD-1 protein, and can be used as an animal model for developing therapeutics for human diseases and disorders, and assessing the toxicity and/or the efficacy of these human therapeutics.

15 Claims, 21 Drawing Sheets

Specification includes a Sequence Listing.

(56) References Cited

FOREIGN PATENT DOCUMENTS

| WO | WO2018041121 | 3/2018 |
|---|---|---|
| WO | WO2018068756 | 4/2018 |
| WO | WO2018086583 | 5/2018 |
| WO | WO2018086594 | 5/2018 |
| WO | WO2018121787 | 7/2018 |
| WO | WO2018177440 | 10/2018 |
| WO | WO2018177441 | 10/2018 |

OTHER PUBLICATIONS

Maqbool et al., 2015, Biochemical Society Transactions, vol. 43, No. 5, p. 1011-1017.*

Burova et al., 2015, GeneSeq Accession No. BCK42308, Computer printout, pp. 268-270.*

Burova et al., 2015, GeneSeq Accession No. BCK42308, Computer printout, pp. 295-297.*

Burova et al., 2018, US 20180206462 A1, effective filing date, Jun. 19, 2014.*

Baidu Tieba, "Biocytogen pd-1 Humanized Mice," https://tieba.baidu.com/p/4610326082, Jun. 14, 2016 (Jun. 14, 2016), p. 1, paragraphs 1-2, and figures on p. 2.

GenBank Accession No. L27440.1, "Human PD-1 gene, complete cds," GenBank, Dec. 28, 1994, 2 pages.

GenBank Accession No. X67914.1, "M.musculus PD-1 mRNA," GenBank, Jul. 26, 1993, 3 pages.

Lute et al., "Human CTLA4 knock-in mice unravel the quantitative link between tumor immunity and autoimmunity induced by anti-CTLA-4 antibodies," Blood, American Society of Hematology, 106(9):3127-3133.

Supplementary Partial European Search Report in European Appln. No. EP 17819238, dated Nov. 21, 2019, 10 pages.

Auerbach et al., "Establishment and Chimera Analysis of 129/SvEv- and C57BL/6-Derived Mouse Embiyonic Stem Cells Lines," 2000.

Burova et al., "Abstract 266: Antitumor activity of REGN2810, a fully human anti-PD-1 monoclonal antibody, against MC38.Ova tumors grown in immune-competent humanized PD-1 mice," Cancer Research, 2015, 75(15):31 (Abstract only).

Creelan, Benjamin C. "Update on immune checkpoint inhibitors in lung cancer." Cancer Control 21.1 (2014): 80-89.

Festing et al., "Revised nomenclature for strain 129 mice," Mammalian Genome, 1999, 10:836.

Hirano et al., "Blockade of B7-H1 and PD-1 by monoclonal antibodies potentiates cancer therapeutic immunity," Cancer research, 2005, 65(3):1089-1096.

International Search Report and Written Opinion in Appln. No. PCT/CN2017/090320, dated Sep. 20, 2017, 18 pages (with English translation).

International Search Report and Written Opinion in Appln. No. PCT/CN2018/110069, dated Jan. 11, 2019, 10 pages.

Ito, M. et al., NOD/SCID/ γcnull mouse: an excellent recipient mouse model for engraftment of human cells, Blood 100 (9): 3175-3182, 2002.

Kaufmann et al., "PD-1 and CTLA-4 Inhibitory Consignaling Pathways in HIV Infection and the Potential for Therapeutic Intervention," The Journal of Immunology, 2009, 182:5891-5897.

Kowk et al., "Pembrolizumab (Keytruda)," 2016, 2777-2789.

Palmer et al., "In vivo blockade of the PD-1 receptor suppresses HIV-1 viral loads and improves CD4+ T cell levels in humanized mice," J. Immunol., 2012, 190:211-219.

Raedler, "Keytruda (pembrolizumanb): first PD-1 inhibitory approved for previously treated unresectable or metastatic melanoma," American health & drug benefits, 2015, 8:96-100.

Topalian et al., "Safety, activity, and immune correlates of anti-PD-1 antibody in cancer," New England Journal of Medicine, 2012, 366(26):2443-2454.

Yin et al., "Delivery technologies for genome editing," Nature Reviews Drug Discovery 16.6 (2017): 387-399.

Aida et al., "Cloning-free CRISPR/Cas system facilitates functional cassette knock-in in mice," Genome Biol, Dec. 1, 2015, 16(87):1-11.

Baidu Tieba, "Biocytogen pd-1 Humanized Mice," retrieved from URL: https://tieba.baidu.com/p/4610326082, 2016, 10 pages (with English translation).

Burova et al., "Abstract 1484: Combined treatment with anti-LAG-3 and anti-PD-1 fully human nonoclonal antibodies inhibits tumor growth in immunocompetent double-humanized LAG-3/PD-1 mice," Cancer Res., 2016, 76(14):1-2.

Burova et al., "Characterization of the Anti-PD-1 Antibody REGN2810 and Its Antitumor Activity in Human PD-1 Knock-In Mice," Mol Cancer Ther., May 1, 2017, 16(5):861-870.

GenBank Accession No. NP_005009.2, "Programmed cell death 1 [*Homo sapiens* (human)]" Sep. 15, 2016, 3 Pages.

GenBank Accession No. XM 017596382, "PREDICTED: Rattus norvegicus programmed cell death 1 (Pdcd1), transcript variant X2, mRNA," Jul. 26, 2016, 2 pages.

Gennequin et al., "CRISPR/Cas-induced double-strand breaks boost the frequency of gene replacements for humanizing the mouse Cnr2 gene," Biochem. & Biophysical Res. Comm., Nov. 29, 2013, 441:815-819.

Harms et al., "Mouse Genome Editing Using the CRISPR/Cas System," Curr Protoc Hum Genetics, Oct. 2014, 83:15.7.1-15.7.27, 39 Pages.

Klimke et al., "State-of-art humanized mouse models and the CRISPR/Cas9 technology at TaconicArtemis," Transgenic Res., Oct. 1, 2014, 23(5): 3 Pages.

Li, "Heritable gene targeting in the mouse and rat using a CRISPR-Cas system," Nature Biotech., Aug. 2013, 31(8):681-683.

Rotte, "Combination of CTLA-4 and PD-1 blockers for treatment of cancer," J. Exp. & Clin. Cancer Res., Dec. 1, 2019, 38(255):1-12.

Schilit et al., "Pronuclear Injection-Based Targeted Transgenesis," Curr Protoc Hum Genet., Oct. 2016, 91:15.10.1-15.10.28, 42 Pages.

Yoshimi et al., "ssODN-mediated knock-in with CRISPR-Cas for large genomic regions in zygotes," Nature Comm., Jan. 20, 2016, 7(10431): 11 Pages.

Cui et al., "Review of CRISPR/Cas9 sgRNA design tools," Interdisciplinary Sciences: Computational Life Sciences, Jun. 2018, 10(2): 12 pages.

International Preliminary Report on Patentability in Appln. No. PCT/CN2017/090320, dated Jan. 10, 2019, 11 pages.

International Preliminary Report on Patentability in Appln. No. PCT/CN2018/110069, dated Apr. 23, 2020, 6 pages.

Zhu et al., "Humanising the mouse genome piece by piece," Nature communications, Apr. 23, 2019, 10(1):1-13.

* cited by examiner

FIG. 20

| Score | Expect | Method | Identities | Positives | Gaps |
|---|---|---|---|---|---|
| 291 bits(746) | 1e-103 | Compositional matrix adjust. | 169/290(58%) | 200/290(68%) | 4/290(1%) |

```
Mouse   1    MWVRQVPWSFTWAVLQLSWQSGWLLEVPNGPWRSLTFYPAWLTVSEGANATFTCSLSNWS    60
             M + Q PW   WAVLQL W+ GW L+ P+ PW      TF PA L V+EG NATFTCS  SN S
Human   1    MQIPQAPWPVVWAVLQLGWRPGWFLDSPDRPWNPPTFSPALLVVTEGDNATFTCSFSNTS    60

Mouse   61   EDLMLNWNRLSPSNQTEKQAAFCNGLSQPVQDARFQIIQLPNRHDFHMNILDTRRNDSGI    120
             E  +LNW R+SPSNQT+K AAF      SQP QD RF++ QLPN  DFHM+++ RRNDSG
Human   61   ESFVLNWYRMSPSNQTDKLAAFPEDRSQPGQDCRFRVTQLPNGRDFHMSVVRARRNDSGT    120

Mouse   121  YLCGAISLHPKAKIEESPGAELVVTERILETSTRYPSPSPKPEGRFQGMVIGIMSALVGI    180
             YLCGAISL PKA+I+ES   AEL VTER  E   T +PSPSP+P G+FQ +V+G++ L+G
Human   121  YLCGAISLAPKAQIKESLRAELRVTERRAEVPTAHPSPSPRPAGQFQTLVVGVVGGLLG-    179

Mouse   181  PVILLLAWALAVFCSTSMSEARGAGSKDDTLKEEPSAAPVPSVAYEELDFQGREKT--PE    238
             L+LL W LAV CS +       GA        LKE+PSA PV SV Y ELDFQ REKT  P
Human   180  -SLVLLVWVLAVICSRAARGTIGARRTGQPLKEDPSAVPVFSVDYGELDFQWREKTPEPP    238

Mouse   239  LPTACVHTEYATIVFTEGLGASAMGRRGSADGLQGPRPPRHEDGHCSWPL    288
             +P    TEYATIVF  G+G S+  RRGSADG +    +P R EDGHCSWPL
Human   239  VPCVPEQTEYATIVFPSGMGTSSPARRGSADGPRSAQPLRPEDGHCSWPL    288
```

GENETICALLY MODIFIED NON-HUMAN ANIMAL WITH HUMAN OR CHIMERIC PD-1

CLAIM OF PRIORITY

This application is a continuation of and claims priority to international Application No. PCT/CN2018/110069, filed on Oct. 12, 2018, which claims the benefit of Chinese Patent Application App. No. 201710954868.9, filed on Oct. 13, 2017, Chinese Patent Application App. No. 201810134049.4, filed on Feb. 9, 2018, Chinese Patent Application App. No. 201810496766.1, filed on May 22, 2018, Chinese Patent Application App. No. 201810496216.X, filed on May 22, 2018, and Chinese Patent Application App. No. 201811188443.2, filed on Oct. 12, 2018. The entire contents of the foregoing are incorporated herein by reference.

TECHNICAL FIELD

This disclosure relates to genetically modified animal expressing human or chimeric (e.g., humanized) PD-1, and methods of use thereof.

BACKGROUND

The immune system has developed multiple mechanisms to prevent deleterious activation of immune cells. One such mechanism is the intricate balance between positive and negative costimulatory signals delivered to immune cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human PD-1 or chimeric PD-1. The animal model can express human PD-1 or chimeric PD-1 (e.g., humanized PD-1) protein in its body. It can be used in the studies on the function of PD-1 gene, and can be used in the screening and evaluation of anti-human PD-1 antibodies. In addition, the animal models prepared by the methods described herein can be used in drug screening, pharmacodynamics studies, treatments for immune-related diseases (e.g., autoimmune disease), and cancer therapy for human PD-1 target sites; they can also be used to facilitate the development and design of new drugs, and save time and cost. In summary, this disclosure provides a powerful tool for studying the function of PD-1 protein and a platform for screening cancer drugs.

In one aspect, the disclosure provides a genetically-modified, non-human animal whose genome comprises at least one chromosome comprising a sequence encoding a human or chimeric PD-1.

In some embodiments, the sequence encoding the human or chimeric PD-1 is operably linked to an endogenous regulatory element (e.g., a promoter) at the endogenous PD-1 gene locus in the at least one chromosome.

In some embodiments, the sequence encoding a human or chimeric PD-1 comprises a sequence encoding an amino acid sequence that is at least 70%, 75%, 80%, 85%, 90%, 95%, 99%, or 100% identical to human PD-1 (NP_005009.2 (SEQ ID NO: 35)).

In some embodiments, the sequence encoding a human or chimeric PD-1 comprises a sequence encoding an amino acid sequence that is at least 70%, 75%, 80%, 85%, 90%, 95%, 99%, or 100% identical to SEQ ID NO: 33.

In some embodiments, the sequence encoding a human or chimeric PD-1 is operably linked to a Woodchuck Hepatitis Virus (WHP) Posttranscriptional Regulatory Element. In some embodiments, the sequence encoding a human or chimeric PD-1 is operably linked to a polyA (polyadenylation) signal sequence.

In some embodiments, the animal is a mammal, e.g., a monkey, a rodent. In some embodiments, the rodent is a mouse or a rat.

In some embodiments, the animal does not express endogenous PD-1. In some embodiments, the animal has one or more cells expressing human or chimeric PD-1.

In some embodiments, the animal has one or more cells expressing human or chimeric PD-1, and human PD-L1 or human PD-L2 can bind to the expressed human or chimeric PD-1.

In some embodiments, the animal has one or more cells expressing human or chimeric PD-1, and endogenous PD-L1 or endogenous PD-L2 can bind to the expressed human or chimeric PD-1.

In one aspect, the disclosure provides a genetically-modified, non-human animal, wherein the genome of the animal comprises a replacement of a sequence encoding a region of endogenous PD-1 with a sequence encoding a human PD-1 or a chimeric PD-1 at an endogenous PD-1 gene locus.

In some embodiments, the sequence encoding the human PD-1 or the chimeric PD-1 is operably linked to an endogenous regulatory element at the endogenous PD-1 locus, and one or more cells of the animal express the human PD-1 or the chimeric PD-1.

In some embodiments, the sequence further comprises a Woodchuck Hepatitis Virus (WHP) Posttranscriptional Regulatory Element, and/or a polyA (polyadenylation) signal sequence.

In some embodiments, the animal does not express endogenous PD-1. In some embodiments, the replaced locus is located after start codon (ATG) at the endogenous PD-1 locus.

In some embodiments, the animal has one or more cells expressing a chimeric PD-1 having an extracellular region, a transmembrane region, and a cytoplasmic region, wherein the extracellular region comprises a sequence that is at least 50%, 60%, 70%, 80%, 90%, 95%, or 99% identical to the extracellular region of human PD-1.

In some embodiments, the extracellular region of the chimeric PD-1 has a sequence that has at least 10, 20, 30, 40, 50, 60, 70, 80, 90, or 100 contiguous amino acids that are identical to a contiguous sequence present in the extracellular region of human PD-1.

In some embodiments, the animal is a mouse, and the replaced region is exon 1 of the endogenous mouse PD-1 gene.

In some embodiments, the animal is heterozygous with respect to the replacement at the endogenous PD-1 gene locus. In some embodiments, the animal is homozygous with respect to the replacement at the endogenous PD-1 gene locus.

In one aspect, the disclosure provides methods for making a genetically-modified, non-human animal. In some embodiments, the methods involve replacing in at least one cell of the animal, at an endogenous PD-1 gene locus, a sequence encoding a region of an endogenous PD-1 with a sequence comprising at least one exon of human PD-1 gene.

In some embodiments, the methods involve inserting in at least one cell of the animal, at an endogenous PD-1 gene locus, a sequence comprising at least one exon of human PD-1 gene.

In some embodiments, the sequence comprising at least one exon of human PD-1 gene comprises exon 1, exon 2, exon 3, exon 4, and/or exon 5, or a part thereof, of a human PD-1 gene.

In some embodiments, the sequence comprising at least one exon of human PD-1 gene comprises exon 1, exon 2, and/or exon 3, or a part thereof, of a human PD-1 gene.

In some embodiments, the sequence comprising at least one exon of human PD-1 gene encodes at least amino acids 1-167 of SEQ ID NO: 35.

In some embodiments, the sequence comprising at least one exon of human PD-1 gene encodes a sequence that is at least 80%, 85%, 90%, 95% or 99% identical to SEQ ID NO: 33 or 35.

In some embodiments, the animal is a mouse, and the endogenous PD-1 locus is exon 1, exon 2, exon 3, exon 4, and/or exon 5 of the mouse PD-1 gene.

In some embodiments, the region is located in exon 1 of the mouse PD-1 gene.

In one aspect, the disclosure provides a non-human animal comprising at least one cell comprising a nucleotide sequence encoding a chimeric PD-1 polypeptide, wherein the chimeric PD-1 polypeptide comprises at least 50 contiguous amino acid residues that are identical to the corresponding contiguous amino acid sequence of a human PD-1, wherein the animal expresses the chimeric PD-1.

In some embodiments, the chimeric PD-1 polypeptide has at least 50 contiguous amino acid residues that are identical to the corresponding contiguous amino acid sequence of a human PD-1 extracellular region.

In some embodiments, the chimeric PD-1 polypeptide comprises a sequence that is at least 80%, 85%, 90%, 95%, or 99% identical to amino acids 1-167 of SEQ ID NO: 35. In some embodiments, the chimeric PD-1 polypeptide comprises a sequence that is at least 80%, 85%, 90%, 95%, or 99% identical to amino acids 168-288 of SEQ ID NO: 2.

In some embodiments, the nucleotide sequence is operably linked to an endogenous PD-1 regulatory element of the animal.

In some embodiments, the chimeric PD-1 polypeptide comprises an endogenous PD-1 transmembrane region and/or an endogenous PD-1 cytoplasmic region.

In some embodiments, the nucleotide sequence is integrated to an endogenous PD-1 gene locus of the animal.

In some embodiments, the chimeric PD-1 has at least one mouse PD-1 activity and/or at least one human PD-1 activity.

In one aspect, the disclosure provides methods of making a genetically-modified mouse cell that expresses a human PD-1 or a chimeric PD-1. The methods involve replacing at an endogenous mouse PD-1 gene locus, a nucleotide sequence encoding a region of mouse PD-1 with a nucleotide sequence encoding a human PD-1 or a chimeric PD-1, thereby generating a genetically-modified mouse cell that includes a nucleotide sequence that encodes the human PD-1 or the chimeric PD-1, wherein the mouse cell expresses the human PD-1 or the chimeric PD-1.

In some embodiments, the chimeric PD-1 comprises: an extracellular region of human PD-1 comprising a human signal peptide sequence; and a transmembrane and/or a cytoplasmic region of mouse PD-1.

In some embodiments, the nucleotide sequence encoding the human PD-1 or the chimeric PD-1 is operably linked to an endogenous PD-1 regulatory region, e.g., a promoter, and/or a Woodchuck Hepatitis Virus (WHP) Posttranscriptional Regulatory Element.

In some embodiments, the animal further comprises a sequence encoding an additional human or chimeric protein.

In some embodiments, the additional human or chimeric protein is cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (OX40).

In one aspect, the disclosure provides methods of determining effectiveness of an antibody for the treatment of cancer. The methods involve administering the antibody to the animal as described herein, wherein the animal has a tumor; and determining the inhibitory effects of the antibody to the tumor. In some embodiments, the antibody is an anti-PD-1 antibody or anti-PD-L1 antibody.

In some embodiments, the tumor comprises one or more cells that express PD-1 ligands. In some embodiments, the tumor comprises one or more cancer cells that are injected into the animal.

In some embodiments, determining the inhibitory effects of the antibody to the tumor comprises measuring the tumor volume in the animal.

In some embodiments, the tumor cells are melanoma cells, pancreatic carcinoma cells, mesothelioma cells, or solid tumor cells.

In one aspect, the disclosure provides methods of determining effectiveness of an anti-PD-1 antibody and an additional therapeutic agent for the treatment of a tumor. The methods involve administering the anti-PD-1 antibody and the additional therapeutic agent to the animal as described herein, wherein the animal has a tumor; and determining the inhibitory effects on the tumor.

In some embodiments, the animal further comprises a sequence encoding a human or chimeric CTLA4.

In some embodiments, the animal further comprises a sequence encoding a human or chimeric programmed death-ligand 1 (PD-L1).

In some embodiments, the additional therapeutic agent is an anti-PD-L1 antibody.

In some embodiments, the tumor comprises one or more tumor cells that express PD-L1 or PD-L2.

In some embodiments, the tumor is caused by injection of one or more cancer cells into the animal.

In some embodiments, determining the inhibitory effects of the treatment involves measuring the tumor volume in the animal.

In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure provides a protein comprising an amino acid sequence, wherein the amino acid sequence is one of the following:
(a) an amino acid sequence set forth in SEQ ID NO: 33;
(b) an amino acid sequence that is at least 90% identical to SEQ ID NO: 33;
(c) an amino acid sequence that is at least 91%, 92%, 93%, 94%, 95%, 96%, 97%, 98%, or 99% identical to SEQ ID NO: 33;
(d) an amino acid sequence that is different from the amino acid sequence set forth in SEQ ID NO: 33 by no more than 10, 9, 8, 7, 6, 5, 4, 3, 2 or 1 amino acid; and
(e) an amino acid sequence that comprises a substitution, a deletion and/or insertion of one, two, three, four, five or more amino acids to the amino acid sequence set forth in SEQ ID NO: 33.

In one aspect, the disclosure provides a nucleic acid comprising a nucleotide sequence, wherein the nucleotide sequence is one of the following:
(a) a sequence that encodes the protein as described herein;
(b) SEQ ID NO: 3, SEQ ID NO: 9 or SEQ ID NO: 10;
(c) SEQ ID NO: 4, SEQ ID NO: 36 or SEQ ID NO: 39;
(d) a sequence that is at least 90% identical to SEQ ID NO: 3, SEQ ID NO: 9, SEQ ID NO: 10, SEQ ID NO: 4, SEQ ID NO: 36, or SEQ ID NO: 39;
(e) a sequence that is at least 91%, 92%, 93%, 94%, 95%, 96%, 97%, 98%, or 99% identical to SEQ ID NO: 3, SEQ ID NO: 9 or SEQ ID NO: 10; and
(f) a sequence that is at least 91%, 92%, 93%, 94%, 95%, 96%, 97%, 98%, or 99% identical to SEQ ID NO: 4, SEQ ID NO: 36 or SEQ ID NO: 39.

In one aspect, the disclosure provides a cell comprising the protein and/or the nucleic acid as described herein.

In some embodiments, the tumor comprises one or more cancer cells that are injected into the animal. In some embodiments, determining the inhibitory effects of the anti-PD-1 antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells. In some embodiments, the tumor cells are breast cancer cells, ovarian cancer cells, and/or solid tumor cells. In some embodiments, the tumor cells are lymphoma cells, colorectal cancer cells, or oropharyngeal cancer cells. In some embodiments, the animal has metastatic solid tumors, NSCLC, melanoma, lymphoma (e.g., non-Hodgkin lymphoma), colorectal cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to methods of determining effectiveness of an anti-PD-1 antibody for the treatment of various immune-related disorders, e.g., autoimmune diseases.

In another aspect, the disclosure also provides a genetically-modified, non-human animal whose genome comprise a disruption in the animal's endogenous PD-1 gene, wherein the disruption of the endogenous PD-1 gene comprises deletion of exon 1, exon 2, exon 3, exon 4, and/or exon 5, or part thereof of the endogenous PD-1 gene.

In some embodiments, the disruption of the endogenous PD-1 gene comprises deletion of one or more exons or part of exons selected from the group consisting of exon 1, exon 2, exon 3, exon 4, and exon 5 of the endogenous PD-1 gene.

In some embodiments, the disruption of the endogenous PD-1 gene further comprises deletion of one or more introns or part of introns selected from the group consisting of intron 1, intron 2, intron 3, and intron 4 of the endogenous PD-1 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous PD-1 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, and/or exon 5 (e.g., deletion of at least 100 nucleotides of exon 1).

In some embodiments, the mice described in the present disclosure can be mated with the mice containing other human or chimeric genes (e.g., chimeric PD-L1, chimeric PD-L2, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In another aspect, the disclosure further provides methods of determining toxicity of an agent (e.g., a PD-1 antagonist or agonist). The methods involve administering the agent to the animal as described herein; and determining weight change of the animal. In some embodiments, the method further involve performing a blood test (e.g., determining red blood cell count).

In one aspect, the disclosure relates to a targeting vector, including a) a DNA fragment homologous to the 5' end of a region to be altered (5' arm), which is selected from the PD-1 gene genomic DNAs in the length of 100 to 10,000 nucleotides; b) a desired/donor DNA sequence encoding a donor region or a protein (e.g., a human PD-1 or a chimeric PD-1); and c) a second DNA fragment homologous to the 3' end of the region to be altered (3' arm), which is selected from the PD-1 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000067.6; c) the DNA fragment homologous to the 3' end of the region to be altered (3' arm/receptor) is selected from the nucleotide sequences that have at least 90% homology to the NCBI accession number NC_000067.6.

In some embodiments, a) the DNA fragment homologous to the 5' end of a region to be altered (5' arm/receptor) is selected from the nucleotides from the position 94052491 to the position 94053890 of the NCBI accession number NC_000067.6; c) the DNA fragment homologous to the 3' end of the region to be altered (3' arm/receptor) is selected from the nucleotides from the position 94051015 to the position 94052414 of the NCBI accession number NC_000067.6.

In some embodiments, a length of the selected genomic nucleotide sequence is more than 3 kb, 3.5 kb, 4 kb, 4.5 kb, 5 kb, 5.5 kb, or 6 kb. In some embodiments, the region to be altered is exon 1, exon 2, exon 3, exon 4, and/or exon 5 of mouse PD-1 gene.

In some embodiments, the sequence of the 5' arm is shown in SEQ ID NO: 7. In some embodiments, the sequence of the 3' arm is shown in SEQ ID NO: 8.

In some embodiments, the targeting vector further includes a selectable gene marker.

In some embodiments, the target region is derived from human. In some embodiments, the target region is a part or entirety of the nucleotide sequence of a human PD-1 or a chimeric PD-1. In some embodiments, the nucleotide sequence is shown as one or more of exon 1, exon 2, exon 3, exon 4, and exon 5 of the human PD-1.

In some embodiments, the nucleotide sequence of the human PD-1 encodes the human PD-1 protein with the NCBI accession number NP_005009.2 (SEQ ID NO: 35).

The disclosure also relates to a cell including the targeting vector as described herein.

The disclosure also relates to a method for establishing a genetically-modified non-human animal expressing two human or chimeric (e.g., humanized) genes. The method includes the steps of
  (a) using the method for establishing a PD-1 gene humanized animal model to obtain a PD-1 gene genetically modified humanized mouse;
  (b) mating the PD-1 gene genetically modified humanized mouse obtained in step (a) with another humanized mouse, and then screening to obtain a double humanized mouse model.

In some embodiments, in step (b), the PD-1 gene genetically modified humanized mouse obtained in step (a) is mated with a PD-L1 humanized mouse to obtain a PD-1 and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the rodent is a mouse or a rat.

In some embodiments, the non-human mammal expresses a protein encoded by a human PD-1 gene or a chimeric PD-1 gene.

The disclosure also relates to an offspring of the non-human mammal.

In another aspect, the disclosure relates to a tumor bearing non-human mammal model, wherein the non-human mammal model is obtained through the methods as described herein.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a PD-1 amino acid sequence of a humanized mouse, wherein the amino acid sequence is selected from the group consisting of:
  a) an amino acid sequence shown in SEQ ID NO: 33;
  b) an amino acid sequence having a homology of at least 90% with the amino acid sequence shown in SEQ ID NO: 33;
  c) an amino acid sequence encoded by a nucleic acid sequence, wherein the nucleic acid sequence is able to hybridize to a nucleotide sequence encoding the amino acid shown in SEQ ID NO: 33 under a low stringency condition or a strict stringency condition;
  d) an amino acid sequence having a homology of at least 90%, 91%, 92%, 93%, 94%, 95%, 96%, 97%, 98%, or at least 99% with the amino acid sequence shown in SEQ ID NO: 33;
  e) an amino acid sequence that is different from the amino acid sequence shown in SEQ ID NO: 33 by no more than 10, 9, 8, 7, 6, 5, 4, 3, 2 or no more than 1 amino acid; or
  f) an amino acid sequence that comprises a substitution, a deletion and/or insertion of one or more amino acids to the amino acid sequence shown in SEQ ID NO: 33.

The disclosure also relates to a PD-1 nucleic acid sequence of a humanized mouse, wherein the nucleic acid sequence is selected from the group consisting of:
  a) a nucleic acid sequence that encodes the PD-1 amino acid sequence of a humanized mouse;
  b) a nucleic acid sequence that is set forth in SEQ ID NO: 3, SEQ ID NO: 4, SEQ ID NO: 9, SEQ ID NO: 10, SEQ ID NO: 36, or SEQ ID NO: 39;
  c) a nucleic acid sequence that can hybridize to the nucleotide sequence as shown in SEQ ID NO: 3, SEQ ID NO: 4, SEQ ID NO: 9, SEQ ID NO: 10, SEQ ID NO: 36, or SEQ ID NO: 39 under a low stringency condition or a strict stringency condition;
  d) a nucleic acid sequence that has a homology of at least 90%, 91%, 92%, 93%, 94%, 95%, 96%, 97%, 98%, or at least 99% with the nucleotide sequence as shown in SEQ ID NO: 3, SEQ ID NO: 4, SEQ ID NO: 9, SEQ ID NO: 10, SEQ ID NO: 36, or SEQ ID NO: 39;
  f) a nucleic acid sequence that encodes an amino acid sequence, wherein the amino acid sequence has a homology of at least 90% with the amino acid sequence shown in SEQ ID NO: 33;
  g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 33;
  h) a nucleic acid sequence that encodes an amino acid sequence, wherein the amino acid sequence is different from the amino acid sequence shown in SEQ ID NO: 33 by no more than 10, 9, 8, 7, 6, 5, 4, 3, 2 or no more than 1 amino acid; and/or
  i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 33.

The disclosure further relates to a PD-1 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the PD-1 gene function, human PD-1 antibodies, human PD-L1 antibodies, the drugs or efficacies for human PD-1 or PD-L1 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 14:
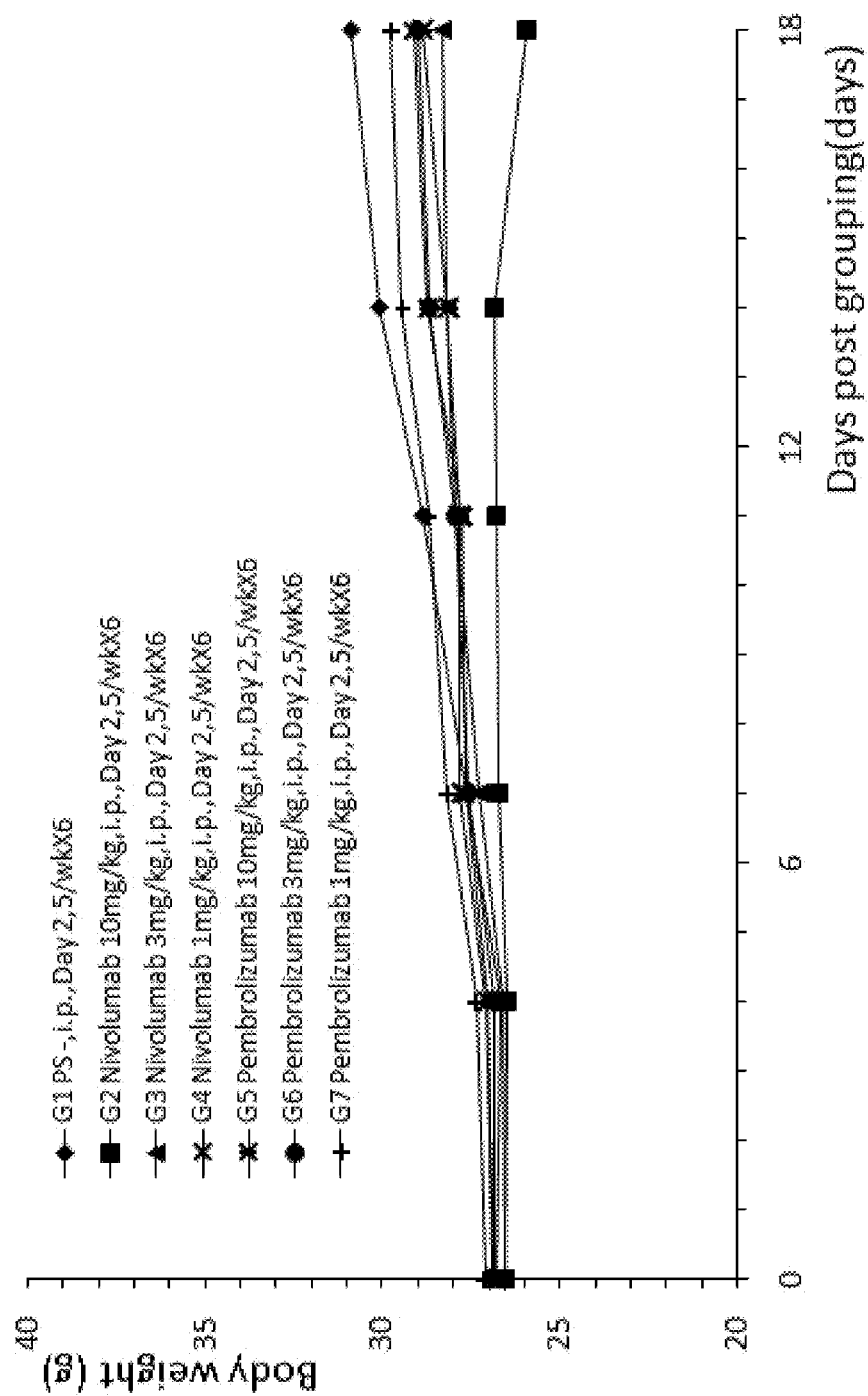

FIG. 14. The average weight of the different groups of humanized PD-1 homozygous mice (huPD-1 version) that were injected with mouse colon cancer cells MC38, and were treated with 2 different anti-human PD-1 antibodies (Nivolumab and Pembrolizumab) at different dosages (10 mg/kg, 3 mg/kg or 1 mg/kg).

Figure 15:
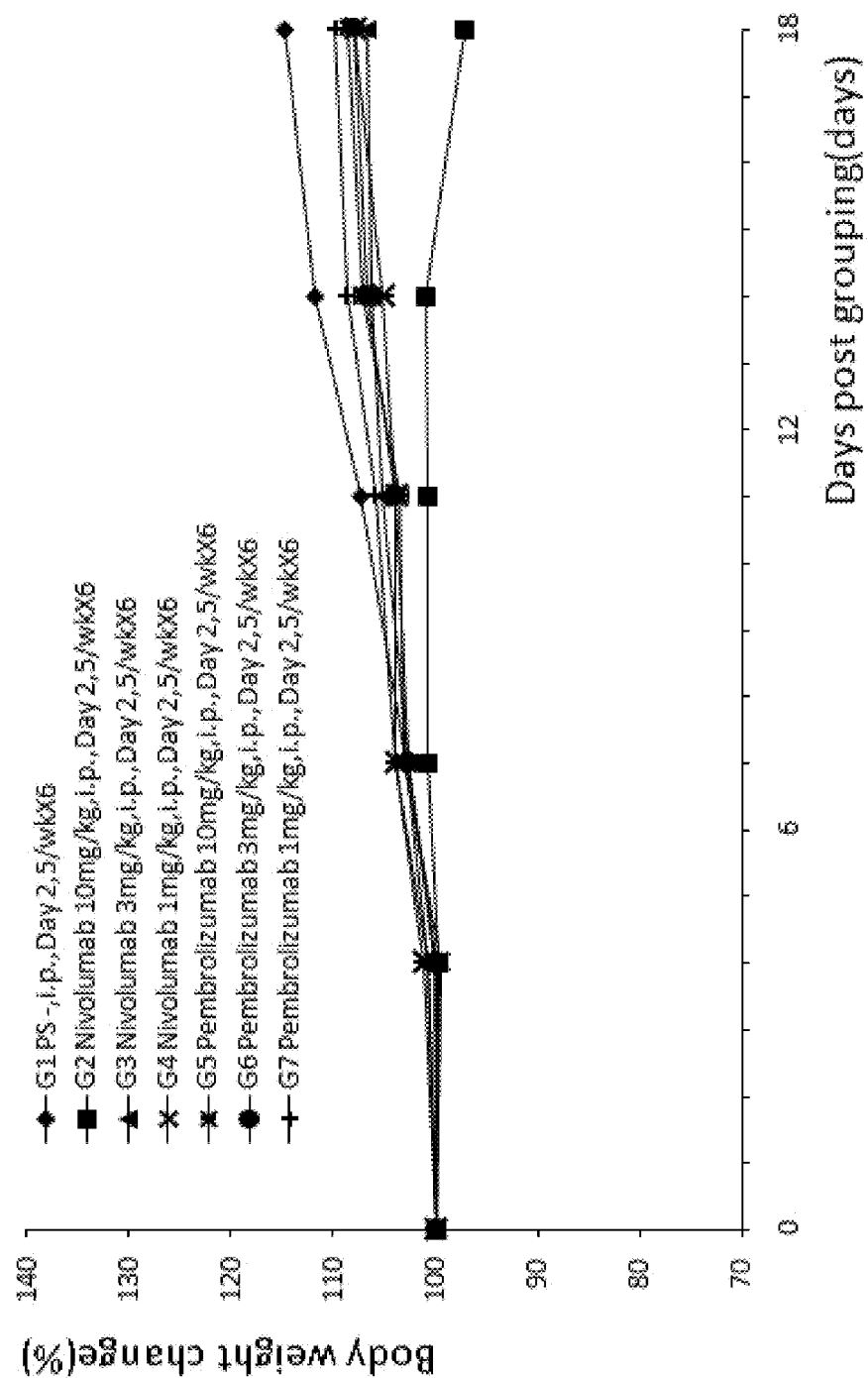

FIG. 15. The percentage change of average weight of the different groups of humanized PD-1 homozygous mice (huPD-1 version) that were injected with mouse colon cancer cells MC38, and were treated with 2 different anti-human PD-1 antibodies (Nivolumab and Pembrolizumab) at different dosages (10 mg/kg, 3 mg/kg or 1 mg/kg).

Figure 16:
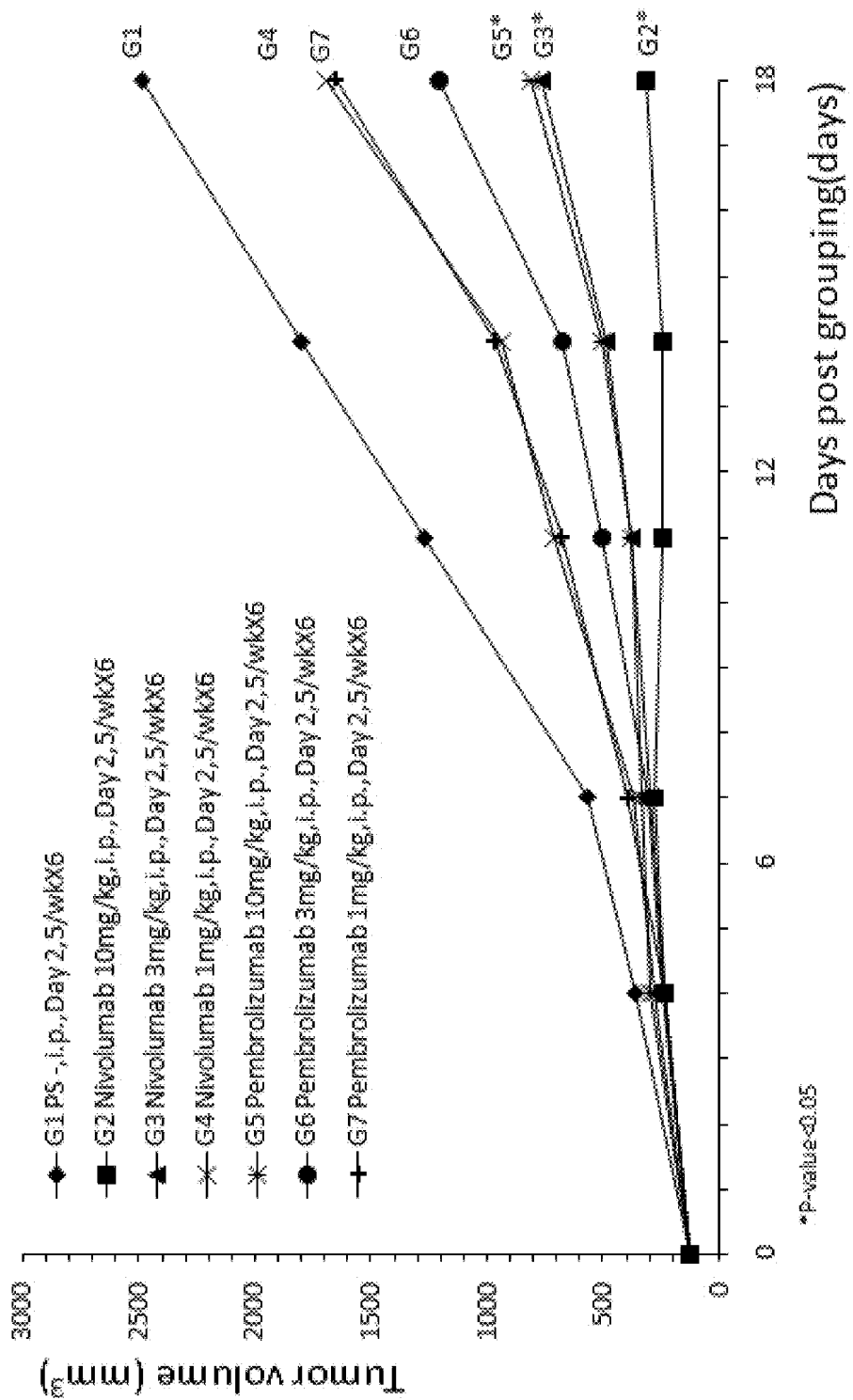

FIG. 16. The average tumor volume in the different groups of humanized PD-1 homozygous mice (huPD-1 version) that were injected with mouse colon cancer cells MC38, and were treated with 2 different anti-human PD-1 antibodies (Nivolumab and Pembrolizumab) at different dosages (10 mg/kg, 3 mg/kg or 1 mg/kg).

Figure 17:
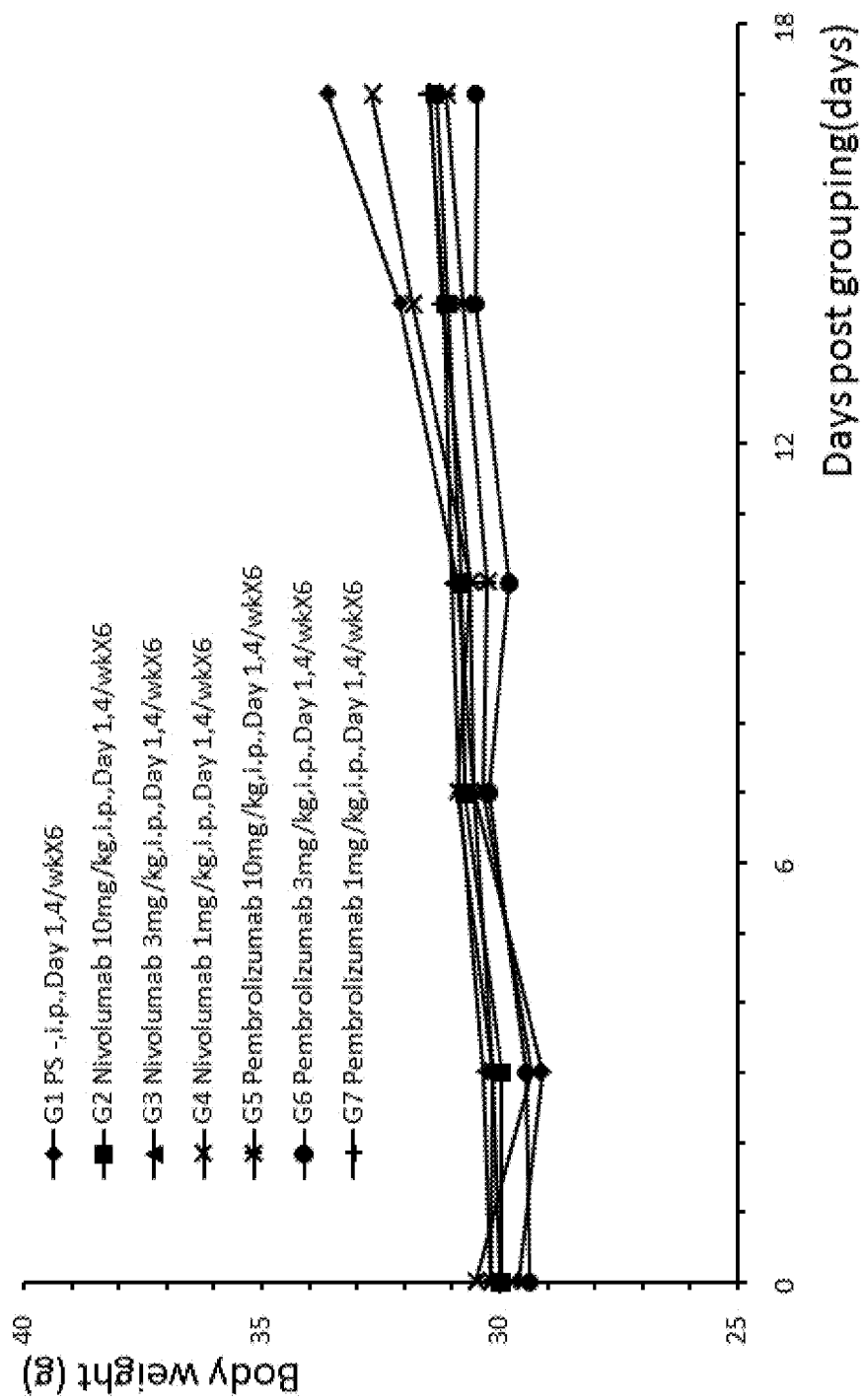

FIG. 17. The average weight of the different groups of humanized PD-1 homozygous mice (chiPD-1 version) that were injected with mouse colon cancer cells MC38, and were treated with 2 different anti-human PD-1 antibodies (Nivolumab and Pembrolizumab) at different dosages (10 mg/kg, 3 mg/kg or 1 mg/kg).

Figure 18:
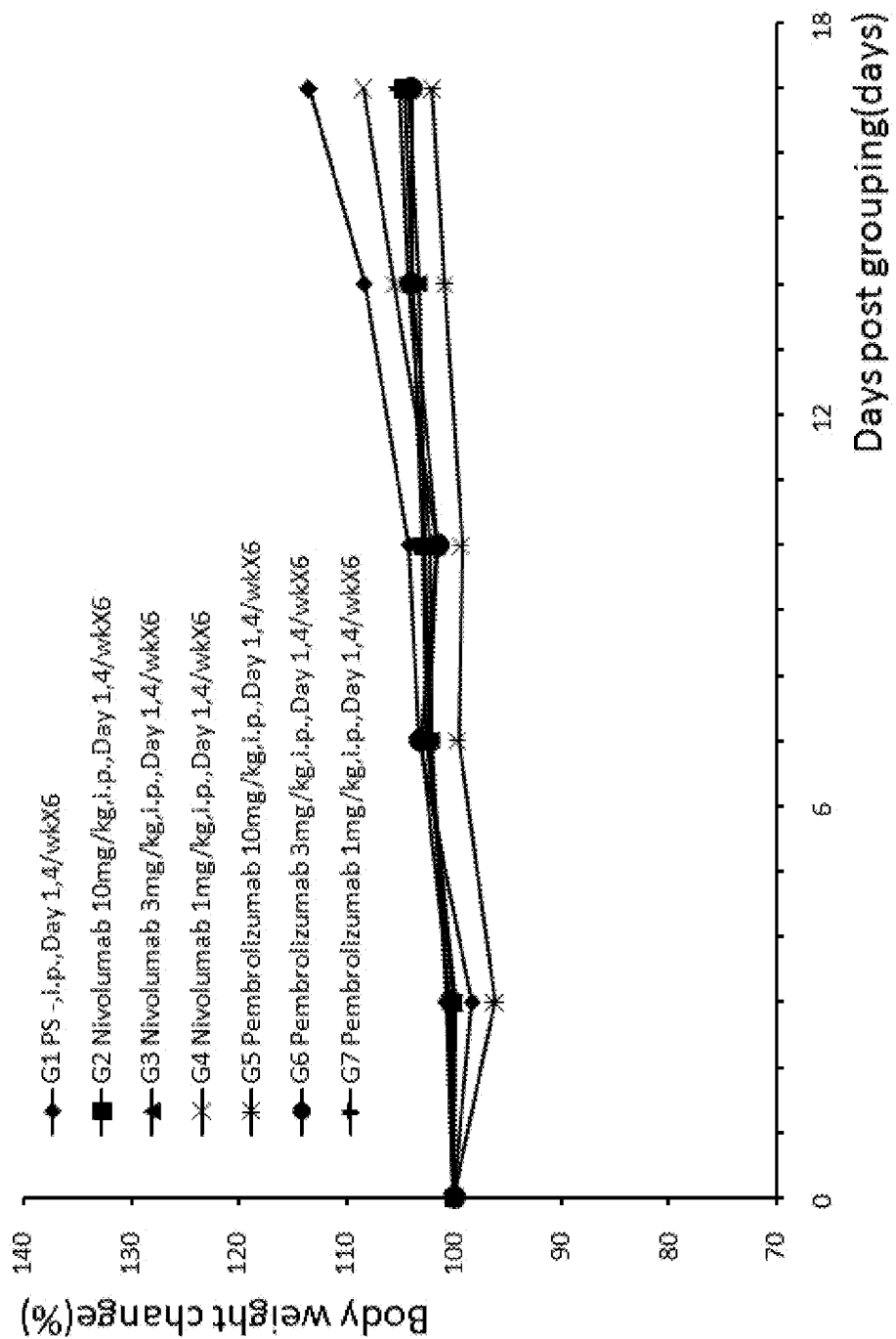

FIG. 18. The percentage change of average weight of the different groups of humanized PD-1 homozygous mice (chiPD-1 version) that were injected with mouse colon cancer cells MC38, and were treated with 2 different anti-human PD-1 antibodies (Nivolumab and Pembrolizumab) at different dosages (10 mg/kg, 3 mg/kg or 1 mg/kg).

Figure 19:
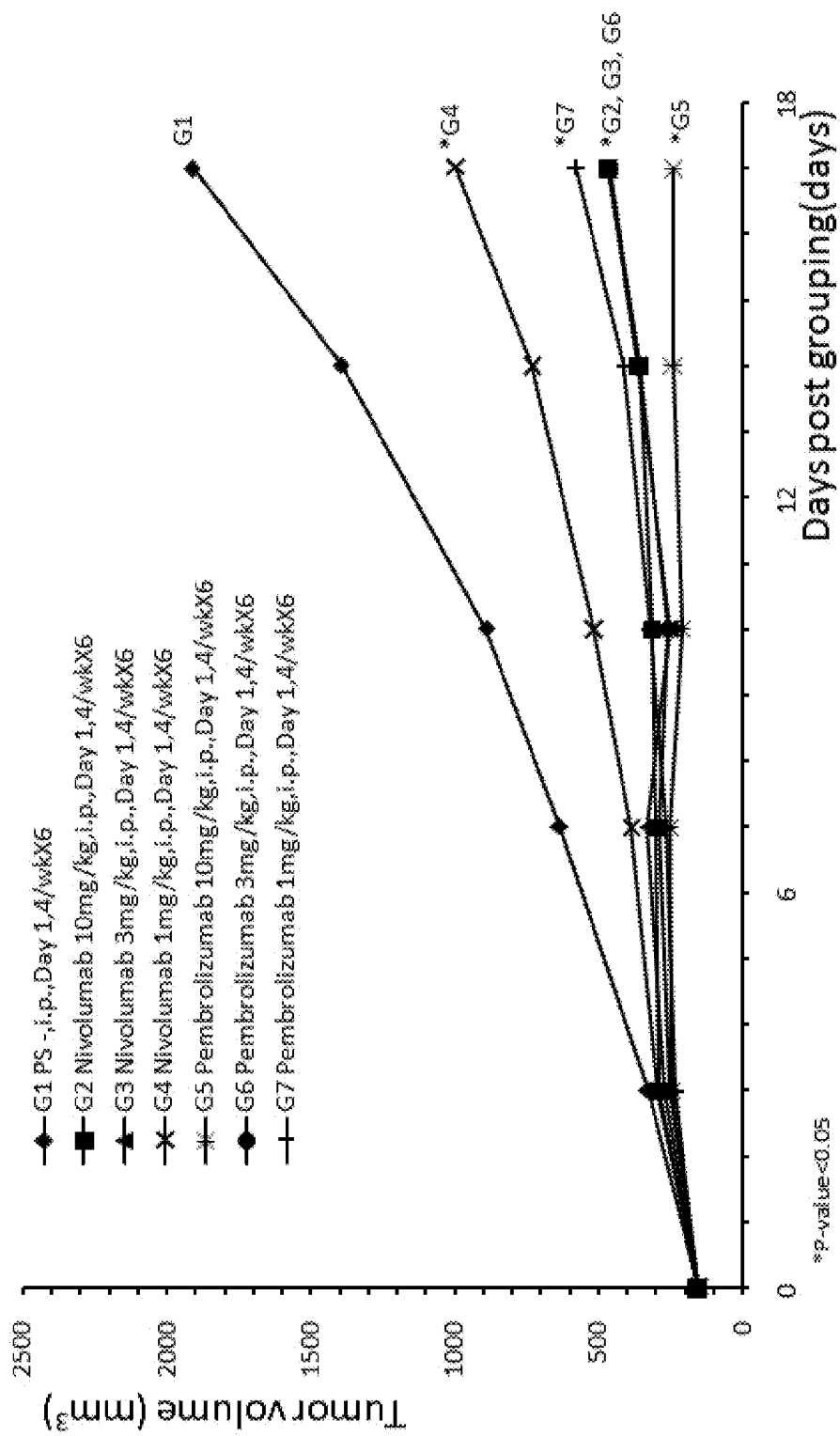

FIG. 19. The average tumor volume in the different groups of humanized PD-1 homozygous mice (chiPD-1 version) that were injected with mouse colon cancer cells MC38, and were treated with 2 different anti-human PD-1 antibodies (Nivolumab and Pembrolizumab) at different dosages (10 mg/kg, 3 mg/kg or 1 mg/kg).

FIG. 20 shows the alignment between mouse PD-1 amino acid sequence (NP_032824.1; SEQ ID NO: 2) and human PD-1 amino acid sequence (NP_005009.2; SEQ ID NO: 35).

DETAILED DESCRIPTION

This disclosure relates to transgenic non-human animal with human or chimeric (e.g., humanized) PD-1 (Programmed Cell Death Protein 1; also known as CD279), and methods of use thereof.

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

Experimental animal models are an indispensable research tool for studying the effects of these antibodies (e.g., PD-1 antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullis et al U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

PD-1

PD-1 (Programmed cell death protein 1 or CD279) is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells).

PD-1 is mainly expressed on the surfaces of T cells and primary B cells; two ligands of PD-1 (PD-L1 and PD-L2) are widely expressed in antigen-presenting cells (APCs). The interaction of PD-1 with its ligands plays an important role in the negative regulation of the immune response. Inhibition the binding between PD-1 and its ligand can make the tumor cells exposed to the killing effect of the immune system, and thus can reach the effect of killing tumor tissues and treating cancers.

PD-L1 is expressed on the neoplastic cells of many different cancers. By binding to PD-1 on T-cells leading to its inhibition, PD-L1 expression is a major mechanism by which tumor cells can evade immune attack. PD-L1 overexpression may conceptually be due to 2 mechanisms, intrinsic and adaptive. Intrinsic expression of PD-L1 on cancer cells is related to cellular/genetic aberrations in these neoplastic cells. Activation of cellular signaling including the AKT and STAT pathways results in increased PD-L1 expression. In primary mediastinal B-cell lymphomas, gene fusion of the MHC class II transactivator (CIITA) with PD-L1 or PD-L2 occurs, resulting in overexpression of these proteins. Amplification of chromosome 9p23-24, where PD-L1 and PD-L2 are located, leads to increased expression of both proteins in classical Hodgkin lymphoma. Adaptive mechanisms are related to induction of PD-L1 expression in the tumor microenvironment. PD-L1 can be induced on neoplastic cells in response to interferon γ. In microsatellite instability colon cancer, PD-L1 is mainly expressed on myeloid cells in the tumors, which then suppress cytotoxic T-cell function.

The use of PD-1 blockade to enhance anti-tumor immunity originated from observations in chronic infection models, where preventing PD-1 interactions reversed T-cell exhaustion. Similarly, blockade of PD-1 prevents T-cell PD-1/tumor cell PD-L1 or T-cell PD-1/tumor cell PD-L2 interaction, leading to restoration of T-cell mediated anti-tumor immunity.

A detailed description of PD-1, and the use of anti-PD-1 antibodies to treat cancers are described, e.g., in Topalian, Suzanne L., et al. "Safety, activity, and immune correlates of anti-PD-1 antibody in cancer." New England Journal of Medicine 366.26 (2012): 2443-2454; Hirano, Fumiya, et al. "Blockade of B7-H1 and PD-1 by monoclonal antibodies potentiates cancer therapeutic immunity." Cancer research 65.3 (2005): 1089-1096; Raedler, Lisa A. "Keytruda (pembrolizumab): first PD-1 inhibitor approved for previously treated unresectable or metastatic melanoma." American health & drug benefits 8. Spec Feature (2015): 96; Kwok, Gerry, et al. "Pembrolizumab (Keytruda)." (2016): 2777-2789; US 20170247454; U.S. Pat. Nos. 9,834,606 B; and 8,728,474; each of which is incorporated by reference in its entirety.

In human genomes, PD-1 gene (Gene ID: 5133) locus has five exons, exon 1, exon 2, exon 3, exon 4, and exon 5. The PD-1 protein also has an extracellular region, a transmembrane region, and a cytoplasmic region, and the signal peptide is located at the extracellular region of PD-1. The nucleotide sequence for human PD-1 mRNA is NM_005018.2 (SEQ ID NO: 34), and the amino acid sequence for human PD-1 is NP_005009.2 (SEQ ID NO: 35). The location for each exon and each region in human PD-1 nucleotide sequence and amino acid sequence is listed below:

TABLE 1

| Human PD-1 (approximate location) | NM_005018.2 2115 bp (SEQ ID NO: 34) | NP_005009.2 288 aa (SEQ ID NO: 35) |
|---|---|---|
| Exon 1 | 1-144 | 1-25 |
| Exon 2 | 145-504 | 26-145 |
| Exon 3 | 505-660 | 146-197 |
| Exon 4 | 661-695 | 198-209 |
| Exon 5 | 696-2112 | 210-288 |
| Signal peptide | 69-128 | 1-20 |
| Extracellular region (excluding signal peptide region) | 129-578 | 21-170 |
| Transmembrane region | 579-641 | 171-191 |
| Cytoplasmic region | 642-935 | 192-288 |
| Region in an example of chimeric PD-1 | 69-569 | 1-167 |

Figure 1:
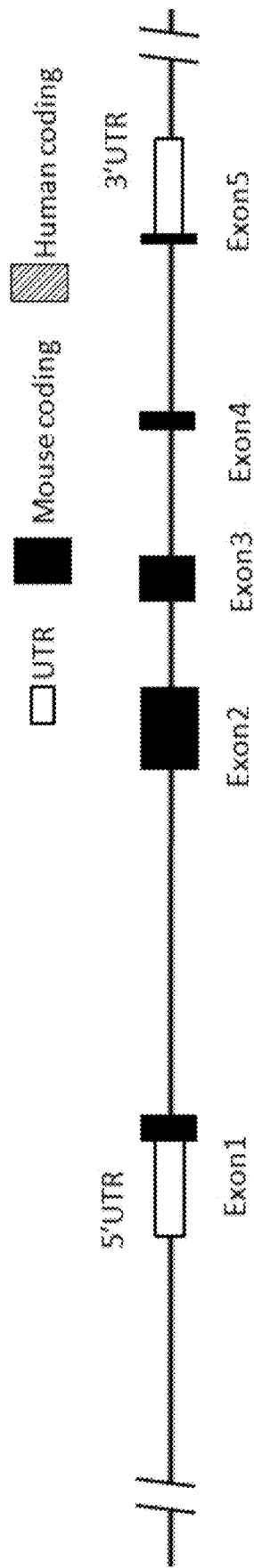
FIG. 1 is a schematic diagram showing a map of endogenous PD-1 gene in mice.

In mice, PD-1 gene locus has five exons, exon 1, exon 2, exon 3, exon 4, and exon 5 (FIG. 1). The mouse PD-1 protein also has an extracellular region, a transmembrane region, and a cytoplasmic region, and the signal peptide is located at the extracellular region of PD-1. The nucleotide sequence for mouse PD-1 mRNA is NM_008798.2 (SEQ ID NO: 1), the amino acid sequence for mouse PD-1 is NP_032824.1 (SEQ ID NO: 2). The location for each exon and each region in the mouse PD-1 nucleotide sequence and amino acid sequence is listed below:

TABLE 2

| Mouse PD-1 (approximate location) | NM_008798.2 1972 bp (SEQ ID NO: 1) | NP_032824.1 288 aa (SEQ ID NO: 2) |
|---|---|---|
| Exon 1 | 1-139 | 1-25 |
| Exon 2 | 140-499 | 26-145 |
| Exon 3 | 500-661 | 146-199 |
| Exon 4 | 662-696 | 200-211 |
| Exon 5 | 697-1932 | 212-288 |
| Signal peptide | 64-123 | 1-20 |
| Extracellular region (excluding signal peptide region) | 124-570 | 21-169 |
| Transmembrane region | 571-633 | 170-190 |
| Cytoplasmic region | 634-930 | 191-288 |
| Region in an example of chimeric PD-1 | 565-930 | 168-288 |

The mouse PD-1 gene (Gene ID: 18566) is located in Chromosome 1 of the mouse genome, which is located from 94038305-94052553, of NC_000067.6 (GRCm38.p4 (GCF_000001635.24)). The 5'-UTR is from 94052553 to 94052491, exon 1 is from 94052490 to 94052415, the first intron is from 94052414 to 94041516, exon 2 is from 94041515 to 94041156, the second intron is from 94041155 to 94040872, exon 3 is from 94040871 to 94040710, the third intron is from 94040709 to 94040127, exon 4 is from 94040126 to 94040092, the fourth intron is from 94040091 to 94039539, exon 5 is from 94039538 to 94039305, the 3'-UTR is from 94039304 to 94038305, based on transcript NM_008798.2. All relevant information for mouse PD-1 locus can be found in the NCBI website with Gene ID: 18566, which is incorporated by reference herein in its entirety.

FIG. 20 shows the alignment between mouse PD-1 amino acid sequence (NP_032824.1; SEQ ID NO: 2) and human PD-1 amino acid sequence (NP_005009.2; SEQ ID NO: 35). Thus, the corresponding amino acid residue or region between human and mouse PD-1 can be found in FIG. 20.

PD-1 genes, proteins, and locus of the other species are also known in the art. For example, the gene ID for PD-1 in

*Rattus norvegicus* is 301626, the gene ID for PD-1 in *Macaca mulatta* (Rhesus monkey) is 100135775, the gene ID for PD-1 in *Canis lupus familiaris* (dog) is 486213, and the gene ID for PD-1 in *Bos taurus* (cattle) is 613842. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) PD-1 nucleotide sequence and/or amino acid sequences. In some embodiments, the entire sequence of mouse exon 1, exon 2, exon 3, exon 4, exon 5, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, signal peptide, extracellular region, transmembrane region, or cytoplasmic region. In some embodiments, a region, a portion, or the entire sequence of mouse exon 1, exon 2, exon 3, exon 4, and/or exon 5 (e.g., exon 1, exon 2, and/or exon 3) are replaced by the human exon 1, exon 2, exon 3, exon 4, and/or exon 5 (e.g., exon 1, exon 2, and/or exon 3) sequence.

In some embodiments, the present disclosure also provides a chimeric (e.g., humanized) PD-1 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse PD-1 mRNA sequence (e.g., SEQ ID NO: 1), mouse PD-1 amino acid sequence (e.g., SEQ ID NO: 2), or a portion thereof (e.g., exon 1, exon 2, exon 3, exon 4, and exon 5); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human PD-1 mRNA sequence (e.g., SEQ ID NO: 34), human PD-1 amino acid sequence (e.g., SEQ ID NO: 35), or a portion thereof (e.g., exon 1, exon 2, exon 3, exon 4, and exon 5).

In some embodiments, the chimeric PD-1 sequence encodes amino acids 168-288 of mouse PD-1 (SEQ ID NO: 2). In some embodiments, the chimeric PD-1 sequence encodes amino acids 1-167 of human PD-1 (SEQ ID NO: 35).

In some embodiments, the nucleic acids as described herein are operably linked to a promotor or regulatory element, e.g., an endogenous mouse PD-1 promotor, an inducible promoter, an enhancer, and/or mouse or human regulatory elements.

In some embodiments, the nucleic acids as described herein are operably linked to a Woodchuck Hepatitis Virus (WHP) Posttranscriptional Regulatory Element (WPRE) and/or a polyA (polyadenylation) signal sequence. The WPRE element is a DNA sequence that, when transcribed, creates a tertiary structure enhancing expression. The sequence can be used to increase expression of genes delivered by viral vectors. WPRE is a tripartite regulatory element with gamma, alpha, and beta components. The sequence for the alpha component is shown below:

```
                                         (SEQ ID NO: 40)
GCCACGGCGGAACTCATCGCCGCCTGCCTTGCCCGCTGCTGGACAGGGGC
TCGGCTGTTGGGCACTGACAATTCCGTGGT
```

When used alone without the gamma and beta WPRE components, the alpha component is only 9% as active as the full tripartite WPRE. The full tripartite WPRE sequence is set forth in SEQ ID NO: 5. In some embodiments, the WPRE sequence has a sequence that is at least 70%, 80%, 90%, or 95% identical to SEQ ID NO: 5 or SEQ ID NO: 40.

In some embodiments, the polyA (polyadenylation) signal sequence has a sequence that is at least 70%, 80%, 90%, or 95% identical to SEQ ID NO: 6.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse PD-1 nucleotide sequence (e.g., exon 1, exon 2, exon 3, exon 4, exon 5, or NM_008798.2 (SEQ ID NO: 1)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse PD-1 nucleotide sequence (e.g., exon 1, exon 2, exon 3, exon 4, exon 5, or NM_008798.2 (SEQ ID NO: 1)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human PD-1 nucleotide sequence (e.g., exon 1, exon 2, exon 3, exon 4, exon 5, or NM_005018.2 (SEQ ID NO: 34)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human PD-1 nucleotide sequence (e.g., exon 1, exon 2, exon 3, exon 4, exon 5, or NM_005018.2 (SEQ ID NO: 34)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse PD-1 amino acid sequence (e.g., exon 1, exon 2, exon 3, exon 4, exon 5, or NP_032824.1 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse PD-1 amino acid sequence (e.g., exon 1, exon 2, exon 3, exon 4, exon 5, or NP_032824.1 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human PD-1 amino acid sequence (e.g., exon 1, exon 2, exon 3, exon 4, exon 5, or NP_005009.2 (SEQ ID NO: 35)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human PD-1 amino acid sequence (e.g., exon 1, exon 2, exon 3, exon 4, exon 5, or NP_005009.2 (SEQ ID NO: 35)).

The present disclosure also provides a humanized PD-1 mouse amino acid sequence, wherein the amino acid sequence is selected from the group consisting of:
a) an amino acid sequence shown in SEQ ID NO: 33;
b) an amino acid sequence having a homology of at least 90% with or at least 90% identical to the amino acid sequence shown in SEQ ID NO: 33 or SEQ ID NO: 35;
c) an amino acid sequence encoded by a nucleic acid sequence, wherein the nucleic acid sequence is able to hybridize to a nucleotide sequence encoding the amino acid shown in SEQ ID NO: 33 or SEQ ID NO: 35 under a low stringency condition or a strict stringency condition;
d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 33 or SEQ ID NO: 35;
e) an amino acid sequence that is different from the amino acid sequence shown in SEQ ID NO: 33 or SEQ ID NO: 35 by no more than 10, 9, 8, 7, 6, 5, 4, 3, 2 or no more than 1 amino acid; or
f) an amino acid sequence that comprises a substitution, a deletion and/or insertion of one or more amino acids to the amino acid sequence shown in SEQ ID NO: 33 or SEQ ID NO: 35.

The present disclosure also relates to a PD-1 nucleic acid (e.g., DNA or RNA) sequence, wherein the nucleic acid sequence can be selected from the group consisting of:
a) a nucleic acid sequence as shown in SEQ ID NO: 3, SEQ ID NO: 4, SEQ ID NO: 9, SEQ ID NO: 10, SEQ ID NO: 36, or SEQ ID NO: 39, or a nucleic acid sequence encoding a homologous PD-1 amino acid sequence of a humanized mouse;
b) a nucleic acid sequence that is shown in SEQ ID NO: 3, SEQ ID NO: 4, SEQ ID NO: 9, SEQ ID NO: 10, SEQ ID NO: 36, or SEQ ID NO: 39;
c) a nucleic acid sequence that is able to hybridize to the nucleotide sequence as shown in SEQ ID NO: 3, SEQ ID NO: 4, SEQ ID NO: 9, SEQ ID NO: 10, SEQ ID NO: 36, or SEQ ID NO: 39 under a low stringency condition or a strict stringency condition;
d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 3, SEQ ID NO: 4, SEQ ID NO: 9, SEQ ID NO: 10, SEQ ID NO: 36, or SEQ ID NO: 39;
e) a nucleic acid sequence that encodes an amino acid sequence, wherein the amino acid sequence has a homology of at least 90% with or at least 90% identical to the amino acid sequence shown in SEQ ID NO: 33 or SEQ ID NO: 35;
f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 33 or SEQ ID NO: 35;
g) a nucleic acid sequence that encodes an amino acid sequence, wherein the amino acid sequence is different from the amino acid sequence shown in SEQ ID NO: 33 or SEQ ID NO: 35 by no more than 10, 9, 8, 7, 6, 5, 4, 3, 2 or no more than 1 amino acid; and/or
h) a nucleic acid sequence that encodes an amino acid sequence, wherein the amino acid sequence comprises a substitution, a deletion and/or insertion of one or more amino acids to the amino acid sequence shown in SEQ ID NO: 33 or SEQ ID NO: 35.

The present disclosure further relates to a PD-1 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 3, SEQ ID NO: 4, SEQ ID NO: 9, SEQ ID NO: 10, SEQ ID NO: 36, or SEQ ID NO: 39.

The disclosure also provides an amino acid sequence that has a homology of at least 90% with, or at least 90% identical to the sequence shown in SEQ ID NO: 33 or SEQ ID NO: 35, and has protein activity. In some embodiments, the homology with the sequence shown in SEQ ID NO: 33 or SEQ ID NO: 35 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 33 or SEQ ID NO: 35 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 3, SEQ ID NO: 4, SEQ ID NO: 9, SEQ ID NO: 10, SEQ ID NO: 36, or SEQ ID NO: 39, and encodes a polypeptide that has protein activity. In some embodiments, the homology with the sequence shown in SEQ ID NO: 3, SEQ ID NO: 4, SEQ ID NO: 9, SEQ ID NO: 10, SEQ ID NO: 36, or SEQ ID NO: 39 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 3, SEQ ID NO: 4, SEQ ID NO: 9, SEQ ID NO: 10, SEQ ID NO: 36, or SEQ ID NO: 39 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) PD-1 from an endogenous non-human PD-1 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous PD-1 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized PD-1 gene or a humanized PD-1 nucleic acid. In some embodiments, at least one or more portions of the gene or the nucleic acid is from the human PD-1 gene, at least one or more portions of the gene or the nucleic acid is from a non-human PD-1 gene. In some embodiments, the gene or the nucleic acid comprises a sequence that encodes a PD-1 protein. The encoded PD-1 protein is functional or has at least one activity of the human PD-1 protein or the non-human PD-1 protein, e.g., binding with human or non-human PD-L1 or PD-L2, decreasing the level of activation of immune cells (e.g., T cells), reducing apoptosis in regulatory T cells, promoting apoptosis in antigen-specific T-cells in lymph nodes, and/or downregulating the immune response.

In some embodiments, the chimeric protein or the chimeric polypeptide is a humanized PD-1 protein or a humanized PD-1 polypeptide. In some embodiments, at least one or more portions of the amino acid sequence of the protein or the polypeptide is from a human PD-1 protein, and at least one or more portions of the amino acid sequence of the protein or the polypeptide is from a non-human PD-1 protein. The humanized PD-1 protein or the humanized PD-1 polypeptide is functional or has at least one activity of the human PD-1 protein or the non-human PD-1 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized PD-1 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100 (9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human PD-1 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature PD-1 coding sequence with human mature PD-1 coding sequence or an insertion of human mature PD-1 coding sequence or chimeric PD-1 coding sequence.

Genetically modified non-human animals that comprise a modification of an endogenous non-human PD-1 locus. In some embodiments, the modification can comprise a human nucleic acid sequence encoding at least a portion of a mature PD-1 protein (e.g., at least 10%, 20%, 30%, 40%, 50%, 60%, 70%, 80%, 90%, 95%, 96%, 97%, 98%, or 99% identical to the mature PD-1 protein sequence). Although genetically modified cells are also provided that can comprise the modifications described herein (e.g., ES cells, somatic cells), in many embodiments, the genetically modified non-human animals comprise the modification of the endogenous PD-1 locus in the germline of the animal.

Genetically modified animals can express a human PD-1 and/or a chimeric (e.g., humanized) PD-1 from endogenous mouse loci, wherein the endogenous mouse PD-1 gene has been replaced with a human PD-1 gene and/or a nucleotide sequence that encodes a region of human PD-1 sequence or an amino acid sequence that is at least 10%, 20%, 30%, 40%, 50%, 60%, 70&, 80%, 90%, 95%, 96%, 97%, 98%, or 99% identical to the human PD-1 sequence. In various embodiments, an endogenous non-human PD-1 locus is modified in whole or in part to comprise human nucleic acid sequence encoding at least one protein-coding sequence of a mature PD-1 protein.

In some embodiments, the genetically modified mice express the human PD-1 and/or chimeric PD-1 (e.g., humanized PD-1) from endogenous loci that are under control of mouse promoters and/or mouse regulatory elements. The replacement(s) at the endogenous mouse loci provide non-human animals that express human PD-1 or chimeric PD-1 (e.g., humanized PD-1) in appropriate cell types and in a manner that does not result in the potential pathologies observed in some other transgenic mice known in the art. The human PD-1 or the chimeric PD-1 (e.g., humanized PD-1) expressed in animal can maintain one or more functions of the wildtype mouse or human PD-1 in the animal.

For example, human or non-human PD-1 ligands (e.g., PD-L1 or PD-L2) can bind to the expressed PD-1, downregulate immune response, e.g., downregulate immune response by at least 10%, 20%, 30%, 40%, or 50%. Furthermore, in some embodiments, the animal does not express endogenous PD-1. As used herein, the term "endogenous PD-1" refers to PD-1 protein that is expressed from an endogenous PD-1 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human PD-1 (NP_005009.2) (SEQ ID NO: 35). In some embodiments, the genome comprises a sequence encoding an amino acid sequence that is at least 70%, 75%, 80%, 85%, 90%, 95%, 99%, or 100% identical to SEQ ID NO: 33.

The genome of the genetically modified animal can comprise a replacement at an endogenous PD-1 gene locus of a sequence encoding a region of endogenous PD-1 with a sequence encoding a corresponding region of human PD-1. In some embodiments, the sequence that is replaced is any sequence within the endogenous PD-1 gene locus, e.g., exon 1, exon 2, exon 3, exon 4, exon 5, 5'-UTR, 3'-UTR, the first intron, the second intron, the third intron, and the fourth intron, etc. In some embodiments, the sequence that is replaced is within the regulatory region of the endogenous PD-1 gene. In some embodiments, the sequence that is replaced is exon 1 or part thereof, of an endogenous mouse PD-1 gene locus.

In some embodiments, a sequence that encodes an amino acid sequence (e.g., human PD-1 or chimeric PD-1) is inserted after the start codon (e.g., within 10, 20, 30, 40, 50, 60, 70, 80, 90, or 100 nucleic acids). The start codon is the first codon of a messenger RNA (mRNA) transcript translated by a ribosome. The start codon always codes for methionine in eukaryotes and a modified Met (fMet) in prokaryotes. The most common start codon is ATG (or AUG in mRNA).

In some embodiments, the inserted sequence further comprises a stop codon (e.g., TAG, TAA, TGA). The stop codon (or termination codon) is a nucleotide triplet within messenger RNA that signals a termination of translation into proteins. Thus, the endogenous sequence after the stop codon will not be translated into proteins. In some embodiments, at least one exon of (e.g., exon 1, exon 2, exon 3, exon 4, and/or exon 5) of the endogenous PD-1 gene are not translated into proteins.

The genetically modified animal can have one or more cells expressing a human or chimeric PD-1 (e.g., humanized PD-1) having an extracellular region and a cytoplasmic region, wherein the extracellular region comprises a sequence that is at least 50%, 60%, 70%, 80%, 90%, 95%, 99% identical to the extracellular region of human PD-1. In some embodiments, the extracellular region of the humanized PD-1 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human PD-1. Because human PD-1 and non-human PD-1 (e.g., mouse PD-1) sequences, in many cases, are different, antibodies that bind to human PD-1 will not necessarily have the same binding affinity with non-human PD-1 or have the same effects to non-human PD-1. Therefore, the genetically modified animal having a human or a humanized extracellular region can be used to better evaluate the effects of anti-human PD-1 antibodies in an animal model. In some embodiments, the genome of the genetically modified animal comprises a sequence encoding an amino acid sequence that corresponds to part or the entire sequence of exon 1, exon 2, exon 3, exon 4, and/or exon 5 of human PD-1, part or the entire sequence of extracellular region of human PD-1 (with or without signal peptide), or part or the entire sequence of amino acids 1-167 of SEQ ID NO: 35.

In some embodiments, the non-human animal can have, at an endogenous PD-1 gene locus, a nucleotide sequence encoding a chimeric human/non-human PD-1 polypeptide, wherein a human portion of the chimeric human/non-human PD-1 polypeptide comprises a portion of human PD-1 extracellular domain, and wherein the animal expresses a functional PD-1 on a surface of a cell of the animal. The human portion of the chimeric human/non-human PD-1 polypeptide can comprise a portion of exon 1, exon 2, exon 3, exon 4, and/or exon 5 of human PD-1. In some embodiments, the human portion of the chimeric human/non-human PD-1 polypeptide can comprise a sequence that is at least 80%, 85%, 90%, 95%, or 99% identical to amino acids 1-167 of SEQ ID NO: 35.

In some embodiments, the non-human portion of the chimeric human/non-human PD-1 polypeptide comprises transmembrane and/or cytoplasmic regions of an endogenous non-human PD-1 polypeptide. There may be several advantages that are associated with the transmembrane and/or cytoplasmic regions of an endogenous non-human PD-1 polypeptide. For example, once a PD-1 ligand (e.g., PD-L1) or an anti-PD-1 antibody binds to PD-1, they can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of PD-1 are also derived from endogenous sequence. These amino acids can also be important for transmembrane signal transmission.

Furthermore, the genetically modified animal can be heterozygous with respect to the replacement or insertion at the endogenous PD-1 locus, or homozygous with respect to the replacement or insertion at the endogenous PD-1 locus.

In some embodiments, the genetically modified animal (e.g., a rodent) comprises a humanization of an endogenous PD-1 gene, wherein the humanization comprises a replacement at the endogenous rodent PD-1 locus of a nucleic acid comprising an exon of a PD-1 gene with a nucleic acid sequence comprising at least one exon of a human PD-1 gene to form a modified PD-1 gene.

In some embodiments, the genetically modified animal (e.g., a rodent) comprises an insertion at the endogenous rodent PD-1 locus of a nucleic acid sequence comprising at least one exon of a human PD-1 gene to form a modified PD-1 gene In some embodiments, the expression of the modified PD-1 gene is under control of regulatory elements at the endogenous PD-1 locus. In some embodiments, the modified PD-1 gene is operably linked to a WPRE element.

In some embodiments, the humanized PD-1 locus lacks a human PD-1 5'-UTR. In some embodiment, the humanized PD-1 locus comprises a rodent (e.g., mouse) 5'-UTR. In some embodiments, the humanization comprises a human 3'-UTR. In appropriate cases, it may be reasonable to presume that the mouse and human PD-1 genes appear to be similarly regulated based on the similarity of their 5'-flanking sequence. As shown in the present disclosure, humanized PD-1 mice that comprise a replacement at an endogenous mouse PD-1 locus, which retain mouse regulatory elements but comprise a humanization of PD-1 encoding sequence, do not exhibit obvious pathologies. Both genetically modified mice that are heterozygous or homozygous for humanized PD-1 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized PD-1 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized PD-1 in the genome of the animal.

Figure 3A:
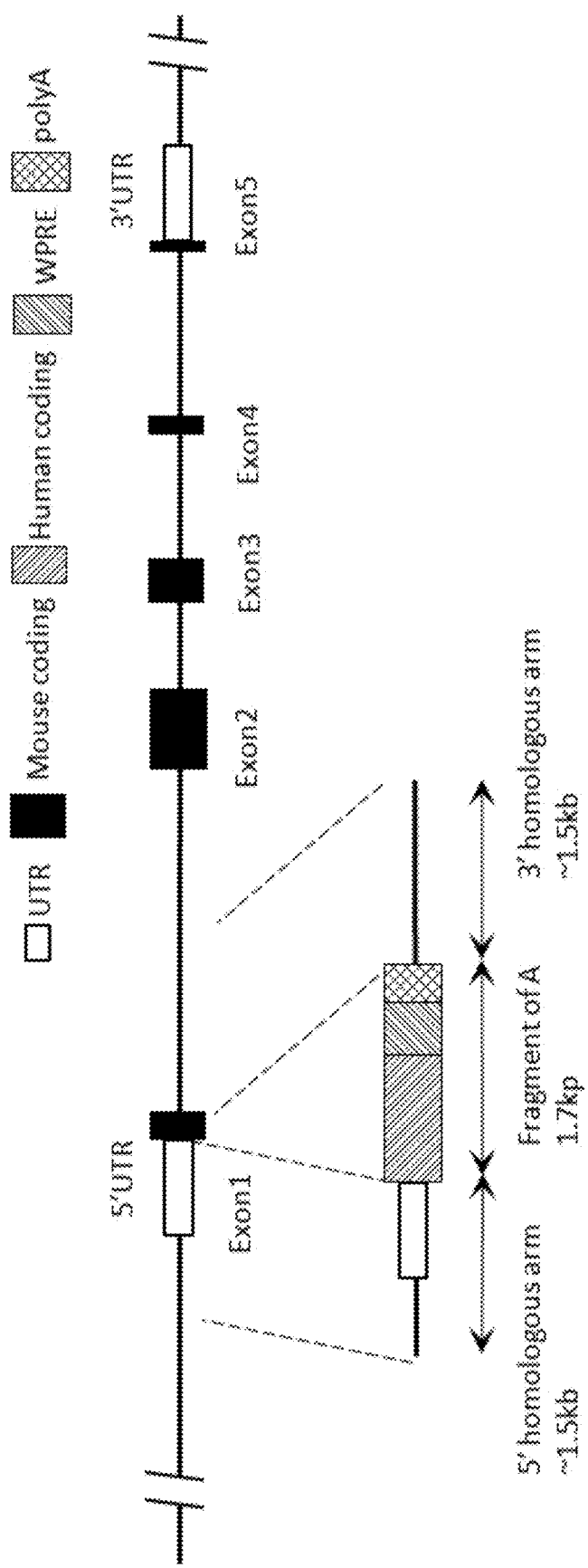
FIG. 3A is a schematic diagram showing a gene targeting strategy for embryonic stem cells for a sequence encoding human PD-1 amino acid sequence.
Figure 3B:
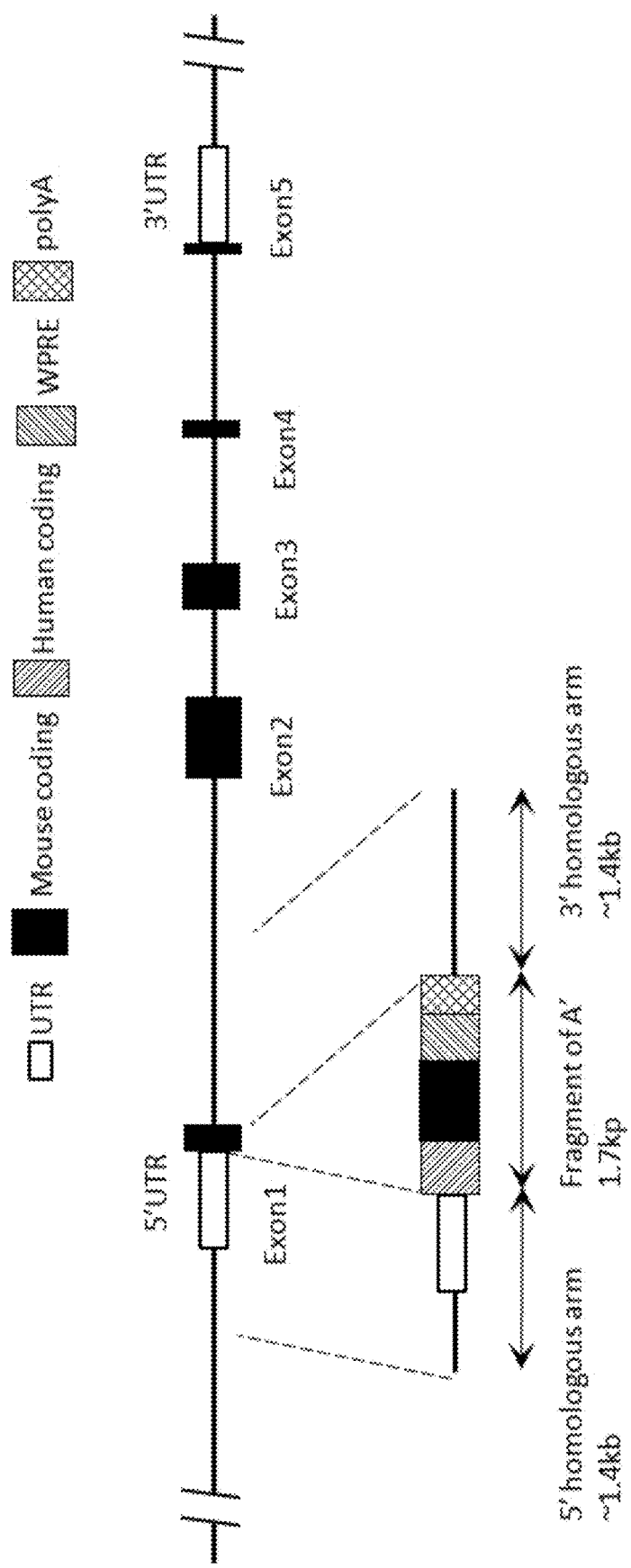
FIG. 3B is a schematic diagram showing a gene targeting strategy for embryonic stem cells for a sequence encoding a chimeric PD-1 amino acid sequence.

In some embodiments, the non-human mammal comprises the genetic construct as described herein (e.g., gene construct as shown in FIGS. 3A-3B). In some embodiments, a non-human mammal expressing human or humanized PD-1 is provided. In some embodiments, the tissue-specific expression of human or humanized PD-1 protein is provided.

In some embodiments, the expression of human or humanized PD-1 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human PD-1 protein or chimeric PD-1 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized PD-1 protein.

Vectors

The present disclosure relates to a targeting vector, comprising: a) a DNA fragment homologous to the 5' end of a region to be altered (5' arm), which is selected from the PD-1 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the PD-1 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000067.6; c) the DNA fragment homologous to the 3' end of the region to be altered (3' arm) is selected from the nucleotide sequences that have at least 90% homology to the NCBI accession number NC_000067.6.

In some embodiments, a) the DNA fragment homologous to the 5' end of a region to be altered (5' arm) is selected from the nucleotides from the position 94052491 to the position 94053890 of the NCBI accession number NC_000067.6; c) the DNA fragment homologous to the 3' end of the region to be altered (3' arm) is selected from the nucleotides from the position 94051015 to the position 94052414 of the NCBI accession number NC_000067.6.

In some embodiments, the length of the selected genomic nucleotide sequence in the targeting vector can be more than about 3 kb, about 3.5 kb, about 4 kb, about 4.5 kb, about 5 kb, about 5.5 kb, or about 6 kb.

In some embodiments, the region to be altered is exon 1, exon 2, exon 3, exon 4, and/or exon 5 of PD-1 gene (e.g., exon 1 of mouse PD-1 gene).

The targeting vector can further include a selected gene marker.

In some embodiments, the sequence of the 5' arm is shown in SEQ ID NO: 7; and the sequence of the 3' arm is shown in SEQ ID NO: 8.

In some embodiments, the sequence is derived from human. For example, the target region in the targeting vector is a part or entirety of the nucleotide sequence of a human PD-1 or a chimeric PD-1. In some embodiments, the nucleotide sequence of the humanized PD-1 encodes the entire or the part of human PD-1 protein with the NCBI accession number NP_005009.2 (SEQ ID NO: 35).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous PD-1 gene locus, a sequence encoding a region of an endogenous PD-1 with a sequence encoding a corresponding region of human PD-1, a sequencing encoding human PD-1, or a sequencing encoding chimeric PD-1.

In some embodiments, the disclosure provides inserting in at least one cell of the animal, at an endogenous PD-1 gene locus, a sequence encoding a human PD-1 or a chimeric PD-1.

In some embodiments, the genetic modification occurs in a germ cell, a somatic cell, a blastocyst, or a fibroblast, etc. The nucleus of a somatic cell or the fibroblast can be inserted into an enucleated oocyte.

FIGS. 3A-3B show a humanization strategy for a mouse PD-1 locus. In FIGS. 3A-3B, the targeting strategy involves a vector comprising the 5' end homologous arm, human PD-1 gene fragment or chimeric PD-1 gene fragment, 3' homologous arm. The process can involve replacing endogenous PD-1 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous PD-1 sequence with human PD-1 sequence.

Thus, in some embodiments, the methods for making a genetically modified, humanized animal, can include the step of replacing at an endogenous PD-1 locus (or site), a nucleic acid encoding a sequence encoding a region of endogenous PD-1 with a sequence encoding a human PD-1 or a chimeric PD-1. The sequence can include a region (e.g., a part or the entire region) of exon 1, exon 2, exon 3, exon 4, exon 5 of a human PD-1 gene. In some embodiments, the sequence includes a region of exon 1, exon 2, exon 3, exon 4, exon 5 of a human PD-1 gene (e.g., amino acids 1-167 of SEQ ID NO: 35). In some embodiments, the region is located within the extracellular region of PD-1. In some embodiments, the endogenous PD-1 locus is exon 1, exon 2, exon 3, exon 4, and/or exon 5 of mouse PD-1 (e.g., exon 1).

In some embodiments, the methods of modifying a PD-1 locus of a mouse to express a chimeric human/mouse PD-1 peptide can include the steps of replacing at the endogenous mouse PD-1 locus a nucleotide sequence encoding a mouse PD-1 with a nucleotide sequence encoding a human PD-1, thereby generating a sequence encoding a chimeric human/mouse PD-1.

In some embodiments, the nucleotide sequence encoding the chimeric human/mouse PD-1 can include a first nucleotide sequence encoding an extracellular region of mouse PD-1 (with or without the mouse or human signal peptide sequence); a second nucleotide sequence encoding an extracellular region of human PD-1; a third nucleotide sequence encoding a transmembrane and a cytoplasmic region of a mouse PD-1.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a PD-1 gene humanized animal model, involving the following steps:
(a) providing the cell (e.g. a fertilized egg cell) based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;
(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements and the exogenous WPRE element provides a physiologically appropriate expression pattern and level that results in a useful humanized animal whose physiology with respect to the replaced gene are meaningful and appropriate in the context of the humanized animal's physiology.

Genetically modified animals that express human or humanized PD-1 protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized PD-1, which are useful for testing agents that can decrease or block the interaction between PD-1 and PD-1 ligands (e.g., PD-L1 or PD-L2) or the interaction between PD-1 and anti-human PD-1 antibodies, testing whether an agent can increase or decrease the immune response, and/or determining whether an agent is an PD-1 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of a PD-1 inhibitor for the treatment of cancer. The methods involve administering the PD-1 inhibitor (e.g., anti-human PD-1 antibody or anti-human PD-L1 antibody) to the animal as described herein, wherein the animal has a tumor; and determining the inhibitory effects of the PD-1 inhibitor to the tumor. In some embodiments, the PD-1 inhibitor is an anti-human PD-1 antibody or anti-human PD-L1 antibody.

The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-PD-1 antibody, anti-PD-L1 antibody or anti-PD-L2 antibody prevents PD-1 ligands from binding to PD-1. In some embodiments, the anti-PD-1 antibody, anti-PD-L1 antibody, or anti-PD-L2 antibody does not prevent the ligands from binding to PD-1.

In some embodiments, the genetically modified animals can be used for determining whether an anti-PD-1 antibody is a PD-1 agonist or antagonist. In some embodiments, the methods as described herein are also designed to determine the effects of the agent (e.g., anti-PD-1 antibodies) on PD-1, e.g., whether the agent can stimulate immune cells or inhibit immune cells (e.g., T cells), whether the agent can increase or decrease the production of cytokines, whether the agent can activate or deactivate immune cells (e.g., T cells, macrophages, B cells, or DC), whether the agent can upregulate the immune response or downregulate immune response, and/or whether the agent can induce complement mediated cytotoxicity (CMC) or antibody dependent cellular cytoxicity (ADCC). In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-PD-1 antibody or the anti-PD-L1 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-PD-1 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-PD-1 antibody is designed for treating hepatocellular, ovarian, colon, or cervical carcinomas. In some embodiments, the anti-PD-1 antibody is designed for treating advanced breast cancer, advanced ovarian cancer, and/or advanced refractory solid tumor. In some embodiments, the anti-PD-1 antibody is designed for treating metastatic solid tumors, NSCLC, melanoma, non-Hodgkin lymphoma, colorectal cancer, and multiple myeloma. In some embodiments, the anti-PD-1 antibody is designed for treating melanoma, pancreatic carcinoma, mesothelioma, hematological malignancies (e.g., Non-Hodgkin's lymphoma, lymphoma, chronic lymphocytic leukemia), or solid tumors (e.g., advanced solid tumors). In some embodiments, the anti-PD-1 antibody is designed for treating carcinomas (e.g., nasopharynx carcinoma, bladder carcinoma, cervix carcinoma, kidney carcinoma or ovary carcinoma).

In some embodiments, the anti-PD-1 antibody is designed for treating various autoimmune diseases. Thus, the methods as described herein can be used to determine the effectiveness of an anti-PD-1 antibody in inhibiting immune response.

The present disclosure also provides methods of determining toxicity of an antibody (e.g., anti-PD-1 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the PD-1 gene function, human PD-1 antibodies, drugs for human PD-1 targeting sites, the drugs or efficacies for human PD-1 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric PD-1 gene and a sequence encoding an additional human or chimeric protein.

In some embodiments, the additional human or chimeric protein can be cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), or TNF Receptor Superfamily Member 4 (TNFRSF4 or OX40).

The methods of generating genetically modified animal model with two or more human or chimeric genes (e.g., humanized genes) can include the following steps:
(a) using the methods of introducing human PD-1 gene or chimeric PD-1 gene as described herein to obtain a genetically modified non-human animal;
(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric CTLA-4, LAG-3, BTLA, PD-L1, CD27, CD28, CD40, CD47, CD137, CD154, TIGIT, TIM-3, GITR, SIRPa, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

In some embodiments, the PD-1 humanization is directly performed on a genetically modified animal having a human or chimeric CTLA-4, BTLA, PD-L1, CD27, CD28, CD40, CD47, CD137, CD154, TIGIT, TIM-3, GITR, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-PD-1 antibody and an additional therapeutic agent for the treatment of cancer. The methods include administering the anti-PD-1 antibody and the additional therapeutic agent to the animal, wherein the animal has a tumor; and determining the inhibitory effects of the combined treatment to the tumor. In some embodiments, the additional therapeutic agent is an antibody that specifically binds to CTLA-4, BTLA, PD-L1, CD27, CD28, CD40, CD47, CD137, CD154, TIGIT, TIM-3, GITR, or OX40. In some embodiments, the additional therapeutic agent is an anti-CTLA4 antibody (e.g., ipilimumab), an anti-PD-1 antibody (e.g., nivolumab, pembrolizumab), or an anti-PD-L1 antibody.

In some embodiments, the animal further comprises a sequence encoding a human or humanized PD-L1, or a sequence encoding a human or humanized CTLA-4. In some embodiments, the additional therapeutic agent is an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.
Materials and Methods
The following materials were used in the following examples.
C57BL/6 mice were purchased from the China Food and Drugs Research Institute National Rodent Experimental Animal Center.
Cas9 mRNA was purchased from SIGMA (Catalog number: CAS9MRNA-1EA).
BamHI, ScaI, SalI, NcoI, AseI restriction enzymes were purchased from NEB (Catalog numbers: R3136M, R3122M, R3138M, R3193M, R0526S).
UCA kit was obtained from Beijing Biocytogen Co., Ltd. (Catalog number: BCG-DX-001).
MEGAshortscript T7 Kit was obtained from Thermo Fisher (Catalog number: AM1354).
Purified NA/LE Hamster Anti-Mouse CD3e (mCD3) antibody was purchased from BD (Catalog number: 553057).
PE anti-mouse CD279 (PD-1) antibody (mPD-1 PE) was purchased from Biolegend (Catalog number: 109104).
PerCP/Cy5.5 anti-mouse TCR β chain (mTcRβ PerCP) was purchased from Biolegend (Catalog number: 109228).
FITC anti-human CD279 (PD-1) antibody (hPD-1 FITC) was purchased from Biolegend (Catalog number: 329904).
APC anti-human CD279 antibody (hPD-1APC) was purchased from BD Pharmingen (Catalog number: 558694).
Alexa Fluor® 647 AffiniPure F (ab') 2 Fragment Goat Anti-Human IgG, Fcγ Fragment Specific (Anti-Fab AF647) was obtained from Jackson (Catalog number: 109-606-098).
Flow cytometer was purchased from BD Biosciences (model: FACS Calibur™).

Example 1: Sequence Design for Humanized PD-1 Mice

A sequence that encodes human PD-1 or chimeric PD-1 can be inserted after the mouse PD-1 gene (Gene ID: 18566) start codon (ATG). The NCBI accession number for the mouse PD-1 gene and the protein is NM_008798.2→NP_032824.1. The mRNA sequence is shown in SEQ ID NO: 1, and the corresponding amino acid sequence is shown in SEQ ID NO: 2.
The sequence that encodes human PD-1 is set forth in SEQ ID NO: 3. The sequence that encodes chimeric PD-1 is set forth in SEQ ID NO: 4, and the amino acid sequence for the chimeric PD-1 is set forth in SEQ ID NO: 33. The NCBI accession number for the human PD-1 gene (Gene ID: 5133) and the protein is NM_005018.2→NP_005009.2. The mRNA sequence was shown in SEQ ID NO: 34, and the corresponding protein sequence is shown in SEQ ID NO: 35.

In order to improve the PD-1 protein expression and stability, Woodchuck Hepatitis Virus (WHP) Posttranscriptional Regulatory Element (WPRE) and polyA (polyadenylation) signal sequence were added after the human or chimeric PD-1 coding sequence. The WPRE sequence is set forth in SEQ ID NO: 5, and the polyA signal sequence is set forth in SEQ ID NO: 6.

Figure 2A:
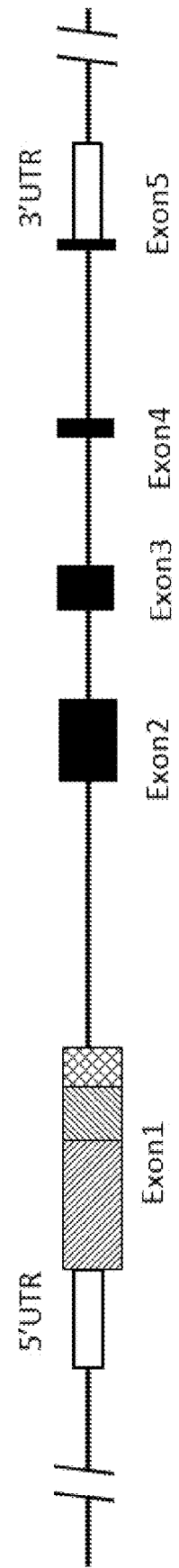
FIG. 2A is a schematic diagram showing a map of humanized PD-1 gene in mice (the sequence encodes human PD-1 amino acid sequence; huPD-1 version).
Figure 2B:
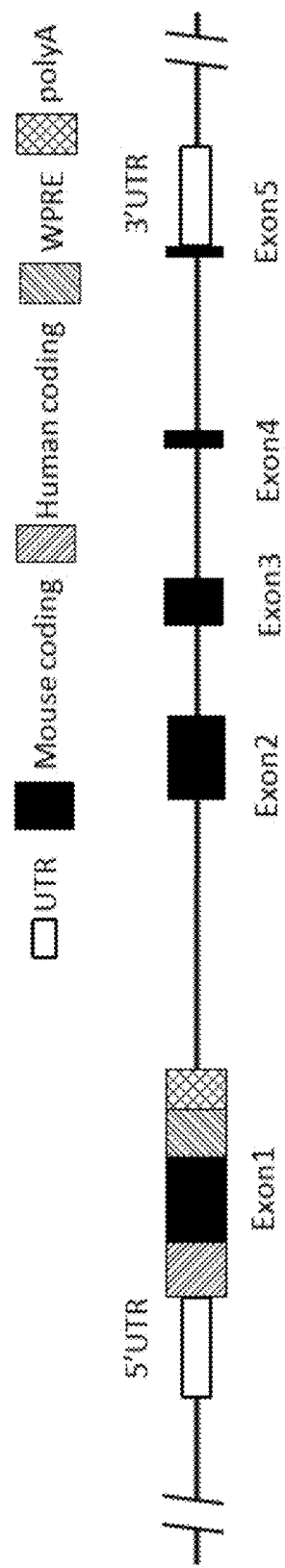
FIG. 2B is a schematic diagram showing a map of humanized PD-1 gene in mice (the sequence encodes a chimeric PD-1 amino acid sequence; chiPD-1 version).

The schematic diagram of the humanized mouse PD-1 gene is shown in FIGS. 2A and 2B. The expression of human PD-1 protein (SEQ ID NO: 35) or chimeric PD-1 protein (SEQ ID NO: 33) is controlled by the endogenous PD-1 promoter.

FIG. 3A further shows a targeting strategy to make mice that express the human PD-1 protein (huPD-1 version). FIG. 3B shows a targeting strategy to make mice that express the chimeric PD-1 protein (chiPD-1 version). Exon 2 to Exon 5 of the mouse PD-1 gene as shown in FIG. 1 were not translated due to the presence of a stop codon after the inserted sequences.

Example 2: Plasmid Construction and Verification

Based on the sequences, two targeting vectors for generating the humanized PD-1 mouse model that express human or chimeric PD-1 were designed.
Targeting Vector for Human PD-1 (huPD-1 Version)
The 5' homologous arm of one targeting vector (pUC57-huPD-1) comprises nucleic acid 94052491-94053890 of NCBI Accession No. NC_000067.6 (SEQ ID NO: 7). The 3' homologous arm comprises nucleic acid 94051015-94052414 of NCBI Accession No. NC_000067.6 (SEQ ID NO: 8). Fragment A (SEQ ID NO: 9) comprises a nucleic acid sequence that encodes human PD-1 sequence, the WPRE sequence, and the polyA signal sequence. The genetically engineered humanized mouse DNA sequence is shown in SEQ ID NO: 10. SEQ ID NO: 10 only shows the modified portion of DNA sequence, wherein the human PD-1 coding sequence is underlined, the wavy line in italics indicates the WPRE sequence, and the double underlined sequence is the polyA signal sequence.

The genetically engineered sequence in humanized mouse DNA sequence is shown below (SEQ ID NO: 10).

```
cgacactgccaggggctctgggcATGCAGATCCCACAGGCGCCCTGGCCA

GTCGTCTGGGCGGTGCTACAACTGGGCTGGCGGCCAGGATGGTTCTTAGA

CTCCCCAGACAGGCCCTGGAACCCCCCCACCTTCTCCCCAGCCCTGCTCG

TGGTGACCGAAGGGGACAACGCCACCTTCACCTGCAGCTTCTCCAACACA

TCGGAGAGCTTCGTGCTAAACTGGTACCGCATGAGCCCCAGCAACCAGAC

GGACAAGCTGGCCGCCTTCCCCGAGGACCGCAGCCAGCCCGGCCAGGACT

GCCGCTTCCGTGTCACACAACTGCCCAACGGGCGTGACTTCCACATGAGC

GTGGTCAGGGCCCGGCGCAATGACAGCGGCACCTACCTCTGTGGGGCCAT

CTCCCTGGCCCCCAAGGCGCAGATCAAAGAGAGCCTGCGGGCAGAGCTCA

GGGTGACAGAGAGAAGGGCAGAAGTGCCCACAGCCCACCCCAGCCCCTCA
```

CCCAGGCCAGCCGGCCAGTTCCAAACCCTGGTGGTTGGTGTCGTGGGCGG

CCTGCTGGGCAGCCTGGTGCTGCTAGTCTGGGTCCTGGCCGTCATCTGCT

CCCGGGCCGCACGAGGGACAATAGGAGCCAGGCGCACCGGCCAGCCCTG

AAGGAGGACCCCTCAGCCGTGCCTGTGTTCTCTGTGGACTATGGGGAGCT

GGATTTCCAGTGGCGAGAGAAGACCCCGGAGCCCCCCGTGCCCTGTGTCC

CTGAGCAGACGGAGTATGCCACCATTGTCTTTCCTAGCGGAATGGGCACC

TCATCCCCCGCCCGCAGGGGCTCAGCTGACGGCCCTCGGAGTGCCCAGCC

ACTGAGGCCTGAGGATGGACACTGCTCTTGGCCCCTCTGA*AATCAACCTC*

*TGGATTACAAAATTTGTGAAAGATTGACTGGTATTCTTAACTATGTTGCT*

*CCTTTTACGCTATGTGGATACGCTGCTTTAATGCCTTTGTATCATGCTAT*

*TGCTTCCCGTATGGCTTTCATTTTCTCCTCCTTGTATAAATCCTGGTTGC*

*TGTCTCTTTATGAGGAGTTGTGGCCCGTTGTCAGGCAACGTGGCGTGGTG*

*TGCACTGTGTTTGCTGACGCAACCCCCACTGGTTGGGGCATTGCCACCAC*

*CTGTCAGCTCCTTTCCGGGACTTTCGCTTTCCCCCTCCCTATTGCCACGG*

*CGGAACTCATCGCCGCCTGCCTTGCCCGCTGCTGGACAGGGGCTCGGCTG*

*TTGGGCACTGACAATTCCGTGGTGTTGTCGGGGAAATCATCGTCCTTTCC*

*TTGGCTGCTCGCCTGTGTTGCCACCTGGATTCTGCGCGGGACGTCCTTCT*

*GCTACGTCCCTTCGGCCCTCAATCCAGCGGACCTTCCTTCCCGCGGCCTG*

*CTGCCGGCTCTGCGGCCTCTTCCGCGTCTTCGCCTTCGCCCTCAGACGAG*

*TCGGATCTCCCTTTGGGCCGCCTCCCCGCATCGATACCGTCGACCTCGA*

CTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGA

GGAAATTGCATCGCATTGTCTGAGTAGGTGTCATTCTATTCTGGGGGGTG

GGGTGGGGCAGGACAGCAAGGGGGAGGATTGGGAAGACAATAGCAGGCAT

GCTGGGGAATTAATAGTACTgtatgtggctcctagggatgt

Targeting Vector for Chimeric PD-1 (chiPD-1 Version)

The 5' homologous arm and the 3' homologous arm of the second targeting vector are the same as the targeting vector for human PD-1. However, the sequence for Fragment A is different. The sequence for Fragment A' (SEQ ID NO: 39) includes the sequence (SEQ ID NO: 4) that encodes chimeric PD-1 (SEQ ID NO: 33), the WPRE sequence, and the polyA signal sequence. The final genetically engineered PD-1 sequence in humanized mouse DNA sequence is set forth by SEQ ID NO: 36. SEQ ID NO: 36 only shows the modified portion of DNA sequence, wherein the human PD-1 coding sequence is underlined, the double underlined portion is the mouse PD-1 coding sequence, the italicized portion is the WPRE sequence, and the wavy underlined portion is the polyA signal sequence.

The genetically engineered sequence in humanized mouse DNA sequence is shown below (SEQ ID NO: 36):

tgccaggggctctgggcATGCAGATCCCACAGGCGCCCTGGCCAGTCGTC

TGGGCGGTGCTACAACTGGGCTGGCGGCCAGGATGGTTCTTAGACTCCCC

AGACAGGCCCTGGAACCCCCCCACCTTCTCCCCAGCCCTGCTCGTGGTGA

CCGAAGGGGACAACGCCACCTTCACCTGCAGCTTCTCCAACACATCGGAG

AGCTTCGTGCTAAACTGGTACCGCATGAGCCCCAGCAACCAGACGGACAA

GCTGGCCGCCTTCCCCGAGGACCGCAGCCAGCCCGGCCAGGACTGCCGCT

TCCGTGTCACACAACTGCCCAACGGGCGTGACTTCCACATGAGCGTGGTC

AGGGCCCGGCGCAATGACAGCGGCACCTACCTCTGTGGGGCCATCTCCCT

GGCCCCCAAGGCGCAGATCAAAGAGAGCCTGCGGGCAGAGCTCAGGGTGA

CAGAGAGAAGGGCAGAAGTGCCCACAGCCCACCCCAGCCCCTCACCCAGG

CCAGCCGGCCAGTTCCAAGGCATGGTCATTGGTATCATGAGTGCCCTAGT

GGGTATCCCTGTATTGCTGCTGCTGGCCTGGGCCCTAGCTGTCTTCTGCT

CAACAAGTATGTCAGAGGCCAGAGGAGCTGGAAGCAAGGACGACACTCTG

AAGGAGGAGCCTTCAGCAGCACCTGTCCCTAGTGTGGCCTATGAGGAGCT

GGACTTCCAGGGACGAGAGAAGACACCAGAGCTCCCTACCGCCTGTGTGC

ACACAGAATATGCCACCATTGTCTTCACTGAAGGGCTGGGTGCCTCGGCC

ATGGGACGTAGGGGCTCAGCTGATGGCCTGCAGGGTCCTCGGCCTCCAAG

ACATGAGGATGGACATTGTTCTTGGCCTCTTTGAAATCAACCTCTGGATT

ACAAAATTTGTGAAAGATTGACTGGTATTCTTAACTATGTTGCTCCTTTT

ACGCTATGTGGATACGCTGCTTTAATGCCTTTGTATCATGCTATTGCTTC

CCGTATGGCTTTCATTTTCTCCTCCTTGTATAAATCCTGGTTGCTGTCTC

TTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCA

GCTCCTTTCCGGGACTTTCGCTTTCCCCCTCCCTATTGCCACGGCGGAAC

TCATCGCCGCCTGCCTTGCCCGCTGCTGGACAGGGGCTCGGCTGTTGGGC

ACTGACAATTCCGTGGTGTTGTCGGGGAAATCATCGTCCTTTCCTTGGCT

GCTCGCCTGTGTTGCCACCTGGATTCTGCGCGGGACGTCCTTCTGCTACG

TCCCTTCGGCCCTCAATCCAGCGGACCTTCCTTCCCGCGGCCTGCTGCCG

GCTCTGCGGCCTCTTCCGCGTCTTCGCCTTCGCCCTCAGACGAGTCGGAT

CTCCCTTTGGGCCGCCTCCCCGCATCGATACCGTCGACCTCGACTGTGCC

TTCTAGTTGCCAGCCATCTGTTGTTTGCCCCTCCCCCGTGCCTTCCTTGA

CCCTGGAAGGTGCCACTCCCACTGTCCTTTCCTAATAAAATGAGGAAATT

GCATCGCATTGTCTGAGTAGGTGTCATTCTATTCTGGGGGGTGGGGTGGG

GCAGGACAGCAAGGGGGAGGATTGGGAAGACAATAGCAGGCATGCTGGGG

Aattaatagtactgtatgtggc

Synthesizing Targeting Vectors

The targeting vectors were synthesized (using the pUC57 plasmid as a backbone plasmid) according to the designed targeting vector sequence. A number of pUC57-huPD-1plasmids (targeting vectors for human PD-1) and pUC57- chiPD-1 plasmids (targeting vectors for chimeric PD-1) were synthesized. They were randomly selected and verified by restriction endonuclease digestion. For pUC57-huPD-1 plasmids (targeting vectors for human PD-1), ScaI enzyme should generate 3175 bp+4031 bp fragments, SalI should generate 1647 bp+5559 bp fragments, and NcoI+ScaI should generate 998 bp+2177 bp+4031 bp fragments. For pUC57-chiPD-1 plasmids (targeting vectors for chimeric PD-1), ScaI enzyme should generate 3167 bp+4024 bp fragments, NdeI should generate 3032 bp+4159 bp fragments, and BamHI+NotI should generate 2769 bp+4422 bp fragments.

Figure 4A:
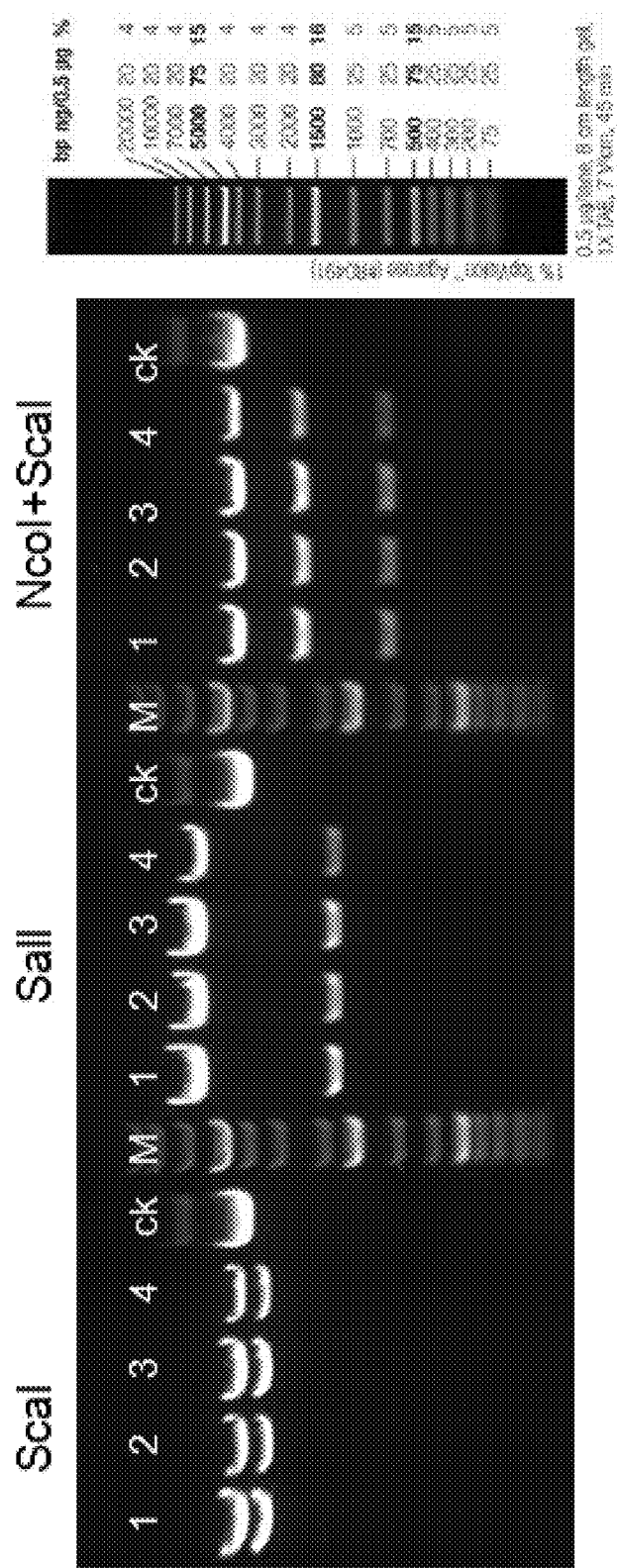
FIG. 4A shows the restriction enzymes digestion results of the targeting plasmid pUC57-huPD-1 (huPD-1 version) by three sets of restriction enzymes. Ck indicates undigested plasmids, which were used as a control.
Figure 4B:
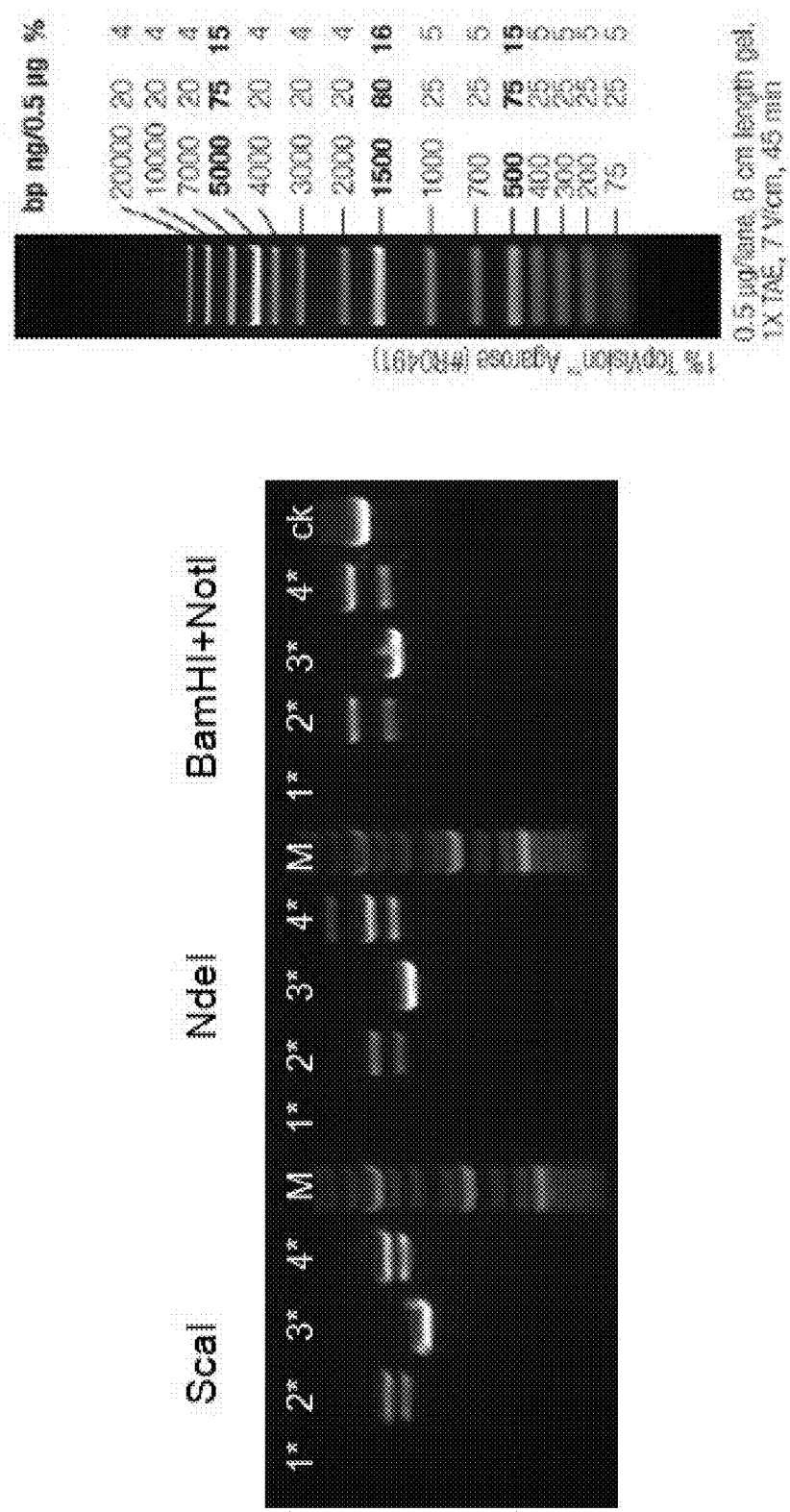
FIG. 4B shows the restriction enzymes digestion results of the targeting plasmid pUC57-chiPD-1 (chiPD-1 version) by three sets of restriction enzymes. Ck indicates undigested plasmids, which were used as a control

The results are shown in FIGS. 4A-4B. In FIG. 4A, the digestion results of all tested pUC57-huPD-1 plasmids were in agreement with the expected results, indicating that the plasmids had the correct sequences. The sequences for the plasmids labeled with 1 and 2 were further verified by sequencing.

In FIG. 4B, the digestion results for the plasmids labeled with 2* and 4* were in agreement with the expected results. The sequences for the plasmid labeled with 2* was further verified by sequencing.

Plasmid 2 in FIG. 4A and Plasmid 2* in FIG. 4B were then selected for subsequent experiments.

Example 3: Design of sgRNA for PD-1 Gene

The target sequence determines the targeting specificity of sgRNAs and the efficiency of inducing Cas9 cleavage at the gene of interest. Thus, it is important to test the efficiency of the specific target sequence. The targeting sites and the sgRNAs were designed and synthesized. The targeting sites were located in exon 1 of mouse PD-1 gene. The targeting site sequences on PD-1 for each sgRNA are shown below:

```
sgRNA1 target sequence (SEQ ID NO: 11):
5'-tctgggcatgtgggtccggcagg-3' sgRNA2 target sequence (SEQ ID NO: 12):
5'-tgtgggtccggcaggtaccctgg-3' sgRNA3 target sequence (SEQ ID NO: 13):
5'-ctgcagttgagctggcaatcagg-3' sgRNA4 target sequence (SEQ ID NO: 14):
5'-aggtaccctggtcattcacttgg-3' sgRNA5 target sequence (SEQ ID NO: 15):
5'-tgaatgaccagggtacctgccgg-3' sgRNA6 target sequence (SEQ ID NO: 16):
5'-agttgagctggcaatcagggtgg-3' sgRNA7 target sequence (SEQ ID NO: 17):
5'-cagggtggcttctaggtatgtgg-3' sgRNA8 target sequence (SEQ ID NO: 18):
5'-acagcccaagtgaatgaccaggg-3' sgRNA9 target sequence (SEQ ID NO: 19):
5'-gccagggctctgggcatgtggg-3'
```

Example 4: Testing sgRNA Activity

Figure 5:
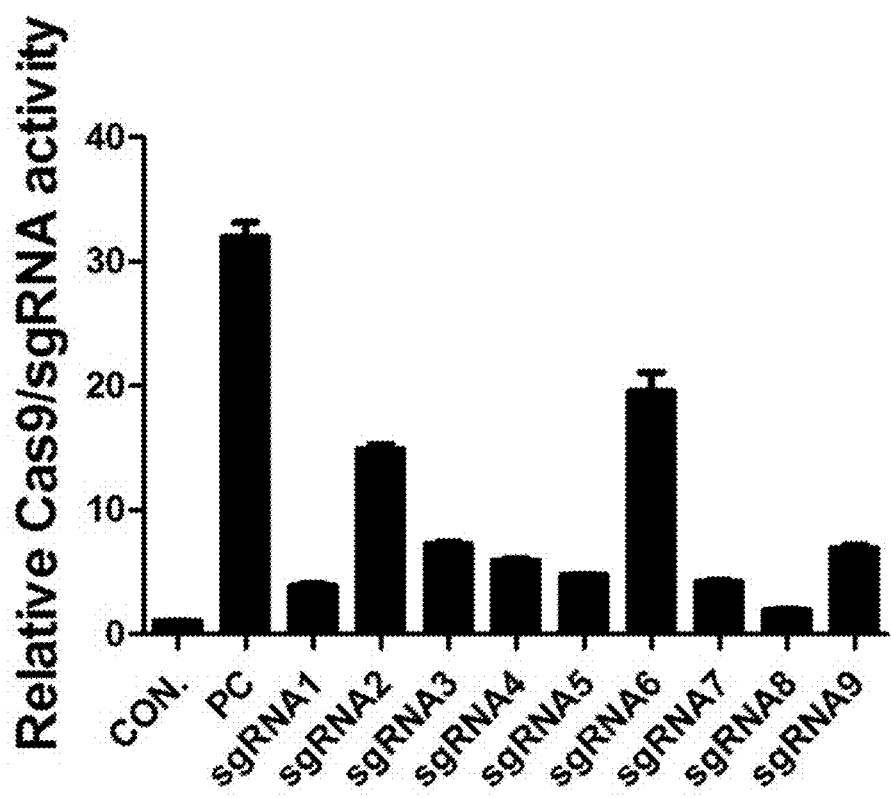
FIG. 5 is a graph showing activity testing results for sgRNA1-sgRNA9 (Con is a negative control; PC is a positive control).

The UCA kit was used to detect the activities of sgRNAs (FIG. 5). The results show that the guide sgRNAs had different activities.

sgRNA6 was selected for further experiments. The sgRNA6 sequences are shown below:

```
Upstream:
                            (SEQ ID NO: 20)
    5'-TTGAGCTGGCAATCAGGG-3'

Downstream:
                            (SEQ ID NO: 21)
    5'-CCCTGATTGCCAGCTCAA-3'
```

A DNA fragment containing T7 promoter, sgRNA6, and sgRNA scaffold (SEQ ID NO: 22) was synthesized, and linked to the backbone vector. MEGAshortscript T7 Kit was used to obtain in vitro transcripts.

Example 5: Microinjection and Embryo Transfer Using C57BL/6 Mice

The pre-mixed Cas9 mRNA, pUC57-huPD-1 or pUC57-chiPD-1 plasmid and in vitro transcription products (sgRNAs) were injected into the cytoplasm or nucleus of mouse fertilized eggs (C57BL/6 background) with a microinjection instrument. The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating and self-mating to establish stable mouse lines.

Example 6: Verification of Genetic Modification

1. Genotype Determination for F0 Generation Mice

PCR analysis was performed using mouse tail genomic DNA of F0 generation mice. Primer L-GT-F is located on the left side of 5' homologous arm, Primer R-GT-R is located on the right side of 3' homologous arm, and both R-GT-F and L-GT-R are located within the Fragment A.

```
5' end:
Upstream: L-GT-F (SEQ ID NO: 23):
5'-CCAGAAGAAGGTACAGCAGAAGGGG-3'

Downstream: L-GT-R (SEQ ID NO: 24):
5'-AAGCAGCGTATCCACATAGCGTAAA-3'

3' end:
Upstream: R-GT-F (SEQ ID NO: 25):
5'-GTGCCTGTGTTCTCTGTGGACTATG-3'

Downstream: R-GT-R (SEQ ID NO: 26):
5'-CTGGTCTTGAACTTTGATGGGCACG-3'
```

The reagents and the conditions for PCR are shown in the tables below.

TABLE 3

| The PCR reaction (20 μL) | |
| --- | --- |
| 2 × PCR buffer | 10 μL |
| dNTP (2 μM) | 4 μL |
| Upstream primer (10 μM) | 0.6 μL |
| Downstream primer (10 μM) | 0.6 μL |
| Mouse tail genomic DNA | 100 ng |
| KOD-FX (1 U/μL) | 0.4 μL |
| H$_2$O | Add to 20 μL |

TABLE 4

| The PCR reaction conditions | | |
| --- | --- | --- |
| Temperature | Time | Cycles |
| 94° C. | 5 min | 1 |
| 94° C. | 30 sec | 15 |
| 67° C. (−0.7° C./cycle) | 30 sec | |
| 68° C. | 1 kb/min | |
| 98° C. | 30 sec | 25 |
| 57° C. | 30 sec | |
| 68° C. | 1 kb/min | |
| 68° C. | 10 min | 1 |
| 4° C. | 10 min | 1 |

Figure 6A:
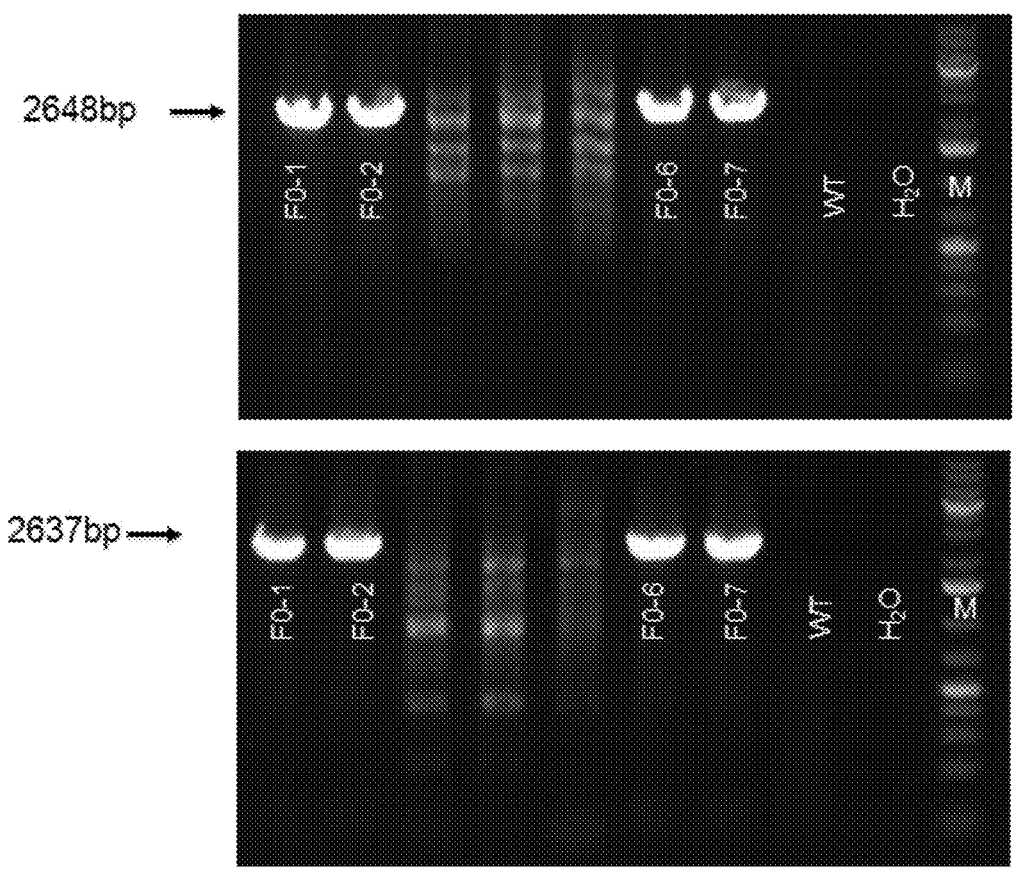
FIG. 6A shows PCR identification results of samples collected from tails of F0 generation mice (huPD-1 version). WT is wildtype. Mice labeled with F0-1, F0-2, F0-6 and F0-7 were positive.

If the desired human sequence was inserted into the correct positions in the genome, PCR experiments using the above primers should generate only one band. The 5' end PCR experiment should produce a band at about 2648 bp, and the 3' end PCR experiment should produce a band at about 2637 bp or 3070 bp. The results for seven F0 generation mice (huPD-1 version) are shown in FIG. 6A. Among them, F0-1, F0-2, F0-6 and F0-7 were positive.

Figure 6B:
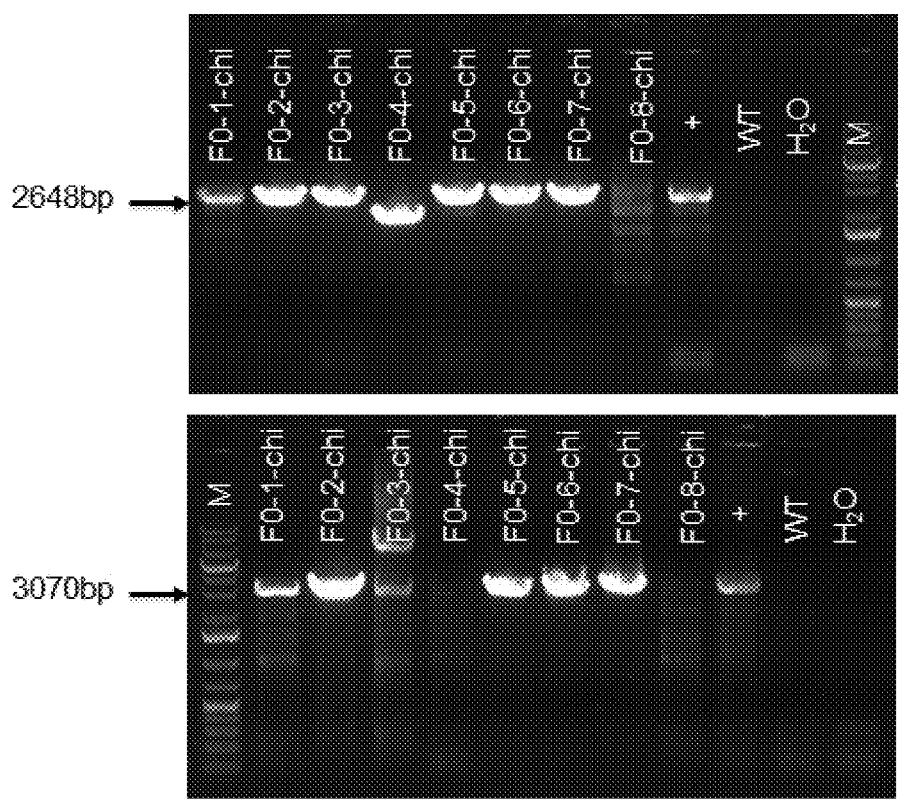
FIG. 6B shows PCR identification results of samples collected from tails of F0 generation mice (chiPD-1 version). WT is wildtype. Mice labeled with F0-1-chi, F0-2-chi, F0-3-chi, F0-5-chi, F0-6-chi, and F0-7-chi were positive.

The results for F0 generation mice (chiPD-1 version) are shown in FIG. 6B. Among them, F0-1-chi, F0-2-chi, F0-3-chi, F0-5-chi, F0-6-chi and F0-7-chi were positive.

2. Genotype Determination for F1 Generation Mice

F0 generation mice were mated with wild-type C57BL/6 mice to obtain F1 generation mice. PCR analysis was performed on the F1 generation mouse tail genomic DNA. PCR conditions and primers were described in the experiments above.

Figure 7A:
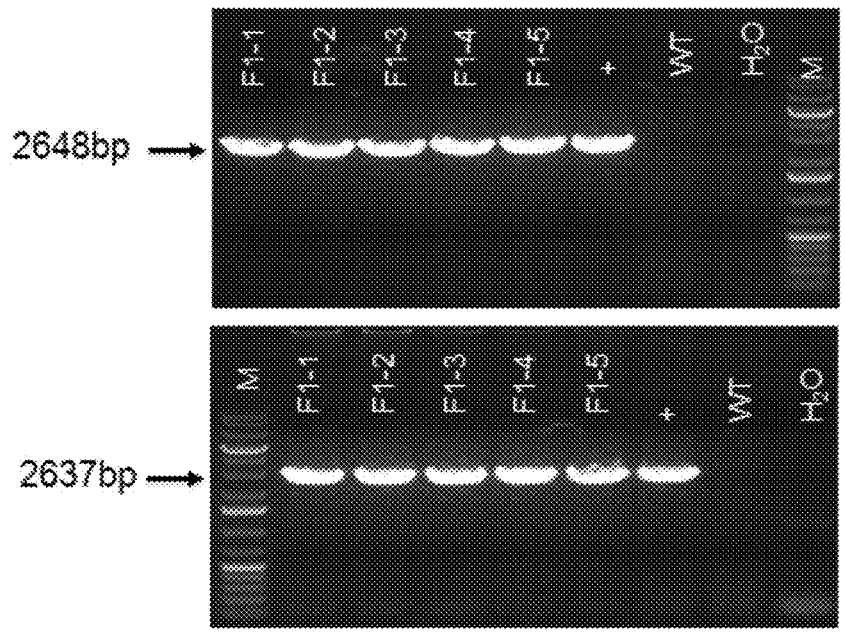
FIG. 7A shows PCR identification results of samples collected from tails of F1 generation mice (huPD-1 version). WT is wildtype. Mice labeled with F1-1, F1-2, F1-3, F1-4, F1-5 were positive.
Figure 7B:
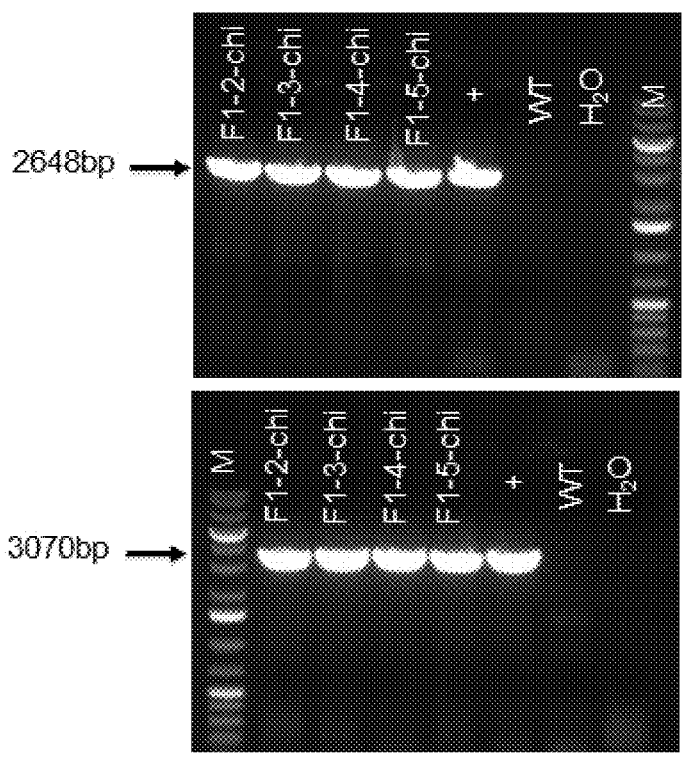
FIG. 7B shows PCR identification results of samples collected from tails of F0 generation mice (chiPD-1 version). WT is wildtype. Mice labeled with F1-2-chi, F1-3-chi, F1-4-chi, and F1-5-chi were positive.

The PCR results (FIGS. 7A-7B) were consistent with expectations, showing that five F1 mice (huPD-1 version) (numbered F1-1, F1-2, F1-3, F1-4, F1-5, respectively) and four F1 generations mice (chiPD-1 version) (numbered: F1-2-chi, F1-3-chi, F1-4-chi, F1-5-chi) were positive, indicating that this method can be used to construct a mouse that can stably pass human or chimeric PD-1 gene to the next generation.

These F1 positive mice were further tested by Southern blot to determine whether there was any random insertions. The genomic DNA was extracted from the mouse tail, and was digested with AseI or ScaI restriction enzymes. The electrophoresis-separated DNA fragments were transferred to a filter membrane and hybridization was performed. Probes P1, P2 are located on the outside of the 3' homology arm and on the WPRE fragment, respectively. The sequences for the probes are shown below:

```
P1-F (SEQ ID NO: 27):
5'-tcaacctcccaatgctaaccagaac-3'

P1-R (SEQ ID NO: 28):
5'-cagactgttggatcaagtgctgtct-3'

P2-F (SEQ ID NO: 29):
5'-gtggatacgctgctttaatgcc-3'

P2-R (SEQ ID NO: 30):
5'-aagggagatccgactcgtctgag-3'
```

Hybridization with P1 probe will only produce a 14.3 kb band in the wild-type C57BL/6 mouse, and hybridization with P2 probe will not produce any bands in the wild-type C57BL/6 mouse. In contrast, hybridization with P1 probe can produce 6.6 kb band in the genetically engineered homozygous mice, and hybridization with P2 probe can produce 4.0 kb band in the genetically engineered homozygous mice. Thus, in the heterozygous mice, hybridization with P1 probe and P2 probe can produce 14.3 kb+6.6 kb bands (P1 probe) and 4.0 kb band (P2 probe).

Figure 8A:
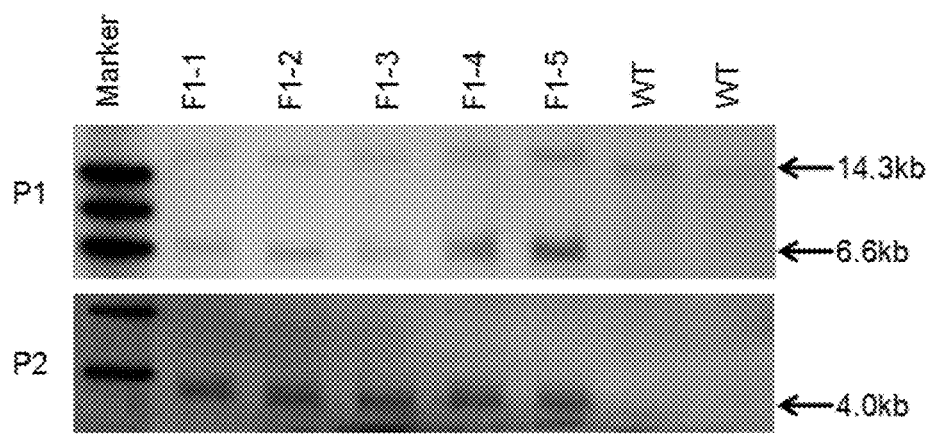
FIG. 8A shows Southern blot results for F1 generation mice (huPD-1 version). Mice labeled with F1-1, F1-2, F1-3, F1-4, F1-5 were positive and had no random insertions.
Figure 8B:
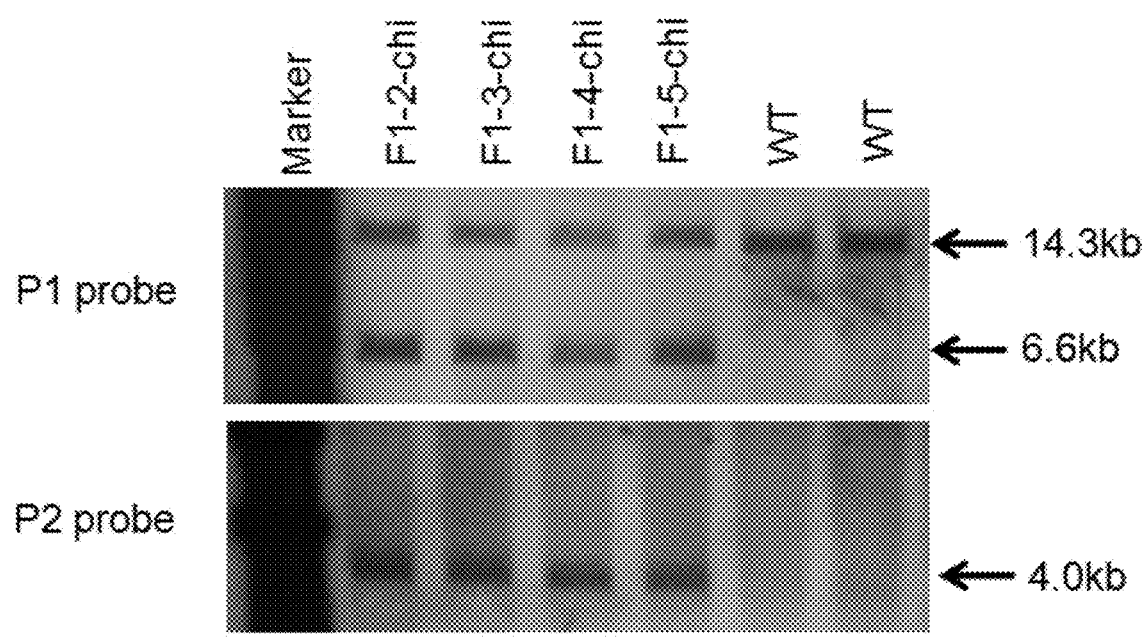
FIG. 8B shows Southern blot results for F1 generation mice (chiPD-1 version). Mice labeled with F1-2-chi, F1-3-chi, F1-4-chi, and F1-5-chi were positive and had no random insertions.

The Southern blot results for F1 generation mice (huPD-1 version) are shown in FIG. 8A. The results showed that none of the five mice (F1-1, F1-2, F1-3, F1-4, and F1-5) had random insertions. The Southern blot results for F1 generation mice (chiPD-1 version) are shown in FIG. 8B. The results showed that none of the four mice (F1-2-chi, F1-3-chi, F1-4-chi, and F1-5-chi) had random insertions. The result indicates that this method can be used to construct a humanized engineered PD-1 gene that can be stably passed to the next generation without random insertion.

3. Expression Level Analysis in Humanized Mice (huPD-1 Version)

One humanized F1 heterozygous mouse (huPD-1 version) was selected. Two wildtype mice with the same background were used as the controls.

7.5 μg of anti-mCD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS.

Figures 9A, 9B, 9C, 9D, 9E, 9F, 9G, 9H, 9I:
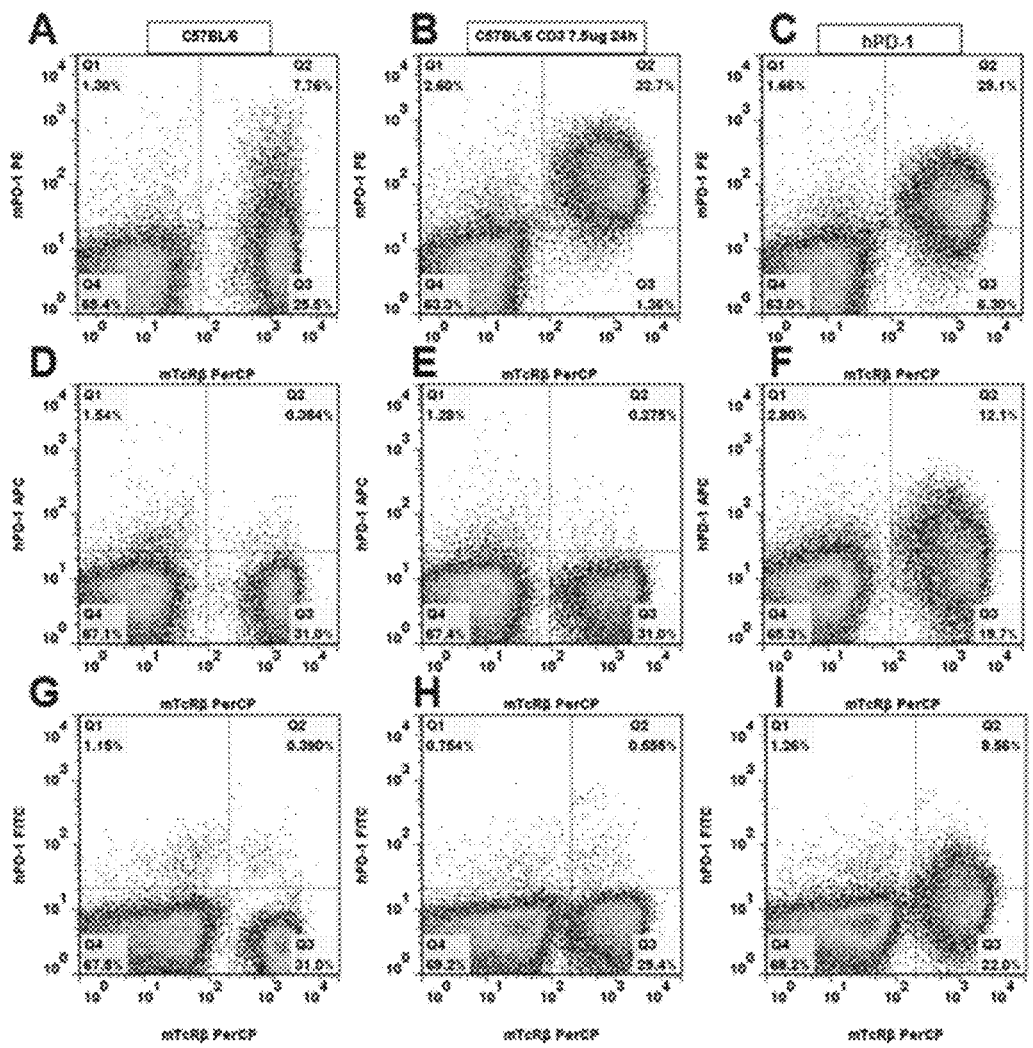
FIGS. 9A-9I are flow cytometry results of wildtype mice (FIGS. 9A, 9B, 9D, 9E, 9G 9H) and heterozygous humanized PD-1 mice (huPD-1 version) (FIGS. 9C, 9F, 9I). Anti-mCD3 antibody was used to activate spleen cells. Flow cytometry was performed with antibody against mouse PD-1 (mPD-1PE) (FIGS. 9A-9C), antibody against human PD-1 (hPD-1 APC) (FIGS. 9D-9F), or antibody against human PD-1 (hPD-1 FITC) (FIGS. 9G-9I). In the wildtype mice, spleen cells that express human or humanized PD-1 were not detected. Human PD-1 was detected on spleen cells in heterozygous humanized PD-1 mice.

PerCP/Cy55 anti-mouse TCR beta chain antibody (mTcRβ PerCP) and PE anti-mouse CD279 (PD-1) antibody (mPD-1 PE), APC anti-human CD279 (hPD-1APC), or FITC anti-human CD279 (PD-1) antibody (hPD-1 FITC) were used to stain cells. In the control groups, spleen cells that express human or humanized PD-1 were not detected. Human PD-1 was detected on spleen cells in heterozygous humanized PD-1 mice (FIGS. 9F and 9I).

Figures 11A, 11B, 11C:
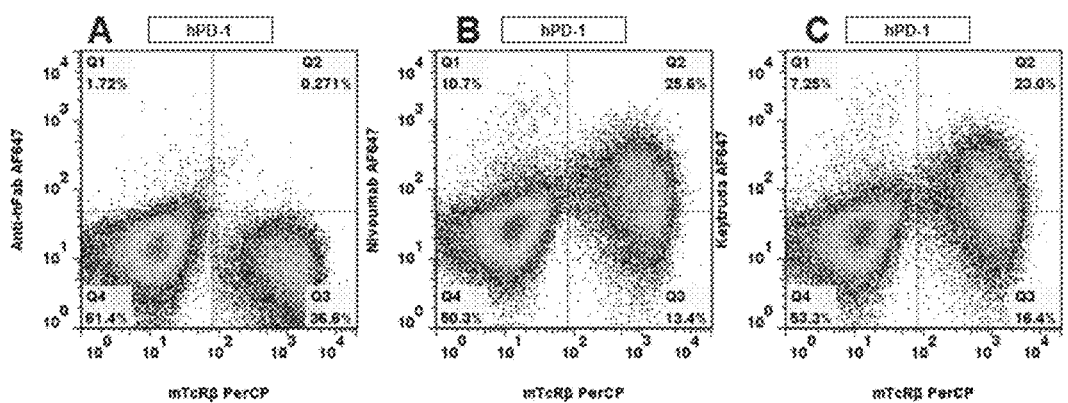
FIGS. 11A-11C are flow cytometry results of spleen cells of heterozygous humanized PD-1 mice (huPD-1 version) after stimulation. Anti-hPD-1 antibodies Nivolumab (FIG. 11B) and Keytruda (FIG. 11C) have good binding affinities with these T cells.

Spleen cells of heterozygous humanized PD-1 mice (huPD-1 version) were also collected and treated with mTcRβ PerCP and anti-hPD-1 antibodies Nivolumab (FIG. 11B) or Keytruda (FIG. 11C). The cells were then treated with anti-Fab AF647 antibody (Alexa Fluor® 647 AffiniPure F(ab')2 Fragment Goat Anti-Human IgG, Fcγ Fragment Specific). The results show that Nivolumab and Keytruda had good binding affinities with human PD-1 that were expressed on these cells.

4. Expression Level Analysis in Humanized Mice (chiPD-1 Version)

One humanized F1 heterozygous mouse (chiPD-1 version) was selected. Two wildtype mice with the same background were used as the controls.

7.5 μg of anti-mCD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS.

Figures 10A, 10B, 10C, 10D, 10E, 10F:
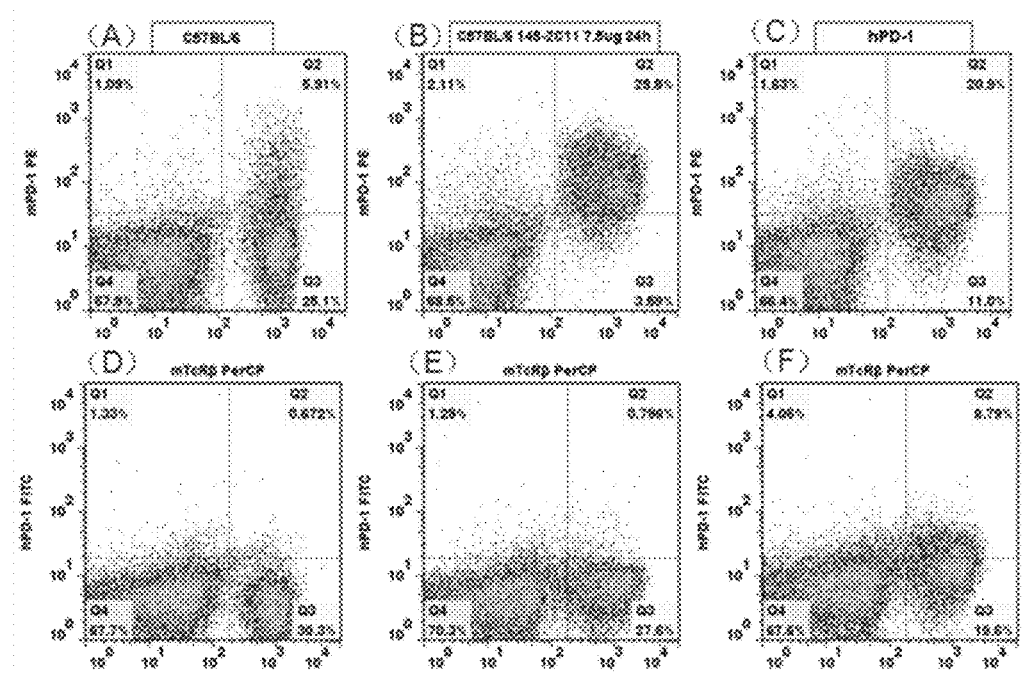
FIGS. 10A-10F are flow cytometry results of wildtype mice (FIGS. 10A, 10B, 10D, 10E) and heterozygous humanized PD-1 mice (chiPD-1 version) (FIGS. 10C, 10F). Anti-mCD3 antibody was used to activate spleen cells. Flow cytometry was performed with antibody against mouse PD-1 (mPD-1PE) (FIGS. 10A-10C), or antibody against human PD-1 (hPD-1 APC) (FIGS. 10D-10F). In the wildtype mice, spleen cells that express human or humanized PD-1 were not detected. Humanized PD-1 was detected on spleen cells in heterozygous humanized PD-1 mice.

PerCP/Cy55 Anti-mouse TCR Beta Chain Antibody (mTcRβ PerCP) and PE anti-mouse CD279 (PD-1) antibody (mPD-1 PE) or FITC anti-human CD279 (PD-1) antibody (hPD-1 FITC) were used to stain cells. In the control groups, spleen cells that express human or humanized PD-1 were not detected. Humanized PD-1 was detected on spleen cells in heterozygous humanized PD-1 mice (FIG. 10F).

Figures 12A, 12B, 12C:
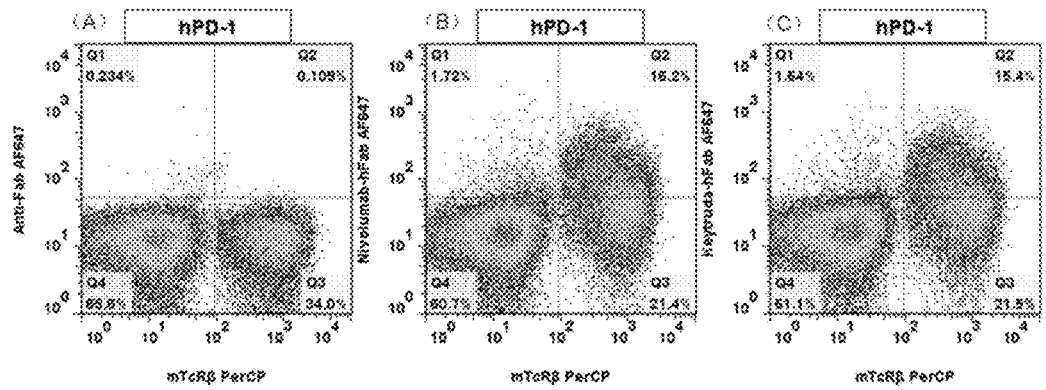
FIGS. 12A-12C are flow cytometry results of spleen cells of heterozygous humanized PD-1 mice (chiPD-1 version) after stimulation. Anti-hPD-1 antibodies Nivolumab (FIG. 12B) and Keytruda (FIG. 12C) have good binding affinities with these T cells.

Spleen cells of heterozygous humanized PD-1 mice (chiPD-1 version) were also collected and treated with mTcRβ PerCP and anti-hPD-1 antibodies Nivolumab (FIG. 12B) or Keytruda (FIG. 12C). The cells were then treated with anti-Fab AF647 antibody (Alexa Fluor® 647 AffiniPure F(ab')2 Fragment Goat Anti-Human IgG, Fcγ Fragment Specific). The results show that Nivolumab and Keytruda had good binding affinities with the chimeric PD-1 proteins that were expressed on these cells.

5. RT-PCR

RNA was extracted from the spleen cells of wild-type C57BL/6 mice and humanized PD-1 heterozygous mice. cDNAs were then obtained by reverse transcription using a reverse transcription kit.

```
mPD-1 RT-PCR F3:
                                          (SEQ ID NO: 31)
5'-CCTGGCTCACAGTGTCAGAG-3'
and mPD-1 RT-PCR R3:
                                          (SEQ ID NO: 32)
5'-CAGGGCTCTCCTCGATTTTT-3'
were used amplify mouse PD-1 fragment of 297 bp.

hPD-1 RT-PCR F3:
                                          (SEQ ID NO: 37)
5'-CCCTGCTCGTGGTGACCGAA-3',
and
```

```
-continued
hPD-1 RT-PCR R3:
                                          (SEQ ID NO: 38)
5'-GCAGGCTCTCTTTGATCTGC-3'
were used amplify human PD-1 fragment of 297 bp.
```

PCR reaction system was 20 reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 13A:
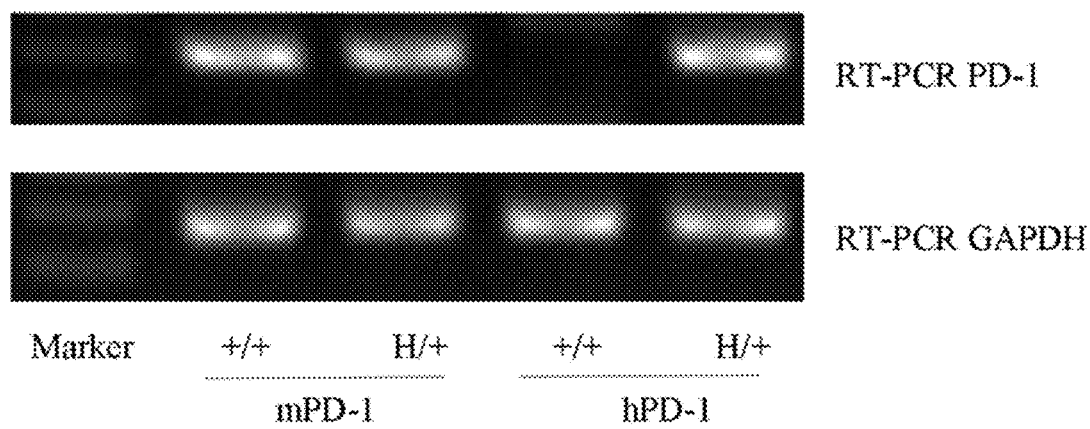
FIG. 13A show results from RT-PCR experiments using primers targeting human PD-1 mRNA sequence and mouse PD-1 mRNA sequence. +/+ indicates wildtype mice; H/+ indicates the F1 generation humanized mouse (human PD1 version); and GAPDH was used as a control.
Figure 13B:
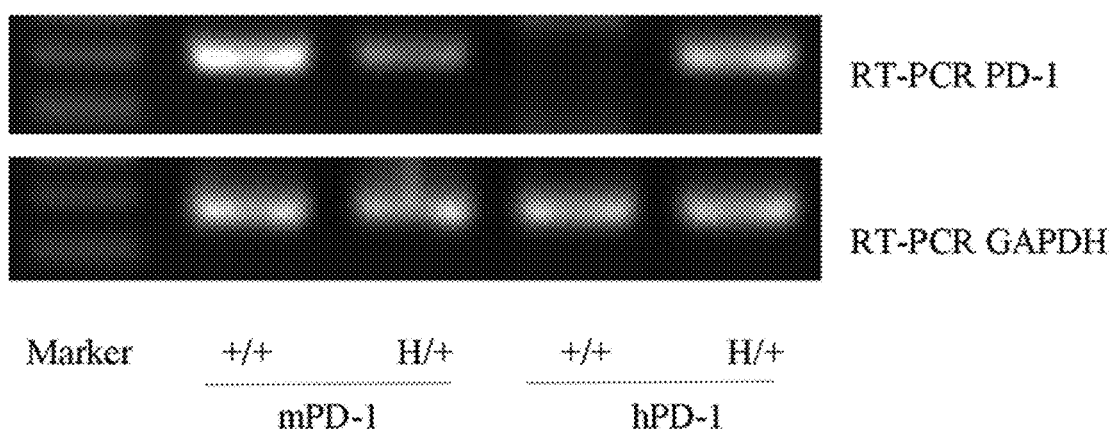
FIG. 13B show results from RT-PCR experiments using primers targeting human PD-1 mRNA sequence and mouse PD-1 mRNA sequence. +/+ indicates wildtype mice; H/+ indicates the F1 generation humanized mouse (chimeric PD1 version); and GAPDH was used as a control.

The results are shown in FIGS. 13A-13B. The mRNA expression of mouse PD-1 can be detected in wild-type C57BL/6 mice and heterozygous mice with human or chimeric PD-1 gene. The mRNA expression of human or humanized PD-1 gene can only be detected in heterozygous mice with human PD-1 gene (huPD-1 version; FIG. 13A) or heterozygous mice with chimeric PD-1 gene (chiPD-1 version; FIG. 13B).

Example 7. Pharmacological Validation of Humanized Animal Model

Homozygous Mice with Human PD-1 Gene (huPD-1 Version)

Homozygous mice (5-8 weeks) with human PD-1 gene were subcutaneously injected with mouse colon cancer cell MC38 ($5 \times 10^5$/100 μl PBS), and when the tumor volume grew to about 100 mm$^3$, the mice were divided to a control group and several treatment groups based on tumor size (n=5/group). The treatment groups were randomly selected for anti-human PD-1 antibody (Nivolumab, Pembrolizumab) treatment at 1 mg/kg, 3 mg/kg, or 10 mg/kg; the control group was injected with an equal volume of blank solvent. The frequency of administration was twice a week (6 times of administrations in total). The tumor volume was measured twice a week and the body weight of the mice was weighed as well. Euthanasia was performed when the tumor volume of the mouse reached 3000 mm$^3$.

Overall, the animals in each group were healthy, and were not significantly different from each other (FIGS. 14 and 15). The tumor in the control group continued growing during the experimental period (FIG. 16); when compared with the control group mice, the tumor volumes in the treatment groups were smaller than the control group (FIG. 16). Thus, the anti-PD-1 antibodies were well tolerated, and the antibodies inhibited the tumor growth in mice.

The table below shows results for this experiment, including the tumor volumes at the day of grouping, 11 days after the grouping, and at the end of the experiment (day 18), the survival rate of the mice, the Tumor Growth Inhibition value ($TGI_{TV}$), and the statistical differences (P value) in mouse body weights and tumor volume between the treatment and control groups.

TABLE 5

| | Tumor volume (mm$^3$) | | | Survival | $TGI_{TV}$ % | P 值 | |
|---|---|---|---|---|---|---|---|
| | Day 0 | Day 11 | Day 18 | | | Body weight | Tumor Volume |
| Control G1 | 128 ± 7 | 1270 ± 301 | 2490 ± 602 | 5/5 | N/A | N/A | N/A |
| G2 (Nivolumab, 10 mg/kg) | 128 ± 5 | 247 ± 50 | 314 ± 76 | 5/5 | 87.4 | 0.07 | 0.007 |
| G3 (Nivolumab, 3 mg/kg) | 128 ± 7 | 384 ± 60 | 768 ± 180 | 5/5 | 69.2 | 0.05 | 0.025 |
| G4 (Nivolumab, 1 mg/kg) | 128 ± 12 | 718 ± 172 | 1692 ± 422 | 5/5 | 32.1 | 0.20 | 0.309 |
| G5 (Pembrolizumab, 10 mg/kg) | 128 ± 9 | 381 ± 90 | 813 ± 265 | 5/5 | 67.3 | 0.17 | 0.034 |
| G6 (Pembrolizumab, 3 mg/kg) | 128 ± 9 | 506 ± 51 | 1205 ± 205 | 5/5 | 51.6 | 0.14 | 0.078 |
| G7 (Pembrolizumab, 1 mg/kg) | 128 ± 12 | 681 ± 67 | 1650 ± 221 | 5/5 | 33.7 | 0.45 | 0.227 |

At the end of the experiment (day 18), the body weight of each treatment group was not significantly different from the control groups (p>0.05), indicating that the animals tolerated the anti-hPD-1 antibodies well. With respect to the tumor volume, in the control group (G1), the average tumor volume was 2490±602 mm$^3$. The average tumor volumes in the treatment groups were all smaller than the average tumor volume in the control group.

The results show that anti-human PD-1 antibodies Nivolumab and Pembrolizumab had different tumor inhibitory effects in homozygous mice with human PD-1 gene, and a higher concentration of these antibodies can provide a better efficacy.

Homozygous Mice with Chimeric PD-1 Gene (chiPD-1 Version)

Homozygous mice (5-8 weeks) with chimeric PD-1 gene were subcutaneously injected with mouse colon cancer cell MC38 (5×10⁵/100 μl PBS), and when the tumor volume grew to about 100 mm³, the mice were divided to a control group and several treatment groups based on tumor size (n=5/group). The treatment groups were randomly selected for anti-human PD-1 antibodies (Nivolumab, Pembrolizumab) treatment at 1 mg/kg, 3 mg/kg, or 10 mg/kg; the control group was injected with an equal volume of blank solvent. The frequency of administration was twice a week (6 times of administrations in total). The tumor volume was measured twice a week and the body weight of the mice was weighed as well. Euthanasia was performed when the tumor volume of the mouse reached 3000 mm³.

Overall, the animals in each group were healthy, and the weights were not obviously different from each other (FIGS. 17 and 18). The tumor in the control group continued growing during the experimental period (FIG. 19); when compared with the control group mice, the tumor volumes in the treatment groups were smaller than the control group (FIG. 19). Thus, the anti-PD-1 antibodies were well tolerated, and the antibodies can inhibit the tumor growth in mice.

The table below shows results for this experiment, including the tumor volumes at the day of grouping, 11 days after the grouping, and at the end of the experiment (day 17), the survival rate of the mice, the Tumor Growth Inhibition value ($TGI_{TV}$), and the statistical differences (P value) in mouse body weights and tumor volume between the treatment and control groups.

humanized PD-1 genes (e.g., with partially humanized PD-1 sequence) cannot be necessarily used as an effective animal model to test the efficacy and the toxicity of various anti-hPD-1 antibodies (e.g., Nivolumab and/or Pembrolizumab). The above examples have demonstrated that the two mouse models as described in the examples (huPD-1 version and chiPD-1 version) can be used as an effective in vivo animal model for screening, evaluating human PD-1 signaling pathway regulators, and testing the efficacy and toxicities of multiple anti-human PD-1 antibodies.

Example 8: Mice with Two or More Humanized Genes

Mice with the human or chimeric PD-1 gene (e.g., animal model with human or chimeric PD-1 prepared using the methods as described in the present disclosure) can also be used to prepare an animal model with double-humanized or multi-humanized genes. For example, in Example 5, the embryonic stem cell used in the microinjection and embryo transfer process can be selected from the embryos of other genetically modified mice, so as to obtain double- or multiple-gene modified mouse models. The fertilized eggs of mice with human or chimeric PD-1 gene can also be further genetically engineered to produce mouse lines with one or more humanized or otherwise genetically modified mouse models. In addition, the genetically engineered PD-1 animal model homozygote or heterozygote can be mated with other

TABLE 6

| | Tumor volume (mm³) | | | Survival | $TGI_{TV}$% | P值 | |
|---|---|---|---|---|---|---|---|
| | Day 0 | Day 14 | Day 17 | | | Body weight | Tumor Volume |
| Control G1 | 156 ± 5 | 1395 ± 174 | 1912 ± 126 | 5/5 | N/A | N/A | N/A |
| G2 (Nivolumab, 10 mg/kg) | 156 ± 6 | 359 ± 68 | 466 ± 119 | 5/5 | 82.3 | 0.10 | 3.23E−05 |
| G3 (Nivolumab, 3 mg/kg) | 156 ± 9 | 367 ± 49 | 468 ± 43 | 5/5 | 82.2 | 0.13 | 4.63E−06 |
| G4 (Nivolumab, 1 mg/kg) | 156 ± 25 | 733 ± 152 | 997 ± 211 | 5/5 | 52.1 | 0.40 | 0.006 |
| G5 (Pembrolizumab, 10 mg/kg) | 156 ± 7 | 243 ± 107 | 239 ± 104 | 5/5 | 95.3 | 0.06 | 7.10E−06 |
| G6 (Pembrolizumab, 3 mg/kg) | 156 ± 12 | 361 ± 105 | 460 ± 145 | 5/5 | 82.7 | 0.02 | 6.63E−05 |
| G7 (Pembrolizumab, 1 mg/kg) | 156 ± 10 | 413 ± 37 | 577 ± 91 | 5/5 | 76.0 | 0.10 | 2.59E−05 |

At the end of the experiment (day 17), the body weights of the three groups that were treated with Pembrolizumab were smaller than the body weight of the control group. With respect to the tumor volume, in the control group (G1), the average tumor volume was 1912±126 mm³. The average tumor volumes in the treatment groups were all smaller than the average tumor volume in the control group. And the tumor size in the chiPD-1 version mice treated with Pembrolizumab were also much smaller than the tumor size in the huPD-1 version mice that were treated with Pembrolizumab with the same dosage. The results suggest that the cytoplasmic region of human PD-1 may not function as well as the cytoplasmic region of endogenous PD-1 in non-human animal cells.

The results show that anti-human PD-1 antibodies Nivolumab and Pembrolizumab had different tumor inhibitory effects in homozygous mice with human PD-1 gene, and a higher concentration of these antibodies also can lead to better efficacy.

Because of the difference between human PD-1 and mouse PD-1 proteins, anti-hPD-1 antibodies cannot necessarily bind to the mouse PD-1 protein. Thus, a mouse model with endogenous PD-1 genes, even a mouse model with genetically modified homozygous or heterozygous animal models (or through IVF), and the progeny can be screened. According to the Mendelian law, there is a chance to obtain the double-gene or multiple-gene modified heterozygous animals, and then the heterozygous animals can be further mated with each other to finally obtain the double-gene or multiple-gene modified homozygotes.

In the case of generating double humanized PD-1/OX40 mice, since the mouse PD-1 gene and OX40 gene are located on different chromosomes, the double humanized PD-1/OX40 mouse model can be obtained by crossing the PD-1 humanized mice with OX40 humanized mice. The heterozygous animals can be mated with each other to finally obtain the double-gene or multiple-gene modified homozygotes.

Example 9. Methods Based On Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Based on the PD-1 transcript and the humanized PD-1 mouse gene map as shown in FIGS. 2A-2B, a targeting strategy for generating the humanized PD-1 mouse model with Embryonic Stem Cell Technologies is developed (FIGS. 3A and 3B). Since the goal is to replace exon 1 of the mouse PD-1 gene in whole or in part with the human PD-1 gene or the chimeric PD-1 gene, a recombinant vector that contains a 5' homologous arm, a 3' homologous arm, and a sequence fragment from human PD-1 or chimeric PD-1 gene is designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm.

Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (e.g., neo), and then the PD-1 gene humanized homozygous mice can be obtained by mating these mice with each other. The methods of genotyping and using the F1 heterozygous mice or F2 homozygous mice are similar to the methods as described in the examples above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse, whose genome comprises (1) an insertion of a sequence encoding a human or humanized programmed cell death protein 1 (PD-1) at endogenous PD-1 gene exon 1, and (2) endogenous PD-1 gene exons 2-5, wherein the mouse expresses the human or humanized PD-1 protein on the surface of one or more spleen cells after the mouse is stimulated by an anti-CD3 antibody.

2. The mouse of claim 1, wherein the sequence encoding the human or humanized PD-1 is operably linked to an endogenous regulatory element at the endogenous PD-1 gene locus.

3. The mouse of claim 1, wherein the sequence encoding the human or humanized PD-1 comprises a sequence encoding an amino acid sequence that is at least 95% identical to SEQ ID NO: 35.

4. The mouse of claim 1, wherein the sequence encoding the human or humanized PD-1 comprises a sequence encoding an amino acid sequence that is at least 96% identical to SEQ ID NO: 33.

5. The mouse of claim 1, wherein the sequence encoding the human or humanized PD-1 is operably linked to a Woodchuck Hepatitis Virus (WHP) Posttranscriptional Regulatory Element and/or a polyA (polyadenylation) signal sequence.

6. The mouse of claim 1, wherein the mouse does not express endogenous PD-1.

7. The mouse of claim 1, wherein the genome of the mouse further comprises a deletion of one or more nucleotides in exon 1 of an endogenous PD-1 gene at the endogenous PD-1 gene locus.

8. The mouse of claim 1, wherein the genome of the mouse comprises the entire endogenous PD-1 gene 5'-UTR.

9. The mouse of claim 1, wherein the humanized PD-1 comprises SEQ ID NO: 33.

10. A genetically-modified mouse, whose genome comprises (1) a replacement of one or more nucleotides in exon 1 of an endogenous PD-1 gene with a sequence encoding a human or humanized PD-1 and (2) exons 2-5 of the endogenous PD-1 gene, wherein the mouse expresses the human or humanized PD-1 protein on the surface of one or more spleen cells after the mouse is stimulated by an anti-CD3 antibody.

11. The mouse of claim 10, wherein the sequence encoding the human or humanized PD-1 is immediately located downstream of the entire 5'-UTR at the endogenous PD-1 locus.

12. The mouse of claim 10, wherein the mouse has one or more spleen cells expressing a humanized PD-1 having a humanized extracellular region, a mouse transmembrane region, and a mouse cytoplasmic region.

13. The mouse of claim 10, wherein the mouse is homozygous with respect to the replacement at the endogenous PD-1 gene locus.

14. The mouse of claim 10, wherein the humanized PD-1 comprises an amino acid sequence that is at least 96% identical to SEQ ID NO: 33.

15. The mouse of claim 10, wherein the humanized PD-1 comprises SEQ ID NO: 33.

* * * * *

SEQUENCE LISTING

```
<160> NUMBER OF SEQ ID NOS: 40

<210> SEQ ID NO 1
<211> LENGTH: 1972
<212> TYPE: DNA
<213> ORGANISM: Mus musculus

<400> SEQUENCE: 1
tgagcagcgg ggaggaggaa gaggagactg ctactgaagg cgacactgcc aggggctctg      60
ggcatgtggg tccggcaggt accctggtca ttcacttggg ctgtgctgca gttgagctgg     120
caatcagggt ggcttctaga ggtccccaat gggccctgga ggtccctcac cttctaccca     180
gcctggctca cagtgtcaga gggagcaaat gccaccttca cctgcagctt gtccaactgg     240
tcggaggatc ttatgctgaa ctggaaccgc ctgagtccca gcaaccagac tgaaaaacag     300
gccgccttct gtaatggttt gagccaaccc gtccaggatg cccgcttcca gatcatacag     360
ctgcccaaca ggcatgactt ccacatgaac atccttgaca cacggcgcaa tgacagtggc     420
atctacctct gtgggggccat ctccctgcac cccaaggcaa aaatcgagga gagccctgga     480
gcagagctcg tggtaacaga gagaatcctg gagacctcaa caagatatcc cagcccctcg     540
cccaaaccag aaggccggtt tcaaggcatg gtcattggta tcatgagtgc cctagtgggt     600
atccctgtat tgctgctgct ggcctgggcc ctagctgtct tctgctcaac aagtatgtca     660
gaggccagag gagctggaag caaggacgac actctgaagg aggagccttc agcagcacct     720
gtccctagtg tggcctatga ggagctggac ttccagggac gagagaagac accagagctc     780
```

```
cctaccgcct gtgtgcacac agaatatgcc accattgtct tcactgaagg gctgggtgcc      840
tcggccatgg gacgtagggg ctcagctgat ggcctgcagg gtcctcggcc tccaagacat      900
gaggatggac attgttcttg gcctctttga ccagattctt cagccattag catgctgcag      960
accctccaca gagagcaccg gtccgtccct cagtcaagag gagcatgcag gctacagttc     1020
agccaaggct cccagggtct gagctagctg gagtgacagc ccagcgcctg caccaattcc     1080
agcacatgca ctgttgagtg agagctcact tcaggtttac cacaagctgg gagcagcagg     1140
cttcccggtt tcctattgtc acaaggtgca gagctggggc ctaagcctat gtctcctgaa     1200
tcctactgtt gggcacttct agggacttga gacactatag ccaatggcct ctgtgggttc     1260
tgtgcctgga atggagaga tctgagtaca gcctgctttg aatggccctg tgaggcaacc     1320
ccaaagcaag gggtccagg tatactatgg gcccagcacc taaagccacc cttgggagat     1380
gatactcagg tgggaaattc gtagactggg ggactgaacc aatcccaaga tctggaaaag     1440
ttttgatgaa gacttgaaaa gctcctagct tcggggtct gggaagcatg agcacttacc     1500
aggcaaaagc tccgtgagcg tatctgctgt ccttctgcat gcccaggtac ctcagttttt     1560
ttcaacagca aggaaactag ggcaataaag ggaaccagca gagctagagc cacccacaca     1620 tccaggggge acttgactct ccctactcct cctaggaacc aaaaggacaa agtccatgtt     1680
gacagcaggg aaggaaggg ggatataacc ttgacgcaaa ccaacactgg ggtgttagaa     1740
tctcctcatt cactctgtcc tggagttggg ttctggctct ccttcacacc taggactctg     1800
aaatgagcaa gcacttcaga cagtcagggt agcaagagtc tagctgtctg gtgggcaccc     1860
aaaatgacca gggcttaagt ccctttcctt tggtttaagc ccgttataat taaatggtac     1920
caaaagcttt aaaaaaaaaa aaaaaaaaaa aaaaaaaaaa aaaaaaaaaa aa             1972
```

<210> SEQ ID NO 2
<211> LENGTH: 288
<212> TYPE: PRT
<213> ORGANISM: Mus musculus

<400> SEQUENCE: 2

```
Met Trp Val Arg Gln Val Pro Trp Ser Phe Thr Trp Ala Val Leu Gln
 1               5                  10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
```

```
                165                 170                 175
Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 3
<211> LENGTH: 867
<212> TYPE: DNA
<213> ORGANISM: Artificial Sequence
<220> FEATURE:
<223> OTHER INFORMATION: Homo sapiens and Mus musculus

<400> SEQUENCE: 3
atgcagatcc acaggcgcc ctggccagtc gtctgggcgg tgctacaact gggctggcgg      60
ccaggatggt tcttagactc cccagacagg ccctggaacc ccccaccctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccaccccag ccctcacccc    480
aggccagccg gccagttcca aaccctggtg gttggtgtcg tgggcggcct gctgggcagc    540
ctggtgctgc tagtctgggt cctggccgtc atctgctccc gggccgcacg agggacaata    600
ggagccaggg gcaccggcca gcccctgaag gaggacccct cagccgtgcc tgtgttctct    660
gtggactatg gggagctgga tttccagtgg cgagagaaga cccggagcc cccgtgccc     720 tgtgtccctg agcagacgga gtatgccacc attgtctttc tagcggaat gggcacctca    780 tccccgccc cagggctc agctgacggc cctcggagtg cccagccact gaggcctgag    840
gatggacact gctcttggcc cctctga                                        867

<210> SEQ ID NO 4
<211> LENGTH: 867
<212> TYPE: DNA
<213> ORGANISM: Artificial Sequence
<220> FEATURE:
<223> OTHER INFORMATION: Homo sapiens and Mus musculus

<400> SEQUENCE: 4
atgcagatcc acaggcgcc ctggccagtc gtctgggcgg tgctacaact gggctggcgg      60
ccaggatggt tcttagactc cccagacagg ccctggaacc ccccaccctt ctccccagcc    120
ctgctcgtgg tgaccgaagg ggacaacgcc accttcacct gcagcttctc caacacatcg    180
```

-continued

```
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aaggcgcaga tcaaagagag cctgcgggca    420
gagctcaggg tgacagagag aagggcagaa gtgcccacag cccaccccag cccctcaccc    480
aggccagccg ccagttccaa ggcatggtc attggtatca tgagtgccct agtgggtatc     540
cctgtattgc tgctgctggc ctgggcccta gctgtcttct gctcaacaag tatgtcagag    600
gccagaggag ctggaagcaa ggacgacact ctgaaggagg agccttcagc agcacctgtc    660
cctagtgtgg cctatgagga gctggacttc cagggacgag agaagacacc agagctccct    720
accgcctgtg tgcacacaga atatgccacc attgtcttca ctgaagggct gggtgcctcg    780
gccatgggac gtaggggctc agctgatggc ctgcagggtc ctcggcctcc aagacatgag    840
gatggacatt gttcttggcc tctttga                                        867
```

<210> SEQ ID NO 5
<211> LENGTH: 589
<212> TYPE: DNA
<213> ORGANISM: Artificial Sequence
<220> FEATURE:
<223> OTHER INFORMATION: Synthesized sequence
<400> SEQUENCE: 5

```
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240 ggttggggca ttgccaccac ctgtcagctc ctttccggga cttttcgcttt ccccctccct   300 attgccacgg cggaactcat cgccgcctgc cttgcccgct gctggacagg ggctcggctg    360
ttgggcactg acaattccgt ggtgttgtcg gggaaatcat cgtccttttcc ttggctgctc   420 gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc cttttgggccg cctccccgc               589
```

<210> SEQ ID NO 6
<211> LENGTH: 208
<212> TYPE: DNA
<213> ORGANISM: Artificial Sequence
<220> FEATURE:
<223> OTHER INFORMATION: Synthesized sequence
<400> SEQUENCE: 6

```
ctgtgccttc tagttgccag ccatctgttg tttgccccctc ccccgtgcct tccttgaccc    60
tggaaggtgc cactcccact gtcctttcct aataaaatga ggaaattgca tcgcattgtc    120
tgagtaggtg tcattctatt ctgggggggtg gggtggggca ggacagcaag ggggaggatt    180
gggaagacaa tagcaggcat gctgggga                                       208
```

<210> SEQ ID NO 7
<211> LENGTH: 1400
<212> TYPE: DNA
<213> ORGANISM: Artificial Sequence
<220> FEATURE:
<223> OTHER INFORMATION: Mus musculus

```
<400> SEQUENCE: 7
gtcttgctac cctgagcatg ccagaaagac ataaaggtat aaaggaggct ctgtaacagc    60
caggcgtggg gaggggatcc ccctagcttc tgcccacagg ccccatgctg agactggagg   120
cggccagtct gtgcctcaca ctcttttttcc atttctgtgc tgttcaaagt aatgtttcct   180
tccccaccaa gctagtgcct ctgaacctgg gtggctgagg cagttgccag atggtttcca   240
ggcgggctgc ctattttagg gtggtgagac ccacacatct cattgctaat attagcagtt   300
tcgttttccc ttttttttccc attcactgtg gcgaaacaca gagagcagaa tgattaaatc   360
atcagaatgc cccagaaatg actagccagc caggtactat gcatgcacac aagtcggccc   420
accccaccta atcccagaga gacaagcagg aggtgaggtg ggcctccacc tcctagggac   480
tgaggaaagt tgactgggaa agacctagaa attgagtcta ccccagcctg gtgttaggtt   540
tttctcaggg gaagagaaag atgcagggca gcagagctag caaacctaag acaactatag   600
aagcagagaa acagtgaga tccgggcagc agatccagca tcttgaaagg aagaaaagcc   660
ttaagagaaa gcaagaccag gcccagggtc tttctgaacc tacaggggtg tctggagagg   720
aaaggcatcg tctcgggtcc taggaaatgt tcactatagc ccttcgaggc ctcctctgac   780
ccatcaaacg ggagcatgtg ggatagctgg gctcttgctc ctcagtagta aaggactaag   840
gcatagctca gggcattcaa ggccacgcat ggcagacaag gtaggggagg gtccagcttg   900
ccctcgctgc ggccataggt accaaagcca ggcctcgaca cccacccctcc aaagggacaa   960 gagtctggcc ctagtttcag tctctctcag ccctgggagc taaggctcga tcggggtacc  1020
aggaatggaa aagaccaaac ctacccacaa gaggggctag aaatggagag acccccatag  1080
caggacaaga ggcaaggaca gctagtcaga gagaaccccc cctctctgct ccccaatctc  1140
tcactagtcc cttacctgct cctcccaggc atcgttccct cccactcccc tccccccttcc  1200 atgcccctcc cccacctcta gttgcctgtt ctcccaccct tgtggaggtg gaggaagagg  1260
gggcgggagc caagaacagg tctcctccct ccaacatgac ctgggacagt ttccttttccg  1320 ctacagacaa ctctgcctga gcagcgggga ggaggaagag gagactgcta ctgaaggcga  1380
cactgccagg ggctctgggc                                              1400

<210> SEQ ID NO 8
<211> LENGTH: 1400
<212> TYPE: DNA
<213> ORGANISM: Artificial Sequence
<220> FEATURE:
<223> OTHER INFORMATION: Mus musculus

<400> SEQUENCE: 8
gtatgtggct cctagggatg tgggatcaat tggggttggt ggctggggca gggcttgaag    60
aaacgttcac cctcggttcc tattactgga ggggaggaac acctgtgtcc ctggttacac   120
ggattggctc ctggttacac agattggctt taggtgggtt ttacaggtga aatgcccct   180 ggggctcaaa atccaccccc tccttgcttt tagacagaca gaacatttat ctaacgtcag   240
ttgatcttct gtgtccctct ctgtgaagcg atggtaggtc tgaacagagc tctgacctca   300
gccactgctt caggattctg gcaggccctg gtatccttgg cctttctcta tgttttttcta   360 tggttgggga catccctaca tggagcctgc cctacacact gtatagatga ctgaagatcc   420
aagagtataa tcagctgtct accctcatgg acaagcttcc cgtgctagca tttctggggg   480
actcccgagt tcatatccct ggcctcatag catcctgggg gtgggggtg tgtgaaacgg   540
```

-continued

| | |
|---|---|
| agaggtccag gaatcctgct caaattcctc acagtgaaaa cacagctccc tgtactcctt | 600 |
| actcctcact accctgtacc ccttggcccc tgcccaccct ctggactgag ccaaccttca | 660 |
| ctgagaacct ggtcctggga ccagagggaa ctttgtttct cctggatgtc aacaaactcc | 720 |
| taggtcagag ctacacctgc ggcgcatgga attgtggcct agacaagctt atactcttgt | 780 |
| gctgccttaa catctttgac ctgcaatgat gttcctttgc tcatatgacg tcccagtcac | 840 |
| cttcacccca gcctcttcac taccgtgaaa acaggatggg actgggagct gggtgctggg | 900 |
| tgcttaccac cacaggccct ctcctgggtt gcaggctaag gctggttggg aagccaggga | 960 |
| cattttccct ccacgtaccc tcttaagata gcccatggtt tgctgtcaag actggatgga | 1020 |
| ggaaacagac ctgaacatgg tagatggtct gaggccctag ggtgaaagat gtcccttggg | 1080 |
| gaaaccttgt caggaaaccc acggagcaaa gtcggaagga ttatgtgtca ttggagagaa | 1140 |
| gcaactgaga cagaaagggg actatgactc actctggtga cctggcacac tgggcatgtc | 1200 |
| cgcaaatgaa gctttgatga gacaatatgg agatacagat gtatttatgc aggcctactg | 1260 |
| tagattgtct ctgacaaatg tctcaaagtg gcatgcctcc ttcacgacct gaatagctca | 1320 |
| acgtgggaca cctcacaggc cagtgccatt tggcagccgt ggacctttag tctagtgcat | 1380 |
| ttcttcccctc ctgattggcc | 1400 |

<210> SEQ ID NO 9
<211> LENGTH: 1696
<212> TYPE: DNA
<213> ORGANISM: Artificial Sequence
<220> FEATURE:
<223> OTHER INFORMATION: Homo sapiens

<400> SEQUENCE: 9

| | |
|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcaccct gcagcttctc caacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aaggcgcaga tcaaagagag cctgcgggca | 420 |
| gagctcaggg tgacagagag aagggcagaa gtgcccacag cccaccccag cccctcaccc | 480 |
| aggccagccg ccagttccaa accctggtg gttggtgtcg tgggcggcct gctgggcagc | 540 |
| ctggtgctgc tagtctgggt cctggccgtc atctgctccc gggccgcacg agggacaata | 600 |
| ggagccaggc gcaccggcca gcccctgaag gaggacccct cagccgtgcc tgtgttctct | 660 |
| gtggactatg gggagctgga tttccagtgg cgagagaaga cccccgagcc ccccgtgccc | 720 |
| tgtgtccctg agcagacgga gtatgccacc attgtctttc ctagcggaat gggcacctca | 780 |
| tcccccgccc gcaggggctc agctgacggc cctcggagtg cccagccact gaggcctgag | 840 |
| gatggacact gctcttggcc cctctgaaat caacctctgg attacaaaat tgtgaaaga | 900 |
| ttgactggta ttcttaacta tgttgctcct tttacgctat gtggatacgc tgctttaatg | 960 |
| cctttgtatc atgctattgc ttcccgtatg gctttcattt tctcctcctt gtataaatcc | 1020 |
| tggttgctgt ctctttatga ggagttgtgg cccgttgtca ggcaacgtgg cgtggtgtgc | 1080 |
| actgtgtttg ctgacgcaac ccccactggt tggggcattg ccaccacctg tcagctcctt | 1140 |
| tccgggactt tcgctttccc cctccctatt gccacggcgg aactcatcgc cgcctgcctt | 1200 |

-continued

```
gcccgctgct ggacaggggc tcggctgttg ggcactgaca attccgtggt gttgtcgggg    1260
aaatcatcgt cctttccttg gctgctcgcc tgtgttgcca cctggattct gcgcgggacg    1320
tccttctgct acgtcccttc ggccctcaat ccagcggacc ttccttcccg cggcctgctg    1380
ccggctctgc ggcctcttcc gcgtcttcgc cttcgccctc agacgagtcg gatctcccct    1440
tgggccgcct cccgcatcg ataccgtcga cctcgactgt gccttctagt tgccagccat     1500
ctgttgtttg cccctccccc gtgccttcct tgaccctgga aggtgccact cccactgtcc    1560
tttcctaata aaatgaggaa attgcatcgc attgtctgag taggtgtcat tctattctgg    1620
ggggtggggt ggggcaggac agcaaggggg aggattggga agacaatagc aggcatgctg    1680
gggaattaat agtact                                                    1696
```

<210> SEQ ID NO 10
<211> LENGTH: 1740
<212> TYPE: DNA
<213> ORGANISM: Artificial Sequence
<220> FEATURE:
<223> OTHER INFORMATION: Homo sapiens and Mus musculus

<400> SEQUENCE: 10

```
cgacactgcc aggggctctg gcatgcagaa tcccacaggc gccctggcca gtcgtctggg     60
cggtgctaca actgggctgg cggccaggat ggttcttaga ctccccagac aggccctgga    120 accccccca cttctcccca gccctgctcg tggtgaccga aggggacaac gccaccttca     180
cctgcagctt ctccaacaca tcggagagct tcgtgctaaa ctggtaccgc atgagcccca    240
gcaaccagac ggacaagctg gccgccttcc ccgaggaccg cagccagccc ggccaggact    300
gccgcttccg tgtcacacaa ctgcccaacg ggcgtgactt ccacatgagc gtggtcaggg    360
cccggcgcaa tgacagcggc acctacctct gtggggccat ctccctggcc cccaaggcgc    420
agatcaaaga gagcctgcgg gcagagctca ggtgacaga gagaagggca gaagtgccca    480
cagcccaccc cagcccctca cccaggccag ccggccagtt ccaaaccctg gtggttggtg    540
tcgtgggcgg cctgctgggc agcctggtgc tgctagtctg ggtcctggcc gtcatctgct    600
cccgggccgc acgagggaca ataggagcca ggcgcaccgg ccagccctg aaggaggacc     660 cctcagccgt gcctgtgttc tctgtggact atgggagct ggatttccag tggcgagaga     720
agaccccgga gccccgtg ccctgtgtcc ctgagcagac ggagtatgcc accattgtct       780
ttcctagcgg aatgggcacc tcatcccccg cccgcagggg ctcagctgac ggccctcgga    840
gtgcccagcc actgaggcct gaggatggac actgctcttg gccctctga aatcaacctc     900 tggattacaa aatttgtgaa agattgactg gtattcttaa ctatgttgct ccttttacgc    960
tatgtggata cgctgcttta atgccttgt atcatgctat tgcttcccgt atggctttca    1020
ttttctcctc cttgtataaa tcctggttgc tgtctcttta tgaggagttg tggcccgttg    1080
tcaggcaacg tggcgtggtg tgcactgtgt ttgctgacgc aacccccact ggttggggca    1140
ttgccaccac ctgtcagctc ctttccggga ctttcgcttt ccccctccct attgccacgg    1200
cggaactcat cgccgcctgc cttgcccgct gctggacagg gctcggctg ttgggcactg     1260 acaattccgt ggtgttgtcg gggaaatcat cgtcctttcc ttggctgctc gcctgtgttg    1320
ccacctggat tctgcgcggg acgtccttct gctacgtccc ttcggccctc aatccagcgg    1380
accttccttc ccgcggcctg ctgccggctc tgcggcctct tccgcgtctt cgccttcgcc    1440
ctcagacgag tcggatctcc ctttgggccg cctccccgca tcgataccgt cgacctcgac    1500
```

```
tgtgccttct agttgccagc catctgttgt ttgcccctcc cccgtgcctt ccttgaccct    1560
ggaaggtgcc actcccactg tcctttccta ataaaatgag gaaattgcat cgcattgtct    1620
gagtaggtgt cattctattc tgggggtgg ggtggggcag gacagcaagg gggaggattg     1680
ggaagacaat agcaggcatg ctggggaatt aatagtactg tatgtggctc ctagggatgt    1740

<210> SEQ ID NO 11
<211> LENGTH: 23
<212> TYPE: DNA
<213> ORGANISM: Artificial Sequence
<220> FEATURE:
<223> OTHER INFORMATION: PCR primer

<400> SEQUENCE: 11
tctgggcatg tgggtccggc agg                                              23

<210> SEQ ID NO 12
<211> LENGTH: 23
<212> TYPE: DNA
<213> ORGANISM: Artificial Sequence
<220> FEATURE:
<223> OTHER INFORMATION: PCR primer

<400> SEQUENCE: 12
tgtgggtccg gcaggtaccc tgg                                              23

<210> SEQ ID NO 13
<211> LENGTH: 23
<212> TYPE: DNA
<213> ORGANISM: Artificial Sequence
<220> FEATURE:
<223> OTHER INFORMATION: PCR primer

<400> SEQUENCE: 13
ctgcagttga gctggcaatc agg                                              23

<210> SEQ ID NO 14
<211> LENGTH: 23
<212> TYPE: DNA
<213> ORGANISM: Artificial Sequence
<220> FEATURE:
<223> OTHER INFORMATION: PCR primer

<400> SEQUENCE: 14
aggtaccctg gtcattcact tgg                                              23

<210> SEQ ID NO 15
<211> LENGTH: 23
<212> TYPE: DNA
<213> ORGANISM: Artificial Sequence
<220> FEATURE:
<223> OTHER INFORMATION: PCR primer

<400> SEQUENCE: 15
tgaatgacca gggtacctgc cgg                                              23

<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
agttgagctg gcaatcaggg tgg                                              23
```

<210> SEQ ID NO 17
<211> LENGTH: 23
<212> TYPE: DNA
<213> ORGANISM: Artificial Sequence
<220> FEATURE:
<223> OTHER INFORMATION: PCR primer

<400> SEQUENCE: 17
cagggtggct tctaggtatg tgg                                              23

<210> SEQ ID NO 18
<211> LENGTH: 23
<212> TYPE: DNA
<213> ORGANISM: Artificial Sequence
<220> FEATURE:
<223> OTHER INFORMATION: PCR primer

<400> SEQUENCE: 18
acagcccaag tgaatgacca ggg                                              23

<210> SEQ ID NO 19
<211> LENGTH: 23
<212> TYPE: DNA
<213> ORGANISM: Artificial Sequence
<220> FEATURE:
<223> OTHER INFORMATION: PCR primer

<400> SEQUENCE: 19
gccaggggct ctgggcatgt ggg                                              23

<210> SEQ ID NO 20
<211> LENGTH: 18
<212> TYPE: DNA
<213> ORGANISM: Artificial Sequence
<220> FEATURE:
<223> OTHER INFORMATION: PCR primer

<400> SEQUENCE: 20
ttgagctggc aatcaggg                                                    18

<210> SEQ ID NO 21
<211> LENGTH: 18
<212> TYPE: DNA
<213> ORGANISM: Artificial Sequence
<220> FEATURE:
<223> OTHER INFORMATION: PCR primer

<400> SEQUENCE: 21
ccctgattgc cagctcaa                                                    18

<210> SEQ ID NO 22
<211> LENGTH: 140
<212> TYPE: DNA
<213> ORGANISM: Artificial Sequence
<220> FEATURE:
<223> OTHER INFORMATION: Synthesized sequence

<400> SEQUENCE: 22
gtaaaacgac ggccagtgaa ttctaatacg actcactata ggttgagctg gcaatcaggg      60
gttttagagc tagaaatagc aagttaaaat aaggctagtc cgttatcaac ttgaaaaagt     120
ggcaccgagt cggtgctttt                                                 140

<210> SEQ ID NO 23

<210> SEQ ID NO 23
<211> LENGTH: 25
<212> TYPE: DNA
<213> ORGANISM: Artificial Sequence
<220> FEATURE:
<223> OTHER INFORMATION: PCR primer

<400> SEQUENCE: 23
ccagaagaag gtacagcaga aggggg                                25

<210> SEQ ID NO 24
<211> LENGTH: 25
<212> TYPE: DNA
<213> ORGANISM: Artificial Sequence
<220> FEATURE:
<223> OTHER INFORMATION: PCR primer

<400> SEQUENCE: 24
aagcagcgta tccacatagc gtaaa                                 25

<210> SEQ ID NO 25
<211> LENGTH: 25
<212> TYPE: DNA
<213> ORGANISM: Artificial Sequence
<220> FEATURE:
<223> OTHER INFORMATION: PCR primer

<400> SEQUENCE: 25
gtgcctgtgt tctctgtgga ctatg                                 25

<210> SEQ ID NO 26
<211> LENGTH: 25
<212> TYPE: DNA
<213> ORGANISM: Artificial Sequence
<220> FEATURE:
<223> OTHER INFORMATION: PCR primer

<400> SEQUENCE: 26
ctggtcttga actttgatgg gcacg                                 25

<210> SEQ ID NO 27
<211> LENGTH: 25
<212> TYPE: DNA
<213> ORGANISM: Artificial Sequence
<220> FEATURE:
<223> OTHER INFORMATION: PCR primer

<400> SEQUENCE: 27
tcaacctccc aatgctaacc agaac                                 25

<210> SEQ ID NO 28
<211> LENGTH: 25
<212> TYPE: DNA
<213> ORGANISM: Artificial Sequence
<220> FEATURE:
<223> OTHER INFORMATION: PCR primer

<400> SEQUENCE: 28
cagactgttg gatcaagtgc tgtct                                 25

<210> SEQ ID NO 29
<211> LENGTH: 22
<212> TYPE: DNA
<213> ORGANISM: Artificial Sequence
<220> FEATURE:
<223> OTHER INFORMATION: PCR primer

<400> SEQUENCE: 29
gtggatacgc tgctttaatg cc                                                      22

<210> SEQ ID NO 30
<211> LENGTH: 23
<212> TYPE: DNA
<213> ORGANISM: Artificial Sequence
<220> FEATURE:
<223> OTHER INFORMATION: PCR primer

<400> SEQUENCE: 30
aagggagatc cgactcgtct gag                                                     23

<210> SEQ ID NO 31
<211> LENGTH: 20
<212> TYPE: DNA
<213> ORGANISM: Artificial Sequence
<220> FEATURE:
<223> OTHER INFORMATION: PCR primer

<400> SEQUENCE: 31
cctggctcac agtgtcagag                                                         20

<210> SEQ ID NO 32
<211> LENGTH: 20
<212> TYPE: DNA
<213> ORGANISM: Artificial Sequence
<220> FEATURE:
<223> OTHER INFORMATION: PCR primer

<400> SEQUENCE: 32
cagggctctc ctcgattttt                                                         20

<210> SEQ ID NO 33
<211> LENGTH: 288
<212> TYPE: PRT
<213> ORGANISM: Artificial Sequence
<220> FEATURE:
<223> OTHER INFORMATION: Homo sapiens and Mus musculus

<400> SEQUENCE: 33

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Gly Met Val Ile Gly Ile Met Ser Ala
            165                 170                 175

Leu Val Gly Ile Pro Val Leu Leu Leu Ala Trp Ala Leu Ala Val
        180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
        210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
            245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
            275                 280                 285

<210> SEQ ID NO 34
<211> LENGTH: 2115
<212> TYPE: DNA
<213> ORGANISM: Homo sapiens

<400> SEQUENCE: 34
agtttccctt ccgctcacct ccgcctgagc agtggagaag gcggcactct ggtggggctg    60
ctccaggcat gcagatccca caggcgccct ggccagtcgt ctgggcggtg ctacaactgg   120
gctggcggcc aggatggttc ttagactccc agacaggcc ctggaacccc ccacccttct    180
ccccagccct gctcgtggtg accgaagggg acaacgccac cttcacctgc agcttctcca   240
acacatcgga gagcttcgtg ctaaactggt accgcatgag ccccagcaac agacggacaa   300
agctggccgc cttccccgag accgcagcca gcccggcca ggactgccgc ttccgtgtca    360
cacaactgcc aacgggcgt gacttccaca tgagcgtggt cagggcccgg cgcaatgaca   420
gcggcaccta cctctgtggg gccatctccc tggcccccaa ggcgcagatc aaagagagcc   480
tgcgggcaga gctcagggtg acagagagaa gggcagaagt gcccacagcc cacccccagcc   540 cctcacccag gccagccggc cagttccaaa ccctggtggt tggtgtcgtg ggcggcctgc   600
tgggcagcct ggtgctgcta gtctgggtcc tggccgtcat ctgctcccgg gccgcacgag   660
ggacaatagg agccaggcgc accggccagc ccctgaagga ggaccctca gccgtgcctg    720 tgttctctgt ggactatggg gagctggatt ccagtggcg agagaagacc ccggagcccc   780
ccgtgccctg tgtccctgag cagacggagt atgccaccat tgtctttcct agcggaatgg   840
gcacctcatc ccccgcccgc aggggctcag ctgacggccc tcggagtgcc agccactga    900 ggcctgagga tggacactgc tcttggcccc tctgaccggc ttccttggcc accagtgttc   960
tgcagaccct ccaccatgag cccgggtcag cgcatttcct caggagaagc aggcagggtg   1020
caggccattg caggccgtcc aggggctgag ctgcctgggg cgaccgggg ctccagcctg    1080 cacctgcacc aggcacagcc ccaccacagg actcatgtct caatgcccac agtgagccca   1140
ggcagcaggt gtcaccgtcc cctacaggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gcgtggccc tgcctgacgc cccggagcct   1320
cctgcctgaa cttgggggct ggttggagat ggccttggag cagccaaggt gcccctggca   1380
gtggcatccc gaaacgccct ggacgcaggg cccaagactg gcacaggag tgggaggtac    1440

```
atggggctgg ggactcccca ggagttatct gctccctgca ggcctagaga agtttcaggg    1500
aaggtcagaa gagctcctgg ctgtggtggg cagggcagga aaccccctcca cctttacaca    1560 tgcccaggca gcacctcagg ccctttgtgg ggcaggaag ctgaggcagt aagcgggcag     1620
gcagagctgg aggcctttca ggcccagcca gcactctggc ctcctgccgc cgcattccac    1680
cccagcccct cacaccactc gggagaggga catcctacgg tcccaaggtc aggagggcag    1740
ggctggggtt gactcaggcc cctcccagct gtggccacct gggtgttggg agggcagaag    1800
tgcaggcacc tagggccccc catgtgccca ccctgggagc tctccttgga acccattcct    1860
gaaattattt aaaggggttg gccgggctcc caccagggcc tgggtgggaa ggtacaggcg    1920 ttccccccggg gcctagtacc cccgccgtgg cctatccact cctcacatcc acacactgca    1980
cccccactcc tggggcaggg ccaccagcat ccaggcggcc agcaggcacc tgagtggctg    2040
ggacaaggga tccccccttcc ctgtggttct attatattat aattataatt aaatatgaga    2100
gcatgctaag gaaaa                                                      2115
```

<210> SEQ ID NO 35
<211> LENGTH: 288
<212> TYPE: PRT
<213> ORGANISM: Homo sapiens

<400> SEQUENCE: 35

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
```

```
              245                 250                 255
    Met Gly Thr Ser Ser Pro Ala Arg Arg Gly Ser Ala Asp Gly Pro Arg
                    260                 265                 270

Ser Ala Gln Pro Leu Arg Pro Glu Asp Gly His Cys Ser Trp Pro Leu
                    275                 280                 285

<210> SEQ ID NO 36
<211> LENGTH: 1722
<212> TYPE: DNA
<213> ORGANISM: Artificial Sequence
<220> FEATURE:
<223> OTHER INFORMATION: Homo sapiens and Mus musculus

<400> SEQUENCE: 36
tgccaggggc tctgggcatg cagatcccac aggcgccctg gccagtcgtc tgggcggtgc      60
tacaactggg ctggcggcca ggatggttct tagactcccc agacaggccc tggaaccccc     120
ccaccttctc cccagccctg ctcgtggtga ccgaagggga caacgccacc ttcacctgca     180
gcttctccaa cacatcggag agcttcgtgc taaactggta ccgcatgagc cccagcaacc     240
agacggacaa gctggccgcc ttccccgagg accgcagcca gcccggccag gactgccgct     300
tccgtgtcac acaactgccc aacgggcgtg acttccacat gagcgtggtc agggcccggc     360
gcaatgacag cggcacctac ctctgtgggg ccatctccct ggcccccaag gcgcagatca     420
aagagagcct gcgggcagag ctcagggtga cagagagaag gcagaagtg cccacagccc     480 accccagccc ctcacccagg ccagccggcc agttccaagg catggtcatt ggtatcatga     540
gtgccctagt gggtatccct gtattgctgc tgctggcctg gcccctagct gtcttctgct     600
caacaagtat gtcagaggcc agaggagctg gaagcaagga cgacactctg aaggaggagc     660
cttcagcagc acctgtccct agtgtggcct atgaggagct ggacttccag ggacgagaga     720
agacaccaga gctccctacc gcctgtgtgc acacagaata tgccaccatt gtcttcactg     780
aagggctggg tgcctcggcc atgggacgta ggggctcagc tgatgccctg cagggtcctc     840
ggcctccaag acatgaggat ggacattgtt cttggcctct ttgaaatcaa cctctggatt     900
acaaaatttg tgaaagattg actggtattc ttaactatgt tgctcctttt acgctatgtg     960
gatacgctgc tttaatgcct ttgtatcatg ctattgcttc ccgtatggct ttcattttct    1020
cctccttgta taaatcctgg ttgctgtctc tttatgagga gttgtggccc gttgtcaggc    1080
aacgtggcgt ggtgtgcact gtgtttgctg acgcaacccc cactggttgg ggcattgcca    1140
ccacctgtca gctcctttcc gggactttcg ctttccccct ccctattgcc acggcggaac    1200
tcatcgccgc ctgccttgcc cgctgctgga caggggctcg gctgttgggc actgacaatt    1260
ccgtggtgtt gtcggggaaa tcatcgtcct tccttggct gctcgcctgt gttgccacct    1320
ggattctgcg cgggacgtcc ttctgctacg tcccttcggc cctcaatcca gcggaccttc    1380
cttcccgcgg cctgctgccg gctctgcggc ctcttccgcg tcttcgcctt cgccctcaga    1440
cgagtcggat ctccctttgg gccgcctccc cgcatcgata ccgtcgacct cgactgtgcc    1500
ttctagttgc cagccatctg ttgtttgccc ctcccccgtg ccttccttga ccctggaagg    1560
tgccactccc actgtccttt cctaataaaa tgaggaaatt gcatcgcatt gtctgagtag    1620
gtgtcattct attctggggg gtggggtggg gcaggacagc aagggggagg attgggaaga    1680
caatagcagg catgctgggg aattaatagt actgtatgtg gc                        1722

<210> SEQ ID NO 37
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 37
ccctgctcgt ggtgaccgaa                                                    20

<210> SEQ ID NO 38
<211> LENGTH: 20
<212> TYPE: DNA
<213> ORGANISM: Artificial Sequence
<220> FEATURE:
<223> OTHER INFORMATION: PCR primer

<400> SEQUENCE: 38
gcaggctctc tttgatctgc                                                    20

<210> SEQ ID NO 39
<211> LENGTH: 1696
<212> TYPE: DNA
<213> ORGANISM: Artificial Sequence
<220> FEATURE:
<223> OTHER INFORMATION: Homo sapiens and Mus musculus

<400> SEQUENCE: 39
atgcagatcc cacaggcgcc ctggccagtc gtctgggcgg tgctacaact gggctggcgg        60
ccaggatggt tcttagactc cccagacagg ccctggaacc cccccacctt ctccccagcc       120
ctgctcgtgg tgaccgaagg ggacaacgcc accttcacct gcagcttctc aacacatcg        180 gagagcttcg tgctaaactg gtaccgcatg agccccagca accagacgga caagctggcc       240
gccttccccg aggaccgcag ccagcccggc caggactgcc gcttccgtgt cacacaactg       300
cccaacgggc gtgacttcca catgagcgtg gtcagggccc ggcgcaatga cagcggcacc       360
tacctctgtg gggccatctc cctggccccc aaggcgcaga tcaaagagag cctgcgggca       420
gagctcaggg tgacagagag aagggcagaa gtgcccacag cccaccccag ccctcaccc        480 aggccagccg ccagttccca aggcatggtc attggtatca tgagtgccct agtgggtatc       540
cctgtattgc tgctgctggc ctgggcccta gctgtcttct gctcaacaag tatgtcagag       600
gccagaggag ctggaagcaa ggacgacact ctgaaggagg agccttcagc agcacctgtc       660
cctagtgtgg cctatgagga gctggacttc caggacgag agaagacacc agagctccct       720
accgcctgtg tgcacacaga atatgccacc attgtcttca ctgaagggct gggtgcctcg       780
gccatgggac gtaggggctc agctgatggc ctgcagggtc ctcggcctcc aagacatgag       840
gatggacatt gttcttggcc tctttgaaat caacctctgg attacaaaat ttgtgaaaga       900
ttgactggta ttcttaacta tgttgctcct tttacgctat gtggatacgc tgctttaatg       960
cctttgtatc atgctattgc ttcccgtatg ctttcattt tctcctcctt gtataaatcc       1020
tggttgctgt ctcttatga ggagttgtgg cccgttgtca ggcaacgtgg cgtggtgtgc       1080
actgtgtttg ctgacgcaac ccccactggt tgggcattg ccaccacctg tcagctcctt       1140
tccgggactt tcgctttccc cctccctatt gccacggcgg aactcatcgc cgcctgcctt       1200
gcccgctgct ggacaggggc tcggctgttg gcactgaca attccgtggt gttgtcgggg       1260
aaatcatcgt cctttccttg ctgctcgcc tgtgttgcca cctggattct gcgcgggacg       1320
tccttctgct acgtcccttc ggccctcaat ccagcggacc ttccttcccg cggcctgctg       1380
ccggctctgc ggcctcttcc gcgtcttcgc cttcgccctt agacgagtcg gatctccctt       1440
```

```
tgggccgcct ccccgcatcg ataccgtcga cctcgactgt gccttctagt tgccagccat   1500
ctgttgtttg cccctccccc gtgccttcct tgaccctgga aggtgccact cccactgtcc   1560
tttcctaata aaatgaggaa attgcatcgc attgtctgag taggtgtcat tctattctgg   1620
ggggtggggt ggggcaggac agcaaggggg aggattggga agacaatagc aggcatgctg   1680
gggaattaat agtact                                                  1696

<210> SEQ ID NO 40
<211> LENGTH: 80
<212> TYPE: DNA
<213> ORGANISM: Artificial Sequence
<220> FEATURE:
<223> OTHER INFORMATION: Synthesized sequence

<400> SEQUENCE: 40
gccacggcgg aactcatcgc cgcctgcctt gcccgctgct ggacaggggc tcggctgttg     60
ggcactgaca attccgtggt                                                80
```